(12) United States Patent
Paloheimo et al.

(10) Patent No.: US 7,732,178 B2
(45) Date of Patent: Jun. 8, 2010

(54) LACCASE ENZYMES AND THEIR USES

(75) Inventors: Marja Paloheimo, Vantaa (FI); Terhi Puranen, Nurmijarvi (FI); Leena Valtakari, Rajamaki (FI); Kristiina Kruus, Espoo (FI); Jarno Kallio, Jarvenpaa (FI); Arja Mantyla, Helsinki (FI); Richard Fagerstrom, Espoo (FI); Pentti Ojapalo, Tuusula (FI); Jari Vehmaanpera, Klaukkala (FI)

(73) Assignee: AB Enzymes Oy, Rajamaki (FI)

( * ) Notice: Subject to any disclaimer, the term of this patent is extended or adjusted under 35 U.S.C. 154(b) by 240 days.

(21) Appl. No.: 11/663,424

(22) PCT Filed: Sep. 21, 2005

(86) PCT No.: PCT/FI2005/000398

§ 371 (c)(1),
(2), (4) Date: Jul. 9, 2007

(87) PCT Pub. No.: WO2006/032724

PCT Pub. Date: Mar. 30, 2006

(65) Prior Publication Data

US 2008/0248016 A1 Oct. 9, 2008

Related U.S. Application Data

(60) Provisional application No. 60/611,818, filed on Sep. 21, 2004.

(30) Foreign Application Priority Data

Sep. 21, 2004 (FI) .................................. 20041221

(51) Int. Cl.
*C12N 9/02* (2006.01)
*C12N 1/20* (2006.01)
*C12N 15/00* (2006.01)
*C12Q 1/68* (2006.01)
*C12Q 1/26* (2006.01)
*C12P 21/04* (2006.01)
*C07H 21/04* (2006.01)
*C12Q 1/00* (2006.01)

(52) U.S. Cl. ............................... 435/189; 435/4; 435/6; 435/25; 435/69.1; 435/71.1; 435/440; 435/252.3; 435/320.1; 536/23.2

(58) Field of Classification Search ........................ None
See application file for complete search history.

(56) References Cited

FOREIGN PATENT DOCUMENTS

| EP | 1167528 A1 | 1/2002 |
|---|---|---|
| WO | WO92/01046 | 1/1992 |
| WO | WO97/25468 | 7/1997 |
| WO | WO01/92498 A1 | 12/2001 |

OTHER PUBLICATIONS

Branden et al. Introduction to Protein Structure, Garland Publishing Inc., New York, p. 247, 1991.*
Galagan et al. UniProt Databases—Accession No. Q754C0—Mar. 1, 2004.*
Aho, S., Olkkonen, V., Jalava, T., Paloheimo, M., Buhler, R., Niku-Paavola, M-L., Bamford, D.H and Korhola M. 1991.Monoclonal Antibodies . . . Eur. J. Biochem. 200, 643-649.
Altschul, S.F., Gish, W., Miller, W., Myers, E.W., Lipman, D.J. 1990. Basic local alignmetn search tool. J. Mol. Biol. 215, 403-410.
Edman, P. and Begg. G. 1967. A protein sequenator. Eur. J. Biochem. 1: 80-91.
Gasteiger, E. Gattiker, A. Hoogland, C. Ivanyi, I. Apple, R.D. and Bairoch, A. 2003. ExPASy: the proteomics server . . . Nucleic Acids Res. 31(13):3784-3788.
Joutsjoki, V.V., Torkkeli, T.K. and Nevalainen K.M.H. 1993. Transformation of *Trichoderma reesei* . . . Curr. Genet. 24: 223-228.
Karhunen, T. Mantyla, A. Nevalainen, K.M.H. and Suominen P.L. 1993. High Frequency one-step . . . Mol Gen Genet 241: 515-522.
Laemmli U.K. 1970. Cleavage of Structural Proteins during . . . Nature 277:680-685.
Leonowicz A. and Grzywnowicz K. 1981.Quantitative estimation of laccase forms . . . Enzyme Microbiol Technol 3: 55-58.
Lowry, O.H. , Rosebrough, N. J. Farr, A.L. and Randall, R.J. 1951. Protein measuremetn with the folin . . . J. Biol. Chem 193:265-275.
Malardier, L. Daboussi M.J. Julien, J. Foussel, F. Scazzoccchio C. and Brygoo, Y. 1989. Cloning of the . . . Gene 78: 147-156.
Niku-Paavola, M-L., Karhunen, E. Salola, P and Raunio. V. 1988. Ligninolytict enzymes of hte white-rot . . . Biochem J. 254:877-884.
Paloheimo, m. Mantyla, A. Kallio, J. and Suominen , P. 2003. High-Yield Production of a Bacterial . . . Applied and Environmental Microbiology 69(12): 7073-7082.
Palonen, H. Saloheimo, M, Viikari, L and Kruus, K. 2003. Purification, characterization and sequence . . . Enzyme and Microbial Technol. 33:854-862.
Paszczynski, A. Huynh, V-B. and Crawford R. 1985. Enzymatic activities of an extracellular . . . FEMS Microbiol. lett. 29: 37-41.
Penttila M. Nevalainen, H. Ratto, M, Salminen E. and Knowles J. 1987. A verstile transformation system for . . . Gene 61: 155-164.
Raeder, U. and Broda, P. 1965. Rapid preparation of DNA . . . Letters in Applied Microbiology 1: 17-20.
Rice P., Longden I. and Beashby A. 2000. EMBOSS: The European Molecular Biology . . . TIG 16(6): 276-277.

(Continued)

*Primary Examiner*—Yong D Pak
(74) *Attorney, Agent, or Firm*—Dodds & Associates; L. Susanne Somersalo; John Dodds

(57) ABSTRACT

The present invention relates to novel laccase enzymes obtainable from the strains of the genus *Thielavia* or from the strains of the genus *Chaetomium*. The invention relates also to nucleic acid sequences encoding the enzymes, recombinant hosts into which the nucleic acid sequences have been introduced and to methods for the production of the enzymes in recombinant hosts. The enzymes of the invention are suitable for several applications, for example for treating denim and for strain removal.

21 Claims, 33 Drawing Sheets

OTHER PUBLICATIONS

Schlosser D. Grey R and Fritsche W. 1997. Patterns of ligninolytic enzymes . . . Appl. Microbiol. Biotechnol 47: 412-418.

Sigoilot C. Record E. Belle V. Robert J.L. Lavasseru, A, Punt, P.J. Van Den Honle, C.A.M.J.J. Fournel A. Sigoilot J.C and Asther M. 2004: Appl. Microbiol. Biotech. 64: 346-352.

Stone K.L. Lopresti, M. William. N.D. Crawford J.M. Deangelis, R and Williams, K. R. 1988. In Techniques in Protein Chemistry p. 333-391/ T. E. Hugli (ed) Academic Press NY.

Xu, F.; Shin, W., Brown, S. Wahleiner, J. Sudaram, U. and Solomon E. 1996 a study of a series of recombinant fungal laccases and bilirubin . . . Biochim. Biophys. 1292:303-311.

Scholsser D, Grey R, and Fritsche W. 1997. Patterns of lininolytic enzymes in *Trametes versicolor*. Appl Microbiol Biotechnol 47: 412-418.

Saito, T, et al. . 2003. Purification and characterization of an extracellular laccase of a fungus (family Chetomiaceae) . . . Enzyme and Microbial Technology 33:520-526.

Chefetz, B. et al. 1998. Isolation and Partial Characterization of laccase from a thermophilic composted municipal solid waste. Soil Biol. Biochem 30(8/9) 1091-1098.

Chefetz, B. Chen Y and Hadar Y. 1998. Purification and Characterization of laccase from *Chaetomium thermophilium* and its role . . . Appl. and Env. Microbiology 64(9): 3175-3179.

Kiiskinen, L-L.; Rattto, M and Kruus K. 2004. Screenign for novel laccase producing microbes. J. Appl. Microb. 97:640-646.

Kumar, S.V.S., Phale, P.S., Durani, S.; Wangikar, P.P. 2003. Combinend Sequence ans Structure Analysisof the fungal laccase family. Biotech & Bioeng. 83(4):386-394.

Saito T; Hong, P, Kato, K,,Okazaki, M; Inagaki, H, Maeda, S, Yokogawa Y. 2003: Purification and characterization of an extracellular . . . Enz. and Microb. Tech. 33: 520-526.

Chefetz, B., Chen, Y, Hadar, Y. 1998: Purification and characterization of laccase . . . Appl. ENv. Microb. 64(9): 3175-3179.

EMBL/GenBank/DDBJ database. Acc. No. AY653227, 2004.

EMBL/GenBank/DDBJ database./ Acc. No. AY65322, 2004.

* cited by examiner

```
Peptide I
 1   2   3   4   5   6
 W   Y   H   S   H   F
TGG TAC CAC AGA CAC TTC
     T   T  TCC  T   T
             T
             G Peptide II
 1   2   3   4   5   6   7
(M)  H   L   H   G   H   D
ATG CAC CTA CAC GGA CAC GAC
     T   T C  T   C   T   T
         T       T
         G       G Peptide III
 1   2   3   4   5   6   7   8
(M)  H   C   H   I   A   W   H
ATG CAC TGC CAC ATA GCA TGG CAC
     T   T   T   C   C       T
                 T   T
                     G
```

Fig. 5A

```
Peptide 1
 1   2   3   4   5   6   7   8   9   10  11    12      13  14  15  16  17  18  19
 Y   Q   G   A   P   N   T   L   P   T   N    Q/I      G   L   P   V   P   N   H
TAC CAA GGA GCA CCA AAC ACA CTA CCA ACA AAC CAA/ATA  GGA CTA CCA GTA CCA AAC CAC
 T   G   C   C   C   T   C T C   C   C   T   G   C   C T C  C   C   C   T   T
         G   G   G       G   G   G   G       T       G   G   G   G   G
         T   T   T       T   T   T   T               T   T   T   T   T Peptide 2
 1   2   3   4   5   6   7   8   9   10  11
 E   N   W   I   G   P   D   G   V   L   K
GAA AAC TGG ATA GGA CCA GAC GGA GTA CTA AAA
 G   T       C   C   C   T   C   C T C   G
             T   G   G       G   G   G
             T   T       T   T   T Peptide 3
 1   2   3   4   5   6   7   8   9
(S)  L   F   L   A   V   G   Q   R
AGA CTA TTC CTA GCA GTA GGA CAA AGA
TCC T C  T T C   C   C   C       G C C
 G   G       G   G   G   G       G
 T   T       T   T   T   T       T
```

Fig. 5B

N-terminal peptide
```
  1   2   3   4   5   6   7   8   9  10  11  12  13  14  15  16  17  18  19  20
  E   G   P   G   P   C   H   T   P   A   N   Y   A   C   W   A   P   G   F   D
GAA GGT CCT GGT CCT TGT CAT ACT CCT GCT AAT TAT GCT TGT TGG GCT CCT GGT TTT GAT
  G   C   C   C   C   C   C   C   C   C   C   C   C   C       C   C   C   C   C
      A   A   A       A       A   A   A       A       A       A   A   A
      G   G   G               G   G   G       G               G   G   G
```

Peptide 18.9
```
  1   2   3   4   5   6   7   8   9  10  11  12  13  14  15
  L   T   E   N   D   N   W   T   G   P   D   G   V   V   K
TTT ACT GAA AAT GAT AAT TGG ACT GGT CCT GAT GGT GTT GTT AAA
C C   C   G   C   C   C           C   C   C   C   C   C   G
  A   A                       A   A   A       A   A   A
  G   G                       G   G   G       G   G   G
```

Fig. 5C

*Ta lcc1* and the deduced amino acid sequence

```
1     ggatccccgggtcagtctatataaggggctgagtgtccagctcttccatgcctttgattc
61    tcttgaatcaccaggacactcgggcggcttcagtcttgcataactcgggtcttcccttcc
121   tctcactgcttttcttcgctcagatatatttcaggcgacctcaaacagctcgccatcATG
1                                                                M 181   AAGTCTTGGGCCGCCGCCGTGGCGCTCATGGTGGGCATTCTCAGCCCTCATGCTGCCGCC
2      K  S  W  A  A  A  V  A  L  M  V  G  I  L  S  P  H  A  A  A 241   GCACCTCCTGCAAACCCGGTCCAGAGAGACATGCTCCAGGTCCTTGAGGCGAGACAGTCT
22     A  P  P  A  N  P  V  Q  R  D  M  L  Q  V  L  E  A  R  Q  S 301   GGCCCGACTTGCAACACCCCGTCCAATCGTGCGTGCTGGACCAATGGTTTCGACATCAAC
42     G  P  T  C  N  T  P  S  N  R  A  C  W  T  N  G  F  D  I  N 361   ACCGACTATGAAGTCAGCACTCCTAATACCGGACGTACTGTGGCCgtaagcttcccctcc
62     T  D  Y  E  V  S  T  P  N  T  G  R  T  V  A  intron 1 (51 bp)

421   ctttaaggaggcagagctaggactaacaagcaccagTACCAACTTACCCTCACTGAGAAA
77                                         Y  Q  L  T  L  T  E  K 481   GAGAACTGGATCGGTCCCGATGGCGTTCTCAAGAATGTGGTGATGTTGGTCAATGgtacg        Peptide 2
85     E  N  W  I  G  P  D  G  V  L  K  N  V  V  M  L  V  N  D 541   ttgatgtccaattctgtataaagagaagaaacgtgctgatacgctcccttcgtctagACA
104             intron 2 (62 bp)                                  K 601   AGATTATAGgtatgttgtcaaaccgctgtaaccccaaccgccaagacctggaggctcct
105    I  I  G             intron 3 (91 bp)

661   cgcctggacgtgttgtacaatatgctgacctcgccgccagGGCCAACCATCCGCGCGAAC
108                                             P  T  I  R  A  N 721   TGGGGTGACAATATCGAAGTCACTGTCATCAACAATCTCAAAACCAATGGgtacgaccac
114    W  G  D  N  I  E  V  T  V  I  N  N  L  K  T  N  G 781   ttgaatcatcccgggcctaccccctaacacaaaatctcaacgtgcatccgatctgacgtat
      intron 4 (83 bp)

841   tatatccatctagTACCTCGATGCACTGGCATGGCCTTCGTCAGCTGGGTAACGTTTTCA        Cu-binding
131                  T  S  M  H  W  H  G  L  R  Q  L  G  N  V  F  N 901   ACGACGGTGCCAACGGCGTGACTGAGTGCCCAATCCCGCCCAAAGGAGGGCGCAAGACGT
147    D  G  A  N  G  V  T  E  C  P  I  P  P  K  G  G  R  K  T 961   ACAAGTTCCGTGCGACACAGTATGGCACCAGCTGGTATCACTCCCACTTCTCGGCCCAGT        Cu-binding
167    K  F  R  A  T  Q  Y  G  T  S  W  Y  H  S  H  F  S  A  Q  Y 1021  ACGGCAACGGCGTGGTCGGCACCATCCAGATCGACGGCCCTGCCTCTCTGCCATATGACA
187    G  N  G  V  V  G  T  I  Q  I  D  G  P  A  S  L  P  Y  D  I 1081  TTGATCTGGGCGTGTTCCCTCTCATGGACTACTACTACAGGTCGGCCGATGAGCTGGTGC
207    D  L  G  V  F  P  L  M  D  Y  Y  Y  R  S  A  D  E  L  V  H 1141  ACTTCACCCAGAGCAACGGCGCCCCGCCAAGCGACAACGTCCTCTTCAATGGCACCGCCC
227    F  T  Q  S  N  G  A  P  P  S  D  N  V  L  F  N  G  T  A  R 1201  GTCACCCTGAGACGGGGGCAGGCCAGTGGTACAACGTCACGCTGACTCCAGGCAAGCGAC
247    H  P  E  T  G  A  G  Q  W  Y  N  V  T  L  T  P  G  K  R  H 1261  ACCGCCTGCGCATCATCAACACGTCGACCGACAACCACTTTCAGGTGTCGCTTGTCGGCC
267    R  L  R  I  I  N  T  S  T  D  N  H  F  Q  V  S  L  V  G  H
```

Fig. 6A I

```
1321  ACAACATGACCGTCATTGCCACCGACATGGTCCCCGTCAACGCCTTTACTGTCAGCAGCC
 287     N  M  T  V  I  A  T  D  M  V  P  V  N  A  F  T  V  S  S  L

1381  TATTCCTCGCCGTAGGCCAGCGATACGATGTCACCATCGACGCCAATAGCCCGGTGGGCA              Peptide 3
 307     F  L  A  V  G  Q  R  Y  D  V  T  I  D  A  N  S  P  V  G  N 1441  ACTACTGGTTCAACGTGACTTTCGGCGATGGGTTGTGCGGCTCCAGTAACAACAAATTCC
 327     Y  W  F  N  V  T  F  G  D  G  L  C  G  S  S  N  N  K  F  P 1501  CAGCCGCCATCTTCCGCTACCAGGGCGCCCCCGCTACGCTCCCGACGGATCAGGGTCTAC              Peptide 1
 347     A  A  I  F  R  Y  Q  G  A  P  A  T  L  P  T  D  Q  G  L  P 1561  CCGTGCCCAATCACATGTGTTTGGACAACCTGAACCTAACTCCTGTGGTGACACGGAGCG
 367     V  P  N  H  M  C  L  D  N  L  N  L  T  P  V  V  T  R  S  A 1621  CGCCCGTCAACAACTTTGTCAAGCGTCCGTCCAACACGCTGGGCGTCACTCTCGATATCG
 387     P  V  N  N  F  V  K  R  P  S  N  T  L  G  V  T  L  D  I  G 1681  GCGGCACGCCGCTCTTTGTGTGGAAGGTCAACGGCAGCGCCATCAACGTCGACTGGGGCA
 407     G  T  P  L  F  V  W  K  V  N  G  S  A  I  N  V  D  W  G  K 1741  AGCCGATCCTTGACTATGTCATGAGCGGCAACACGAGCTACCCGGTCAGCGATAACATTG
 427     P  I  L  D  Y  V  M  S  G  N  T  S  Y  P  V  S  D  N  I  V 1801  TGCAGGTGGACGCTGTTGACCAGgtacgccctcttgaagccctagcagttcacgctag
 447     Q  V  D  A  V  D  Q           intron 5 (79 bp)

1861  tatacaatacaagtacatgctaacacttccctccctattcagTGGACTTACTGGCTGATC
 454                                                W  T  Y  W  L  I 1921  GAGAACGACCCGACCAATCCCATTGTCAGCTTGCCGCACCCGATGCATCTGCACgtacgt              Cu-binding
 460     E  N  D  P  T  N  P  I  V  S  L  P  H  P  M  H  L  H 1981  tcaaacctcccccacccccccacttcatacaaaatatactgacaaatcgacagGGCCACG
 478             intron 6 (59 bp)                                 G  H  D 2041  ACTTCCTCGTCCTGGGCCGATCACCCGACGAGCTCCCCAGCGCGGGGGTCCGTCACATCT
 481     F  L  V  L  G  R  S  P  D  E  L  P  S  A  G  V  R  H  I  F 2101  TTGACCCGGCCAAGGACCTGCCCCGGCTTAAGGGCAACAACCCCGTGCGGCGGGACGTGA
 501     D  P  A  K  D  L  P  R  L  K  G  N  N  P  V  R  R  D  V  T 2161  CGATGCTTCCGGCGGGCGGCTGGCTGCTGCTGGCGTTCAAGACGGACAACCCCGGGGCAT
 521     M  L  P  A  G  G  W  L  L  L  A  F  K  T  D  N  P  G  A  W 2221  GGCTGTTCCACTGCCACATTGCGTGGCACGTGTCGGGCGGCCTGTCGGTCGACTTCCTCG              Cu-binding
 541     L  F  H  C  H  I  A  W  H  V  S  G  G  L  S  V  D  F  L  E 2281  AGCGGCCCAACGACCTTCGCACGCAGCTCAACAGCAACGCCAAGCGCGCCGACCGCGACG
 561     R  P  N  D  L  R  T  Q  L  N  S  N  A  K  R  A  D  R  D  D 2341  ACTTCAACCGCGTCTGCCGCGAGTGGAACGCCTACTGGCCTACCAACCCGTTCCCCAAGA
 581     F  N  R  V  C  R  E  W  N  A  Y  W  P  T  N  P  F  P  K  I 2401  TCGACTCGGGCTTGAGGCACCGGTTTGTTGAGGAGAGCGAGTGGATGGTTCGCTAAactg
 601     D  S  G  L  R  H  R  F  V  E  E  S  E  W  M  V  R  *

2461  cctggctgtgccaactgatttgatgggtacatgtacctgttggtgttactgttgacgagg
2521  ctgtgtaagtaccatggcaaaggggtgttttcagggggtgctctggggtaattggcacagt
2581  acatggagggggtctgggggttgggtatacaaggcttgctgctccgttttttatcttttggct
2641  tgattaagactttcttgtctgatgtacgagtcaggccgcc
```

Fig. 6A II

*Ta lcc2* and the deduced amino acid sequence

```
  1 ggatcccgtagtcaacaagacccagcacccagggtaaccatcctatacggggcaagatct
 61 accacttgcagcgatatattgaagtccaatacatcgtcactgtagtagtcatggtgttct
121 gtaagttccggcagggactgtagtactcgacgggttcctctccttccagttagccctcgt
181 agagcatgttgacgttacgataggtttccccccccccatttggagctgtgatatactttc
241 aagttgttgaaggcctttagctgagcataacgatcgtggctgacgaaagcctccgtgcgg
301 cacacctaaaattacgattccgaatgctcctccaaggagttgtcatatgatactattgat
361 gtgagcttcaggggagcaggccattacggaaggtagaccagggacaactccttctcggc
421 ttaaccgggccggatcgtggaatgcctcgccaaagactcattgcgaggcgacatggagcc
481 aagcccaccttctcttgaggctctgatattgatgctgtacgagtataaagtcgatgatct
541 cctgcaatgtcccagagtctatccaagcagctcttggaccaaggaagccatcggtcactc
```

```
601 aacaggcgcggccacattcgttcaactttgaattggtagcacc[ATG]TTAACCGAGACACT
  1                                              M  L  T  E  T  L 661 CAAGTCAAGAAAC[ATG]TTGCAATCAATCCTTGCTCTTCTTGCCACCGCCCTGGGCTCATC
  7  K  S  R  N   M  L  Q  S  I  L  A  L  L  A  T  A  L  G  S  S 721 TGCCTTCGCCATCCCTGAACTCCCAGAGGTCTCGCTTCAGCCCCGGCAAGCTTGCGAGAA
 27  A  F  A  I  P  E  L  P  E  V  S  L  Q  P  R  Q  A  C  E  N 781 CACTGCAACGTCTCGCCAATGCTGGGGTGACCTTTCAATCGACACCAACTACTATGAAGT
 47  T  A  T  S  R  Q  C  W  G  D  L  S  I  D  T  N  Y  Y  E  V 841 TCTTCCCAGCACCGGGCGCCCGCCGCAGGAGTATTGGCTGAGTGTCGTGGAAGGCCCTTG
 67  L  P  S  T  G  R  P  P  Q  E  Y  W  L  S  V  V  E  G  P  C 901 TGCCCCAGACGGATATAACAGGACCTGTATGACCTTTAACGGCACCGTGCCGGGGCCAAC
 87  A  P  D  G  Y  N  R  T  C  M  T  F  N  G  T  V  P  G  P  T 961 CCTCTTCGCCGATTGGGGCGACGAGCTCGTTATCCATGTCACAAACAACATGGTCAACAA
107  L  F  A  D  W  G  D  E  L  V  I  H  V  T  N  N  M  V  N  N 1021 TGGCACCGCGATCCACTGGCACGGGATTCGCATGCTGAATAACACGCTCAACGACGGCGT
127  G  T  A  I  H  W  H  G  I  R  M  L  N  N  T  L  N  D  G  V   Cu-binding 1081 TCCCGGAGTGACGCAGTGCGCCATCGCCCCGGGCGAGTCCATGACATACCGGTTCAACGT
147  P  G  V  T  Q  C  A  I  A  P  G  E  S  M  T  Y  R  F  N  V 1141 CACCCAGTACGGCTCGACTTGGTACCACAGCCACTTCAGCCTCCAGTACGCCGAGGGTCT
167  T  Q  Y  G  S  T  W  Y  H  S  H  F  S  L  Q  Y  A  E  G  L   Cu-binding 1201 CTTCGGGGGCATGATTCTCCGGGGGCCCAGCACGGCCAACTGGGACGAGGACCTCGGAGT
187  F  G  G  M  I  L  R  G  P  S  T  A  N  W  D  E  D  L  G  V 1261 CTTGTTTCTGCAGGACTGGTCACACGTCGAAGCCTTCACTAGGTGGCATGAAGCGAAAGC
207  L  F  L  Q  D  W  S  H  V  E  A  F  T  R  W  H  E  A  K  A 1321 CGGGTTTCCTCCATCACTCGATGGCGGCCTGATCAACGGCACAAACACATTTGACTGCTC
227  G  F  P  P  S  L  D  G  G  L  I  N  G  T  N  F  D  C  S 1381 CACACTGTCGCCGACGGACCCCAAGTGCACCGGCAATGGCAAGAAGTTCGAGACCGTCTT
247  T  L  S  P  T  D  P  K  C  T  G  N  G  K  K  F  E  T  V  F 1441 CGAACCCGGCAAGAAGTATCTTATCCGCCTCATCAACGTGGCAATCGACGGAGTGTTCCA
267  E  P  G  K  K  Y  L  I  R  L  I  N  V  A  I  D  G  V  F  Q 1501 GTTCAGCATCGACGGACACAGCCTCACCGTCATAGCGACGGATTTGGTGCCGATTGTCCC
287  F  S  I  D  G  H  S  L  T  V  I  A  T  D  L  V  P  I  V  P
```

Fig. 6B I

```
1561 CTACACGACCGACAGCGTCCAGATCACCATCGGCCAGCGTTATGATATCATTGTCGAGGC
 307  Y  T  T  D  S  V  Q  I  T  I  G  Q  R  Y  D  I  I  V  E  A

1621 AAACGCAACGCCGGGAAACTACTGGATGCGGGCCGACTGGGTCACAGCCTGCGTGACCAA
 327  N  A  T  P  G  N  Y  W  M  R  A  D  W  V  T  A  C  V  T  N

1681 CGATCACCCCGAGCACATGACGGGCATCGTTCGCTATGACGCGAGCAGCATCGACCCCCC
 347  D  H  P  E  H  M  T  G  I  V  R  Y  D  A  S  S  I  D  P  P

1741 GACGTCCGAAAGCAACGTCACAAAAACCAGCAGCTGCCTCGGCGAGCCGAATGAGAAAAC
 367  T  S  E  S  N  V  T  K  T  S  S  C  L  G  E  P  N  E  K  T

1801 GATCCCGCATTTGTCGCTCGATGTCACCAACATTGGCGGCACCAACGTCGAGGAACTGTC
 387  I  P  H  L  S  L  D  V  T  N  I  G  G  T  N  V  E  E  L  S

1861 CTTTGACACCACCTCTGGCGACTACTTCCAGTGGACTCTCAATACGAGCAGCCTGGTGCT
 407  F  D  T  T  S  G  D  Y  F  Q  W  T  L  N  T  S  S  L  V  L

1921 CGATTGGGGGAACCCGACGATGGCCCGAATCTTCAACGGGGATGCCATCTTCCCCACCGA
 427  D  W  G  N  P  T  M  A  R  I  F  N  G  D  A  I  F  P  T  E

1981 GTACAACGTCGTTGCCGTCAACgtgagtctccccatgtttgcagtaaccccgaaccccta
 447  Y  N  V  V  A  V  N         intron 1 (80 bp)

2041 gagagtgcggcgatttcgctaatcatggttccctatccgcagAAAACCGGCACTGGACCG
 454                                            K  T  G  T  G  P 2101 GAATGGACAGTCCTAGTGATTCAAGATCAAAGCAATTTGCCgtaagcctcccaaattccc
 460  E  W  T  V  L  V  I  Q  D  Q  S  N  L  P 2161 aatccacttgtccctgcccttgcaagtcaggtgcgctgcgtgggaatgggatcccagctg
                        intron 2 (107 bp)

2221 acgtcaaggcttttcatttgtttgcagCATTGCGCATCCGATCCACCTGCACGGCCACG   Cu-binding
 474                            I  A  H  P  I  H  L  H  G  H  D 2281 ACTTTTGGGTGCTGGCGGCCGAGGAGGGCGTCTTCAATGGCAACATTAGCAGCTTCAACA
 485  F  W  V  L  A  A  E  E  G  V  F  N  G  N  I  S  S  F  N  T 2341 CGAGGAACCCGGCGCGGCGCGACGTCGCCACGCTGCCGGGCAGAGGCTACCTGGCCATCG
 505  R  N  P  A  R  R  D  V  A  T  L  P  G  R  G  Y  L  A  I  A 2401 CCTTCCAGATCGACAACCCGGGCACCTGGCTGACCCACTGCCACATTGCCTGGCACGCCA   Cu-binding
 525  F  Q  I  D  N  P  G  T  W  L  T  H  C  H  I  A  W  H  A  S 2461 GCCAGGGCCTTTCGCTCGAGTTTGTCGAGAGCCAGTCCGAGATTGTGACCGACGAGGTCA
 545  Q  G  L  S  L  E  F  V  E  S  Q  S  E  I  V  T  D  E  V  S 2521 GCCGCGGCGTGTTTAACGACGTCTGCGCTTCCTGGCGGGCACATGACCCCCTTTGGGAGC
 565  R  G  V  F  N  D  V  C  A  S  W  R  A  H  D  P  L  W  E  Q 2581 AGGAGGACTCGGGAATTTGAatctgagggcgtcgtttctttccttccggtgtttgagagt
 585  E  D  S  G  I  *

2641 aagatatgtatcatgaaatttctttattcttatttttgttctttctttggtccgtgtt
2701 gtctgctctgcgggttagaatacacgaggaaacccaactgggtgttgagtggactcttcg
2761 ggctcgagcccaacgctcattgtttccctagaagttgtctttgtttctggttcaccactc
2821 caccatttgtacggggtagttgacggattgttcggctcactcaaccggctgtaagtgttg
2881 gagatgtttcaactctcaatctcggaggttgggctgcgctcctgcgatgaggggatggt
2941 cgcagtatgtgctgttagtacagaaaaacacagcataaagcaatacgaactgtgtgcccg
3001 tccgtacctaaggaacaaaccggtcaacaagacacccagtgaaaggttatcagtccaagc
3061 cactcgggttgaatttctcagctc
```

Fig. 6B II

Ta *lcc3* and the deduced amino acid sequence

```
  1 acggctgcggttatcggagcacgttgcatggcaatgtccatactcttactgagaaaagag
 61 ttcggtcaagggacggtgctggggaatagatgcccgtctaggaattccggtagtggcggt
121 cttcggaaatataaccgagcaggacgttcagcccatcgtccctgtgtatataaagcatg
181 aagttattctatgtagaatcctagactatcttagaagcgaacctttcgtcgcagatgctt 241 cgtgttttccatcattacttcccgtagtactagtATGGTCTGCCTTCAGTATCAGCTCAC
  1                                    M  V  C  L  Q  Y  Q  L  T 301 AGCAGCCTGCTTTGCTGTGTTAGCGGTCGTCACCACCCCAGCTTCCTGCTCTCCTGTCCA
 10  A  A  C  F  A  V  L  A  V  V  T  T  P  A  S  C  S  P  V  Q 361 GCCGAGCCCCGTTCACGATCTCTTACCAAGACAAACAATAATCCCCGGCGGTAAGCCATG
 30  P  S  P  V  H  D  L  L  P  R  Q  T  I  I  P  G  G  K  P  C 421 TGGTCAAAATAATGCCACGAATAGGGGGTGCTGGAAAAACAACTGGAACATCACCACCGA
 50  G  Q  N  N  A  T  N  R  G  C  W  K  N  N  W  N  I  T  T  D 481 CTATGAAGTCGACACGCCCCCTGCGTTCAACACCAGAGTGgtatgtccttgctcataata
 70  Y  E  V  D  T  P  P  A  F  N  T  R  V 541 agtggctagcctcgaagatcaggccaaagactgataggagctcagTATGACCTTCACATC
  1            intron 1 (65 bp)                   Y  D  L  H  I 601 ACCAATGTCACCAACTGGCTCGGCCCTGATGGGGTTCGGAAGCCTGCCATGCTTATAAAC
  6  T  N  V  T  N  W  L  G  P  D  G  V  R  K  P  A  M  L  I  N 661 GgtgtgttgccagagcccacaagatcctccaaggtcacttctgacaacaaggcagGCTCA
 26  G             intron 2 (54 bp)                           S 721 TTCCCTGGTCCCACAATCTCAGCCGACTGGGGCGACTACATTATTGTCAATGTCCACAAT
  2  F  P  G  P  T  I  S  A  D  W  G  D  Y  I  I  V  N  V  H  N 781 GACATGCAAGATAACGGgtaagaaatgcagcacggtaccccccggcatcctcaaacctgct
 22  D  M  Q  D  N  G            intron 3 (60 bp)

841 tgctaacacataggtagAACGTCAATCCATTGGCATGGAATCCGTCAGCTTGGCGAGAGC
  1                  T  S  I  H  W  H  G  I  R  Q  L  G  E  S     Cu-binding 901 AACCAGGACGGCGCAAACGGCGTAACGGAATGCCCCATTCCTCCCGGATCCAGCAAAACC
 15  N  Q  D  G  A  N  G  V  T  E  C  P  I  P  P  G  S  S  K  T 961 TACGACTTCCATGTGACGCAGTACGGCACCTCGTGGTACCACAGCCACTACTCCAACCAG
 35  Y  D  F  H  V  T  Q  Y  G  T  S  W  Y  H  S  H  Y  S  N  Q    Cu-binding 1021 TACGGCAATGGGGTCGTGGGCGCCCTGATCGTGCGCGGCCCGGCATCAGCCAACTACGAC
 55  Y  G  N  G  V  V  G  A  L  I  V  R  G  P  A  S  A  N  Y  D 1081 ATCGACCTCGGTCCCTACCTGATCAGTGACTACTACTACGAAACCGCAGACCGCCTCCAT
 75  I  D  L  G  P  Y  L  I  S  D  Y  Y  Y  E  T  A  D  R  L  H 1141 CTCCGAGCCGAGCTGGTCAGCAACGGCCCACCGCCAGACAGCGACAACATCCTGTTCCGC
 95  L  R  A  E  L  V  S  N  G  P  P  P  D  S  D  N  I  L  F  R 1201 GGCAAAAACATCAACCCCAAGCGTGCAGGCAGCGGCTCCTACGACCGCCTCGTCCTAACC
115  G  K  N  I  N  P  K  R  A  G  S  G  S  Y  D  R  L  V  L  T 1261 CCCGGCAAGAAGCATCTAATCCGGCTCATCAACGCCAGCGTGGACAACTCCTTCGTCATC
135  P  G  K  K  H  L  I  R  L  I  N  A  S  V  D  N  S  F  V  I 1321 TCCCTCGTCGGCCACAACTTCACCGTCATCTCCACCGACATGGTCCCCATCACCCCTGTC
155  S  L  V  G  H  N  F  T  V  I  S  T  D  M  V  P  I  T  P  V
```

Fig. 6C I

```
1381 GTGCGCAGCTCCTTATTCATGGGCGTCGGCCAGCGGTACGACGTCATTGTCGAAGCCAAC
 175  V   R   S   S   L   F   M   G   V   G   Q   R   Y   D   V   I   V   E   A   N

1441 CAGCCCGTGGGCAACTACTGGCTCAACGCGACGCTCGAGGCCCAGAACAACTGCGGGCAT
 195  Q   P   V   G   N   Y   W   L   N   A   T   L   E   A   Q   N   N   C   G   H

1501 TCGGTCAACCCCTTCCCCGCGGCTATTGTCCAGTACGAGGGCGCCAGCTCCACCGCCCTG
 215  S   V   N   P   F   P   A   A   I   V   Q   Y   E   G   A   S   S   T   A   L

1561 CCGACCAACCGCGGGACGCCCCTGACGGCGACATGCAATGGCGAGAAAGGGTTTTCGCCC
 235  P   T   N   R   G   T   P   L   T   A   T   C   N   G   E   K   G   F   S   P

1621 ATTGTTAAGCGGACAGTTTCAAGTTCCCTGTTCCAGCCGTCTACCCTGCCAGTCAGCCTT
 255  I   V   K   R   T   V   S   S   S   L   F   Q   P   S   T   L   P   V   S   L

1681 GAATTCCCCACTACAGACCGCGGGCAGGTGTTTGAGTGGCGGGTTAAGAACACGCCGATA
 275  E   F   P   T   T   D   R   G   Q   V   F   E   W   R   V   K   N   T   P   I

1741 AGCGTCGAATGGGAGCATCCCGTGCTGGAGTACATTTTGCAGGGGAACACCTCCTTCCCG
 295  S   V   E   W   E   H   P   V   L   E   Y   I   L   Q   G   N   T   S   F   P

1801 GCAAAGGCCAATCTCATTGAAGTCCCGCAGGCAAATGTCTGGACGTTCTGGGTGATTCAG
 315  A   K   A   N   L   I   E   V   P   Q   A   N   V   W   T   F   W   V   I   Q

1861 AACGGGTTTGGGCTGCCGCACCCGATTCACCTGCATGGGCATGATTTCCTGGTGCTTGGG
 335  N   G   F   G   L   P   H   P   I   H   L   H   G   H   D   F   L   V   L   G      Cu-binding 1921 GTCGGCAACGGGACTTTTGATGCTGCGTCTATGAGGGGGCTGTTGAATTTTAATAATCCT
 355  V   G   N   G   T   F   D   A   A   S   M   R   G   L   L   N   F   N   N   P 1981 GTTCGTAGGGATGTCGAGCAGATGCCTGGCAATGGGTGGCTCGTGATTGCGTTCAAGACG
 375  V   R   R   D   V   E   Q   M   P   G   N   G   W   L   V   I   A   F   K   T 2041 GATAATCCGGGGTGCTGGTTGATGCATTGCCATATTGGCTGGCATGTGGCTATGGGGCTG
 395  D   N   P   G   C   W   L   M   H   C   H   I   G   W   H   V   A   M   G   L      Cu-binding 2101 GGGATACAGTTTTTGGAACGGAGGAGTGATATCCTAGCGCTCATGAAGCTGGATCAGATG
 415  G   I   Q   F   L   E   R   R   S   D   I   L   A   L   M   K   L   D   Q   M 2161 GTGCCCAATTGTGAGGCTTGGAGGGCCTATGCAAGGACGAGTCCATATCTGCCAAAGCTT
 435  V   P   N   C   E   A   W   R   A   Y   A   R   T   S   P   Y   L   P   K   L 2221 GATTCGGGGCTGAAAAGGGGGGTGGAGATGAGGGAGGGGATGGAGCCGGCTGTGAGGCGC
 455  D   S   G   L   K   R   G   V   E   M   R   E   G   M   E   P   A   V   R   R 2281 ATTGGTTAGattgaggtatcgtactcaacttgcttccaagctggctatggctatgagtgg
 475  I   G   *

2341 ttcaggaagaagagggaatctcactattcttgcagcatgcccaactaagataaaaaggaa
2401 ctgaaaaagaactcacccattgtgcgggttgaacgacatgggaccgcctgaccgctgaag
2461 tgacatcattactatcttcaccacgctgagcattcgaattcccagacgcccttggtagtg
2521 gccatttggatggcttaccgtgactctggacgaaagaggtgcgcaagactccgcatggtc
2581 aggggtcatatcgccaatggcgtcatcccgccagggattaaggcagctcataaaccctac
2641 tttggtctcttgccttacaacgccttcctgacattaggacatggaatagacatcattact
2701 attgaagatgtttggacacatgcaatgcgtactttgagttgctatcaaaaagcatgaaac
2761 agcgatgtaggtgaggtactcaatagatatggcgtttaagcagaaataccaatcatttca
2821 ggagataataaccgtcaactcacgcagggcttcaacgttggagtggtgacgacaggcccc
2881 tgacgtcttggttgctggagggatcgtcaggggttaaaaataagggttagggttcaagtc
2941 ttccgtcaactccctaaggaggcaaggatcc
```

Fig. 6C II

*Ta lcc4* and the deduced amino acid sequence

```
   1 ggatccgggaaggtgactgagaagatgtccacgctatggcctcgccgtgtctcaaagaga
  61 tggcgttctctggctcgtgatgttcggatttgacgacggcggtgattggcaacgactttg
 121 cgggacgttggatttggacactttgggggtttgacaatggcgagagcgagacaagtaggt
 181 actaaccgctttcctccaggatttctgtgctgggaggcgccagggaggcgggctgacgat
 241 ggacttggttacaagggagtgaagatgtggcttacagggacgtacatctactatataagc
 301 tgaacactgtggcacttctctgagaaaagcaatgggcaggtatctcagtacatgttcagg
 361 accccttaagttgaccatttcaacttacatgcttcttccaactcgtttctccctcgtcgg
```

```
 421 cccttggaagtttagaccgggctcttacatgacaATGATTTCGCGTCTTCTTTTCACAAG
   1                                   M  I  S  R  L  L  F  T  S 481 CAGTTTCACTGCTACACTGGCTTCTGCTCTGCCAGGTCTATTATACGCCCCTCATTCAAG
  10  S  F  T  A  T  L  A  S  A  L  P  G  L  L  Y  A  P  H  S  S 541 CGCACTGCTGGCTCGTTCCTCCTGTAGCGGCAATACGGCGTCAACCCGGTCCCAGTGGTG
  30  A  L  L  A  R  S  S  C  S  G  N  T  A  S  T  R  S  Q  W  C 601 CGACTACTCCATCGACACCGACTATACGACAGAGCCCGTTGACACCGGGGTTACTCGAGA
  50  D  Y  S  I  D  T  D  Y  T  T  E  P  V  D  T  G  V  T  R  E 661 GTACTGGCTTGAGTTAACGGACGTAACCGTGTCGCCAGACGGGGTGTCGCGGTCAGCGAT
  70  Y  W  L  E  L  T  D  V  T  V  S  P  D  G  V  S  R  S  A  M 721 GGCTGTCAATGGCTCCATCCCTGGTCCAACCATCTTCGCTGACTGGGGTGATACCGTCGT
  90  A  V  N  G  S  I  P  G  P  T  I  F  A  D  W  G  D  T  V  V 781 CGTTCACGTCACCAACTCGTTATCCACTTCTCTGAACGGAACAAGCATCCACTGGCATGG
 110  V  H  V  T  N  S  L  S  T  S  L  N  G  T  S  I  H  W  H  G   Cu-binding 841 CATCCGCCAAAACTACACCAACCAGAACGACGGTGTTGCCTCCATTACGCAGTGTCCTCT
 130  I  R  Q  N  Y  T  N  Q  N  D  G  V  A  S  I  T  Q  C  P  L 901 GGCGGTTGGCGAATCAACCACCTACACCTGGAAAGCAACACAATATGGCTCATCTTGGTA
 150  A  V  G  E  S  T  T  Y  T  W  K  A  T  Q  Y  G  S  S  W  Y   Cu-binding 961 CCATTCTCACTTCAGCCTTCAGGCCTGGGAAGGCGTCTTTGGTGGGATCATCATCAATGG
 170  H  S  H  F  S  L  Q  A  W  E  G  V  F  G  G  I  I  I  N  G 1021 TCCTTCTACCGCCAACTATGACGAGGATCTTGGCATGCTTTTCCTCAATGATTGGGATCA
 190  P  S  T  A  N  Y  D  E  D  L  G  M  L  F  L  N  D  W  D  H 1081 CCAAACTGTCGATGAGCTCTATTCCAGTGCTGAAACCTCTGGGCCACCCACCTTGGCCAA
 210  Q  T  V  D  E  L  Y  S  S  A  E  T  S  G  P  P  T  L  A  N 1141 CGGTCTCATCAACGGTACGAACGTCTACGGGGAAGATGGTGATTCATCCCAGACCGGAAC
 230  G  L  I  N  G  T  N  V  Y  G  E  D  G  D  S  S  Q  T  G  T 1201 AAGATTGGCTGTCTCATTCACGTCTGGCACCTCATACCGCATGCGGCTGGTGAATGCCGC
 250  R  L  A  V  S  F  T  S  G  T  S  Y  R  M  R  L  V  N  A  A 1261 CGTCGACACGCATTGGAAATTCTCCATCGGCAACCACACAATGACTGTGATGGCCGCTGA
 270  V  D  T  H  W  K  F  S  I  G  N  H  T  M  T  V  M  A  A  D 1321 TCTCGTTCCGATTGAGCCATATGAAACGACGGTCTTAACAATTGGGATGGgtaagtacct
 290  L  V  P  I  E  P  Y  E  T  T  V  L  T  I  G  M  G 1381 acatcatcagaccacctacttattcggtttcttaggacacccgagactgagttccacata
                                                 intron 1 (71 bp)
```

Fig. 6D I

```
1441 gGACAAAGATACGACATAGTCGTCACGGCAGATCAAGCTGATGTCGCGGATAACTTCTGG
 307   Q  R  Y  D  I  V  V  T  A  D  Q  A  D  V  A  D  N  F  W

1501 ATGAGGGCTATCCCACAATCAGCATGCTCTGATAACGACAGCGCCGACAATATCAGAGGG
 326  M  R  A  I  P  Q  S  A  C  S  D  N  D  S  A  D  N  I  R  G

1561 ATCGTCTACTATGGTGATAGTCCCGGCACCCCTTCAACAACTGGCTACGACTTCGAGGAC
 346  I  V  Y  Y  G  D  S  P  G  T  P  S  T  T  G  Y  D  F  E  D

1621 GCCTGCGATGATGAGACGGCCAACATCACCCCTTACATCTCCAAGACGGTTTCTTCAGCA
 366  A  C  D  D  E  T  A  N  I  T  P  Y  I  S  K  T  V  S  S  A

1681 GAATGGAATGACTTGGAAACTGCCTCAGTCTCTAGGAACTCGGCCGGCCTTTTCAAATGG
 386  E  W  N  D  L  E  T  A  S  V  S  R  N  S  A  G  L  F  K  W

1741 TATCTCAACAGCACGACCATGCTAGTTGACTGGGCAAAACCCACTCTCGAGATGGTGACG
 406  Y  L  N  S  T  T  M  L  V  D  W  A  K  P  T  L  E  M  V  T

1801 GACAACGTGACCGAATACGATTCGGATGACGCCATCATTGAGCTGAATGAAGCCAACCAG
 426  D  N  V  T  E  Y  D  S  D  D  A  I  I  E  L  N  E  A  N  Q

1861 TGGGTGTACATGGTGGTTCAAACAACGCTCCAGGTTCCACACCCAATCCATCTGCACGGT
 446  W  V  Y  M  V  V  Q  T  T  L  Q  V  P  H  P  I  H  L  H  G    Cu-binding 1921 CACGATTTCTTCATTCTCGCCCAAGGTTCAGGGACATACGATTCGTCGACAGTAACATTG
 466  H  D  F  F  I  L  A  Q  G  S  G  T  Y  D  S  S  T  V  T  L 1981 AAGACGGATAACCCACCCAGACGCGACACGGCCATGCTGCCATCGCAGGGATACTTGGTC
 486  K  T  D  N  P  P  R  R  D  T  A  M  L  P  S  Q  G  Y  L  V 2041 ATGGCCTGGGAGACGGACAACCCTGGCGTTTGGCTGATGCACTGTCACATCGGTTGGCAT
 506  M  A  W  E  T  D  N  P  G  V  W  L  M  H  C  H  I  G  W  H    Cu-binding 2101 ACCTCAGAGGGCTTCGCCCTCCAGTTCATTGAGCGGAAGAGCGAGATCGCGTCGATCGTC
 526  T  S  E  G  F  A  L  Q  F  I  E  R  K  S  E  I  A  S  I  V 2161 AGTACGTCGACTATGAAAGATATTTGCACCAAGTGGGAGGAGTTTCAGGAGGAATATTCA
 546  S  T  S  T  M  K  D  I  C  T  K  W  E  E  F  Q  E  E  Y  S 2221 ATTGAACAAGAAGACTCTGGTGTATGAgatggatgtgcgttgaccattttgcgtcaaaga
 566  I  E  Q  E  D  S  G  V  *

2281 catcctgcctgtcggtaactctgatttgccgtgtgaacttggtttactaggtatttacag
2341 atacctacatcattggacatgtacataaggtacttaagtatccccgtatgcatctgtca
2401 tctgtcaagtcatcctcaaccgttctagcccatcatgcacgtatgtacatgaatgtaatg
2461 atggaacctagcacattagcaacagtttgcaaacgagtatcggcatggtcctaagagtca
2521 tgattaggggcagcgcaggttcgacttgttgtttatacagttaatcgtgcgccccggt
2581 tacatattatgtaccctgcttacacatccatatactaaggtgcttgaggtcgttgtac
2641 cgctgttgagctcctagcattcattccagggagcgtggcaatgactggtatgtctgtggg
2701 cgcgggcgtagatggtggggtgggagatatc
```

Fig. 6D II

*Ct lcc1* and the deduced amino acid sequence

```
  1 ttcccgaaggcttcaactcacactcggtcctcactccaaccaagcctgtcgtatacacga
 61 actcgtcccgcgtctaccgggcgaggttgctgcacctgccttgacgacattccgaatctg
121 ggaactaagacggcatcaccgtcgatatattggataggatccgagttttcgcgatctttg
181 ttgccttcactgaggagaaggtgcactctgggtgttgagtctgtcgtctatataacgacc
241 agaccttgcgacagtgagttgactccagttcttcatcgtcaccatcagcatcagacgctt
301 cagtgtcttgagcctcgttcttttaacaaatcgctcactcaatcatagttggcttggtgc
```

```
361 catcagcatcATGAAGTTCCTAACCTATGCCACCGCCCTCCTGGGTGCCCTTACAGCCGT
  1           M  K  F  L  T  Y  A  T  A  L  L  G  A  L  T  A  V
```

```
421 CGTAGGGGCAATCCCAACTCGTTCTGGCACCAAGAAAAAGTACATTAGAGATGGCCCCTGG
 18  V  G  A  I  P  T  R  S  G  T  K  K  K  Y  I  R  D  G  P  G    N-term. peptide
```

```
481 ACCCTGCCATACCCCAAGTAATCGGGCATGCTGGGCCCCTGGGTTCGACATCAATACTGA
 38  P  C  H  T  P  S  N  R  A  C  W  A  P  G  F  D  I  N  T  D
```

```
541 CTACGAAGTCAACACACCCAACACGGGTGTTACCCGCAATgtaagtcttcatcgttacta
 58  Y  E  V  N  T  P  N  T  G  V  T  R  N    intron 1 (50 bp)
```

```
601 gtgcagtgaatttcgtgctgacagaggtagTACACTCTCACTCTGACGGAGGAAGACAAC
 71                               Y  T  L  T  L  T  E  E  D  N    Peptide 18.9
```

```
661 TGGACCGGCCCGGATGGGGTGGTCAAGGAAAAGATTATGCTGGTTAATGgtatgtcagcc
 81  W  T  G  P  D  G  V  V  K  E  K  I  M  L  V  N  G
```

```
721 cctgagctaggtatgatatgatgactaaccatatatgtgcagGCAAAACTTTAGgtatgt
 98     intron 2 (53 bp)                              K  T  L  G
```

```
781 ctctcctggtgaagttaagctagatgatgtactaacctatgcagGCCCGACCATTGAGGC
102            intron 3 (50 bp)                       P  T  I  E  A
```

```
841 CAACTGGGGTGACTGGATCGAAGTCAAGGTCATCAATAACCTCTTGACTAATGGtatgt
107  N  W  G  D  W  I  E  V  K  V  I  N  N  L  L  T  N  G
```

```
901 cttgttcttccccctttagtggagtgcccaagctgactgactcccatagAACTTCCATCC
125        intron 4 (55 bp)                          T  S  I  H    Cu-binding
```

```
961 ACTGGCACGGCATTCACCAGAAGGGCAGTAACCTTCACGACGGTGCCAACGGCGTTACTG
129  W  H  G  I  H  Q  K  G  S  N  L  H  D  G  A  N  G  V  T  E
```

```
1021 AATGCCCCATCCCTCCCAACGGTGGCCAGCGCACCTATCGCTTCCGTGCCCAGCAGTATG
149   C  P  I  P  P  N  G  G  Q  R  T  Y  R  F  R  A  Q  Q  Y  G
```

```
1081 GCACCAGCTGGTACCACTCTCACTTCTCTGCTCAGTATGGCAATGGCATCGTCGGTCCCA
169   T  S  W  Y  H  S  H  F  S  A  Q  Y  G  N  G  I  V  G  P  I    Cu-binding
```

```
1141 TCGTTATCCACGGTCCAGCTTCTCTGCCCTATGACATCGACCTTGGCCCCTTCCCTCTTA
189   V  I  H  G  P  A  S  L  P  Y  D  I  D  L  G  P  F  P  L  T
```

```
1201 CGGACTACTACTACAAGAGCGCGGATGAGCTGGTGCGCCACACTCAGAACAACGGCCCAC
209   D  Y  Y  Y  K  S  A  D  E  L  V  R  H  T  Q  N  N  G  P  P
```

```
1261 CGTTCAGCGACAACGTCCTCTTCAACGGCACCGGCGTTCATCCCCAGACTGGCCATGGTC
229   F  S  D  N  V  L  F  N  G  T  G  V  H  P  Q  T  G  H  G  Q
```

```
1321 AGTATGCTAAGGTGACCCTGACCCCGGGCAAGCGTCACCGCCTGCGCATCATCAACATGT
249   Y  A  K  V  T  L  T  P  G  K  R  H  R  L  R  I  I  N  M  S
```

```
1381 CGACGGAGAACCACTTCCAGGTCTCTCTCGTCGGCCACCAGTTCACCGTCATTGCCGCTG
269   T  E  N  H  F  Q  V  S  L  V  G  H  Q  F  T  V  I  A  A  D
```

Fig. 6E I

```
1441 ACATGGTCCCCGTCCACTCCTACACTACTGACAGCCTGTTTCTCGCTGTCGGGCAGCGTT
 289   M  V  P  V  H  S  Y  T  T  D  S  L  F  L  A  V  G  Q  R  Y

1501 ATGATGTCACCATCGACGCTTCGCAGACCCCCGGTAACTACTGGTTCAACGTCACCTTTG
 309   D  V  T  I  D  A  S  Q  T  P  G  N  Y  W  F  N  V  T  F  G

1561 GCGGCGGTTTCGCTTGCGGTGGTTCCTTCAACCCTAACCCAGCTGCCATCTTCCACTATG
 329   G  G  F  A  C  G  G  S  F  N  P  N  P  A  A  I  F  H  Y  E

1621 AGGGTGCCCCCGATGCTCTGCCGACTGACCCTGGTGTTCCTCCGCGCGACCACAACTGCT
 349   G  A  P  D  A  L  P  T  D  P  G  V  P  P  R  D  H  N  C  L   Peptide 22.4

1681 TGGACACTCTGGATCTCGTCCCTGTCGTACCTCGTAATGTTCAGGTCAACCAGTTCGTCA
 369   D  T  L  D  L  V  P  V  V  P  R  N  V  Q  V  N  Q  F  V  K

1741 AGAAGCCTGAGAACACCCTGCCTGTTGAGCTGTCCCTTGGTGGTACCCCGCTCTTCGTTT
 389   K  P  E  N  T  L  P  V  E  L  S  L  G  G  T  P  L  F  V  W   Peptide 22.7

1801 GGAAGGTCAACGGCAGCGCCATTGATGTTGACTGGGGCAACCCCGTCCTTCAGTATGTGA
 409   K  V  N  G  S  A  I  D  V  D  W  G  N  P  V  L  Q  Y  V  M

1861 TGGACCGCAACACCAGCTACCGCCAAGCCGACAACATCGTCGAGGTTAATGGTGTCAACC
 429   D  R  N  T  S  Y  R  Q  A  D  N  I  V  E  V  N  G  V  N  Q

1921 AGTGGACTTACTGGCTGATTGAGAACGACCCCAATGGTGCCTTCAGCCTGCCCCACCCCA
 449   W  T  Y  W  L  I  E  N  D  P  N  G  A  F  S  L  P  H  P  M   Cu-binding 1981 TGCATCTTCACgtaagttatttccctctttctcttttacctaccccctttattgcagat
 469   H  L  H                      intron 5 (95 bp)

2041 tagtcccttctttagcccatatctcagataactaacctccttccagGGCCACGACTTCCT
 472                                                    G  H  D  F  L 2101 CATTGTCGGCCGCTCCCCCGACGTCCCGCCGGGCTCGAACCAGCGCTACAACTTCGACCC
 477   I  V  G  R  S  P  D  V  P  P  G  S  N  Q  R  Y  N  F  D  P 2161 CGCCACCGACATCTACCGCCTGCGCGGTCAGAACCCCGACCCGTCGTGACGTCGCCATGCT
 497   A  T  D  I  Y  R  L  R  G  Q  N  P  T  R  R  D  V  A  M  L 2221 TCCTGCCGGCGGCTGGCTGCTGCTCGCCTTCCTCACCGACAACCCCGGTGCCTGGCTCTT
 517   P  A  G  G  W  L  L  L  A  F  L  T  D  N  P  G  A  W  L  F 2281 CCACTGCCACATTGCTTGGCACGTGTCGGGCGGTCTGTCTGTCGACTTCCTCGAGCGGCC
 537   H  C  H  I  A  W  H  V  S  G  G  L  S  V  D  F  L  E  R  P   Cu-binding 2341 GAACGACCTGCGCAACAGCATCCTCCAGCATGATAAGGACGAGTTCAACCGCGTGTGCAA
 557   N  D  L  R  N  S  I  L  Q  H  D  K  D  E  F  N  R  V  C  N 2401 TGAGTGGCGCACGTACTGGCCTAATAGTCCCCATCCTAAGATTGACTCTGGTTTGAAGCA
 577   E  W  R  T  Y  W  P  N  S  P  H  P  K  I  D  S  G  L  K  H 2461 CCGCTGGGTTGAGGAGAGTGAGTGGCTGGTTCGATAGggggtgttgtgcagagttggggt
 597   R  W  V  E  E  S  E  W  L  V  R  *

2521 gtgatttgggtcatggttttgagcgttgggatatgggcgttgataatcattaatgtgtt
2581 ttggttgggcatatttcggagtttttggctatcggttatcgtagtggtcaatagtagtcaa
2641 cccttctctatcgtcaatagtaatcaacccttctctacacaatttgatatcgtgacgttg
2701 atgacttgggactgaaggccaaacttaagttgggcatttttccggctcttttcctcatg
2761 tgataggtaaatgagcctagtttgaactatgtgtgctgttcagcactcactgcactatgt
2821 acagccaagatgtccccaagtgttcgatatgtcaagttccagcattgacgatcagctctc
2881 tatgttatcacttttgcactcgcttttttatgctaatgtcctctaccactgaaaatccct
2941 agccctgccaccgg
```

Fig. 6E II

Ct lcc2 and the deduced amino acid sequence

```
  1 tctagaagatatcggcagtcgcggtagcttgaatcatgagcggggatatacgagagaggg
 61 agcagcccctcgggtaacatgcggatgagaacatggcagcatcatcgattcctacgtcta
121 tatcttggagacgtataagaggaagtggtgatgacgataatcgtggagatctactgaccg
181 ctctctcacggcatattatgaattcgtgactttatccctctctgacgtggtttctgacaa
```

```
241 ctgccATGCCCAGACGTAGTCTCATACTCCTTCTCCTCGCCTTCCTTGGGCTCCTACACT
  1      M  P  R  R  S  L  I  L  L  L  L  A  F  L  G  L  L  H  L
```

```
301 TAACCCTAGCAAACCCCATCAAGGCAAACCCAAACCCCTTCCTCCTAGCCAGACAAACCA
 20   T  L  A  N  P  I  K  A  N  P  N  P  F  L  L  A  R  Q  T  I
```

```
361 TCACCCCTGGAGGCCAGCCCTGTGGCCAACATGGCCCAGAGAACAGACTCTGTTGGCGAA
 40   T  P  G  G  Q  P  C  G  Q  H  G  P  E  N  R  L  C  W  R  N
```

```
421 ACCTTTGGAATATCAGTACTGATCCGGACGTCAGCATCCCCCCTGCCTACAACAATCGAT
 60   L  W  N  I  S  T  D  P  D  V  S  I  P  P  A  Y  N  N  R  Y
```

```
481 ATgtaagtctcctcaagcctctgaatactagtcgtcactgacatcatccagTATGATTTG
 80                   intron 1 (49 bp)                  Y  D  L
```

```
541 CACATCACCAATGAGACAAACTGGCTAGGGCCAGACGGCGTGCGGAAGCACGCTATGCTC
 83 H  I  T  N  E  T  N  W  L  G  P  D  G  V  R  K  H  A  M  L
```

```
601 ATCAACAgtcagtcccccttggccgtgaccccctcccttatcttctgtcagagggctaac
103 I  N  N               intron 2 (61 bp)
```

```
661 aaccccagATCAATTTCCCGGCCCTACCATTGAAGCAGAATGGGGTGACTATATCGTAGT
106          Q  F  P  G  P  T  I  E  A  E  W  G  D  Y  I  V  V
```

```
721 GAATGTCTACAATGACCTGGAGGACAACGGgtaagcctctcttcctcatttgggctactc
123 N  V  Y  N  D  L  E  D  N  G              intron 3 (79 bp)
```

```
781 gcctaacaccgtcaacaacttaccoctcactaccgctgactccatccagGACATCCATCC
133                                                  T  S  I  H   Cu-binding
```

```
841 ATTGGCATGGCATCCGCCAATTCGGCGAAAGCAACCAAGATGGCACCAATGGCGTCACCG
137 W  H  G  I  R  Q  F  G  E  S  N  Q  D  G  T  N  G  V  T  E
```

```
901 AGTGCCCCATTCCACCGGGGCACATGAAAACATACAGTTTCCACGTCACTCAGTACGGAA
157 C  P  I  P  P  G  H  M  K  T  Y  S  F  H  V  T  Q  Y  G  T
```

```
961 CGTCCTGGTACCACAGCCACTTCTCCAACCAGTACGGCAACGGCGTGCTCGGCGCACTGG
177 S  W  Y  H  S  H  F  S  N  Q  Y  G  N  G  V  L  G  A  L  V   Cu-binding
```

```
1021 TGGTCAAAGGCCCGGCTTCCGCCAACTACGACATCGACCTCGGCCCGTACATCATTAGCG
 197 V  K  G  P  A  S  A  N  Y  D  I  D  L  G  P  Y  I  I  S  D
```

```
1081 ACTACTACCACGAGACGGCCGACAGATTACATCTCCAGGCAGAGCTACTCCGCAACGGGC
 217 Y  Y  H  E  T  A  D  R  L  H  L  Q  A  E  L  L  R  N  G  P
```

```
1141 CCCCTCCAGACAGCGACAACATCCTCTTCAGGGGCAAGAACATCAACCCTGACGGCTCGG
 237 P  P  D  S  D  N  I  L  F  R  G  K  N  I  N  P  D  G  S  G
```

```
1201 GCCGCGGCTCTTATGACCGATTAACCCTCATCCCAGGCAAGAAACACCTGCTGCGTCTGA
 257 R  G  S  Y  D  R  L  T  L  I  P  G  K  K  H  L  L  R  L  I
```

```
1261 TCAACGCAAGCGTGGATAACTCCTTCACGGTCTCCCTCGTGGGACACAACTTCACGGTCA
 277 N  A  S  V  D  N  S  F  T  V  S  L  V  G  H  N  F  T  V  I
```

Fig. 6F I

```
1321 TTGCGACCGATATGGTCCCGGTCCAGCCAACCGTCCGCAGGAGCCTGTTCATGGCCGTCG
 297   A  T  D  M  V  P  V  Q  P  T  V  R  R  S  L  F  M  A  V  G

1381 GCCAGCGTTATGATGTTATTGTTACCGCCGACCAGCCCGTAGATAATTATTGGCTGAACG
 317   Q  R  Y  D  V  I  V  T  A  D  Q  P  V  D  N  Y  W  L  N  V

1441 TCACCCTGGAAGCAAACAACAACTGCGGCCGCTCTCGCAACCCCTACCCAGCAGCCATCA
 337   T  L  E  A  N  N  N  C  G  R  S  R  N  P  Y  P  A  A  I  I

1501 TCCACTACGAGGGAGCCAGCCCAACCGCCCTCCCCACCAACCGTGGCACCCCCCTCGTAG
 357   H  Y  E  G  A  S  P  T  A  L  P  T  N  R  G  T  P  L  V  A

1561 CAACCTGCACCGGCGAGACAGGCTTCACCCCCGTCGTGCCGCGGAATATCCCCCCCAACT
 377   T  C  T  G  E  T  G  F  T  P  V  V  P  R  N  I  P  P  N  F

1621 TCTTCCGCCCTTCCGACATCGCCTCCAATACCCTGCCAATCGGCCTCAACATTGTCAACC
 397   F  R  P  S  D  I  A  S  N  T  L  P  I  G  L  N  I  V  N  H

1681 ACACCACTAAAGGCCAAATCTTCTCCTGGCATGTGAAGAACACGCCTATTTCCGTGGAAT
 417   T  T  K  G  Q  I  F  S  W  H  V  K  N  T  P  I  S  V  E  W

1741 GGGGGCATCCAGTATTAGAGTACATCCTCGAAGGGAATTACTCCTTTCCCGCAGCGGTTA
 437   G  H  P  V  L  E  Y  I  L  E  G  N  Y  S  F  P  A  A  V  N

1801 ATCTGATTCAACTCAACCAAAAAGACACCTGGACACTCTTTTTGGTGCATAGTTCGTTAT
 457   L  I  Q  L  N  Q  K  D  T  W  T  L  F  L  V  H  S  S  L  S

1861 CATTACCGCACCCAATCCACCTCCACGGACACGACTTCCTCGTCCTGGGCCTGGGCAGCG
 477   L  P  H  P  I  H  L  H  G  H  D  F  L  V  L  G  L  G  S  G   Cu-binding 1921 GCACCTTTGATCCTCAGACACATCTCCCCTTGCTAAACTACTCAAACCCCGTCCGGCGAG
 497   T  F  D  P  Q  T  H  L  P  L  L  N  Y  S  N  P  V  R  R  D 1981 ACGTTGAACAGCTCCCCGGCTTGGGGTGGGCCGCCATCGCGTTCAAGACGGATAACCCGG
 517   V  E  Q  L  P  G  L  G  W  A  A  I  A  F  K  T  D  N  P  G 2041 GCGTGTGGCTCATGCACTGCCATATTGGGTGGCATGTGGCGATGGGGCTGGGGGTGCAGT
 537   V  W  L  M  H  C  H  I  G  W  H  V  A  M  G  L  G  V  Q  F   Cu-binding 2101 TTTTGGAGAGAGCGAGCGAGATGAGGGTGCTGATGAAGCTGGATCAGGTGGTGCCGAATT
 557   L  E  R  A  S  E  M  R  V  L  M  K  L  D  Q  V  V  P  N  C 2161 GTAACGCGTGGAGGGAGTACGAACGGGTGGGGAATTGGTTGCCTAGGGGGGATACGGATT
 577   N  A  W  R  E  Y  E  R  V  G  N  W  L  P  R  G  D  T  D  S 2221 CGGGGTTGTGAgggggtgaagagtgaggatgggcggacggtagacgtctggttatcagcc
 597   G  L  *

2281 tggggatcgcatcatggccggtagatcctttcatcttggatccgcttatgttgtcatttg
2341 actgggatgctgcgcagtagaggctgagctctgttaacgccagtgtgtaaaactcagcag
2401 agtgccatttgaggcattgtgagatgttcggaccactatcacacaccttaacattcgat
2461 agccttacgttaaggtgcttgatcatggcctgaggatgtcgtcaccattgttccca
```

Fig. 6F II

Cf lcc3 and the deduced amino acid sequence

```
   1 ccgcggctgatactaccagaaaacgcccagttacacatatacacgccgggaatctctgt
  61 acaggttgtctcaactgtgtcggttccgctcctgggaacgacattagcaccacctcttg
 121 agccgtcataatatcttcttcttcttttccccgtgctacgcaatccagacaacctg
 181 gcaaagatgcctattgagagctggaaactgccagatggcaacgctgaccggcgatca
 241 tctgtcgagacagcattaacgctcaacagccaccggcaaccatcccctagacactgccaac
 301 ttgctgccgtgtgcctgcactacatgtggcgtgacatggatacgatgttctggatatc
 361 cagaaagcttcatccgccgataggtctgctatctctctcttttctgccctttctgtctt
 421 ttccaggacccctaaaattttcatatgctctcacatcggggccagcatatctattccatg
 481 tctcccggttccatggtcttcatcacccgtcacagattctgtccttctgttattgcttc
 541 ttactggcagagtgtgtggcttgtggtgaaagaccacctgctgcccttcctagccatc 601 ATGXXGTCATTTTGGAXGATTTAACAACATTGCGTCCGTXGTAGAGCXGXCTCTCAGT   
   1  M  X  V  I  L  E  D  L  N  N  I  A  S  V  V  E  Q  X  L  S 661 ACCGTTGTAGAGAAGGTCACCTTCGCCCTATCACAGCTXGACACTAAXCgtacgtcagt
  21  T  V  V  E  K  V  T  S  A  L  S  Q  L  D  T  N  X 721 gacaggtccactcccttgaatgtacgacctaactcagctatgtagATACTTCGATCTG
  38           intron 1 (58 bp)                    Y  S  I  W 781 GXGAACTTTTGCTTGCCTCCTCATTGGCTCCCTTTTTGACAGATAACCGCTGCCTGATGG
  42  G  T  L  L  A  S  L  A  F  F  L  T  D  N  P  L  P  D  G 841 ATATCCATGGXGGCAACTTGACTGACTACGGCAACAACCXTTATCGTGAATGTCCACATAC
  62  Y  P  N  G  N  L  T  D  Y  N  N  P  Y  R  E  C  F  H  T 901 CGGCATTACTAGATCCTATCACTTCACCATCAGTCGXXXAGTCATTGCTCCAGATGGCTA
  82  G  I  T  R  S  Y  H  F  T  I  S  R  G  V  I  A  P  D  G  Y 961 CGAACGGAGGTGCTCCTTGTGAACGGGGCCTTCCCGGGACCACTTATTGAAGCAAATTG
 102  E  R  S  V  L  L  V  N  G  A  F  P  G  P  L  I  E  A  N 1021 GGGAGACACCATCATCGTGAAAGTTTTCAACAATATATCAAACCCCGAAGAGGCCACCTC
 122  G  D  T  I  I  V  K  V  F  N  N  I  S  N  P  E  G  T  S 1081 CATACACTGGCACGGCTTCCTCCAGCACCACACTCCTTGGGAAGATGGCACTCCTTGCAT    Cu-binding
 142  I  X  X  G  F  L  Q  H  H  T  P  W  E  D  G  T  P  G  I 1141 CACCCAATGTCCCATCCCCTCCGGAAAAGCTTACACCTACAAGTTCAACGCCAGTCTGTA
 162  T  Q  C  P  I  P  S  G  K  A  Y  T  Y  K  F  N  A  S  L  Y 1201 CGGTACAACCTGGTATCATGCCCATTACTCAGCCCAATATGCTGGTGGCATTGTTGGCC    Cu-binding
 182  G  T  T  X  X  X  X  X  Y  S  A  Q  Y  A  G  G  I  V  G  P 1261 TATTGTTATCCATGGACCAACCAAAGAAGGCTATGATATTGATGTCGGTCCTGTCATGCT
 202  I  V  I  R  G  P  T  K  E  G  V  D  I  D  V  G  P  V  M  L 1321 GGGTGgtaagctctatccgaccgggagatgactggcaactagatgtcacgaagactcata
 222  G  D                      intron 2 (85 bp)

1381 acttccacagATTGGTATCACCAACAATACTACAATATCGTCAAGACAATGCTAAGCCCC
 224            N  W  Y  H  Q  E  Y  Y  N  I  V  K  T  M  L  S  P 1441 AGCGAAAGTCCTCTCCGXGTTTATTCCGACAACAACCTCATCAACGGAAGATGGACTTC
 240  S  E  S  P  L  R  V  Y  S  D  N  N  L  I  N  G  K  M  D  F 1501 AACTGTTCGACCGTCTCTGAAGACGACCCGCACTGATGCACAGCAAACGCGGGATATCC
 260  N  C  S  T  V  S  E  D  D  P  H  C  T  P  N  A  G  I  S 1561 AAATTCCGCTTCCAGGCCGGTCAGGTTCATCCGCTTGCGCCTCATCAACCTAGCGGCGAC
 280  K  F  P  F  Q  A  G  Q  V  R  R  L  R  L  I  N  L  G  G  D
```

Fig. 6G I

```
1621 GGTATCCAGCGCTTCTCCATAGATGAGCACGTCCTAACCGTCATCGCCGAGGACTTTGTG
 309  G  I  Q  R  F  S  I  D  E  H  V  L  T  V  I  A  E  D  F  V

1681 CCGGTCAAGCCGTACAACACGACAGTGGTAGTGCTGGGCGTCGGCAGCGCGCTGATCTT
 329  P  V  K  P  Y  N  T  T  V  V  V  L  G  V  G  G  Q  A  D  V

1741 TTGGTGACTGCCAATGCCGGAGGGCCCAAGTCTACGTTCTGGATGCGCTCCAGCCTCACG
 340  L  V  T  A  N  A  G  G  P  K  S  T  F  W  M  R  S  S  L  T

1801 ACATGCTCGCCGGCCAGGCAGCCGAACGCTGTCGCTGTTGTGTTGTATGATGAGGCGGAC
 360  T  C  S  P  A  R  Q  P  N  A  V  A  V  V  L  Y  D  E  A  D

1861 GAGAATGCCGTGCCGAATAGCAAGCCGTGGAGATACCGAATCCTGATGTGTGCTAAT
 380  E  N  A  V  P  N  S  K  P  W  E  I  P  N  P  D  V  C  A  N

1921 CTGCCGCTGGAGATCACCGAGCCACTGTACCCAATTCCGCTGCCTGAGCCGACCTTTACA
 400  L  P  L  E  I  T  E  P  L  Y  P  I  P  L  P  E  P  T  F  T

1981 GAGAATGGAGATCGAGATCTTCAAAAATGAGTCCAAGATTTGGCTGTGGAAGTTCAAT
 420  E  N  G  D  R  D  L  Q  K  M  E  S  K  I  W  L  W  K  F  N

2041 GATATATCAATGCGGACGCATTACAACAAGCCGGTGCTGCTGCTGGCCAACCAAGGAGAA
 440  D  I  S  M  R  T  H  Y  N  K  P  V  L  L  A  N  Q  G  E

2101 TATGACTACCCCGAAGAATGGAACGTCGTGAACTACTATCAAAACGAGTCCGTCCGAATT
 460  Y  D  Y  P  E  E  W  N  V  V  N  Y  Y  Q  N  E  S  V  R  I

2161 GTTGTGAAAAACAACTCTCCTACCCCgtaggtatacctcagaggaatcttctgctcttgt
 480  V  V  K  N  N  S  P  T  P       intron 3 (69 bp)

2221 tgtccgcataccatgactaaccccctgactcaacagCCACCCGATGCATCTCCACCGGCCAC
 489                                      P  M                    Cu-binding 2281 AACTTTTACATCCTCCACGAGGGCCCCGGCGACTGGGATGGCACCATGGTCCGGCCAAGC
 497  N  F  Y  I  L  H  E  G  P  G  D  W  D  G  T  M  V  R  P  S 2341 AACCCCCACAGAGACGTGGACGTCTACCTGGTACGCGGGTTTGGTCATCTTGTTCTGCAATTC
 517  N  P  H  R  D  V  Y  L  V  R  G  F  G  H  L  V  L  Q  P 2401 GATGGTGAACCTGGTACGTGTGCCGTAGTTCTCAGCCAGACTCCGTGTGCCGCTTGGAGGA
 537  D  G  E  P  G  T  C  A  V  V  L  S  Q  T  P  C  A  L  G  G 2461 AGGCAATCTAACAACATAATAGGAGTCTGGGCCTTCCACTGCCATATTGCATGGCACGCA
 557  R  Q  S  N  N  I  I  G  V  W  A  F                 A       Cu-binding 2521 TCGGGTGGTTTTTAGCGACGCTTATTGTCCAGCCCGATACGGTTGAGAAATTCAACGTT
 577  S  G  G  F  L  A  T  L  I  V  Q  P  D  T  V  E  K  F  N  V 2581 CCGGAGGATGTGTGGAATAACTGCAACGCGTGGGATCACTACACAAAGCATAACGTTGTT
 597  P  E  D  V  W  N  N  C  N  A  W  D  H  Y  T  K  H  N  V  V 2641 GAGCAGATTGACAGTGGTACATAAttttaggttcgttcgttggccgagtgcggcagct
 617  E  Q  I  D  S  G  T  *

2701 gataggacacggtttaaattccccgtcggaataatgtcgatgtagttttgcatatatac
2761 tcatcgttgatggagactcacagtcaacactcgaaattggatcgtaatacatggcagttt
2821 gtgcacagccaaattgcacgaaaatgtgcttattgagcgaccgtgggcattatatcattc
2881 aagaagcaaacaactgtacatggcacgtacgtactgtcaaggagtcgatacatgcatcat
2941 aaaccgaatatccaggccaaggtattcaagcaaaaatgatagacagtccgtgagtctgagt
3001 ccagtccaaacccgagtccaagctt
```

Fig. 6G II

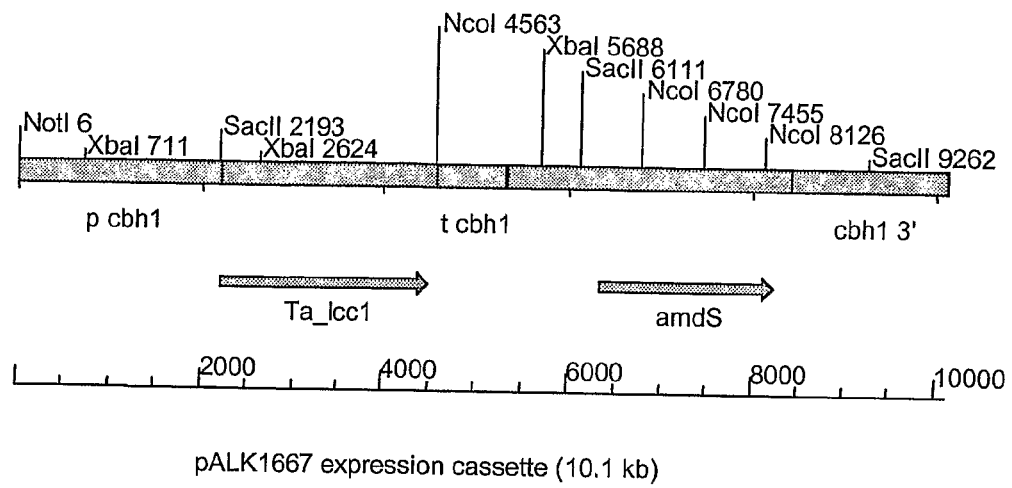
pALK1667 expression cassette (10.1 kb)
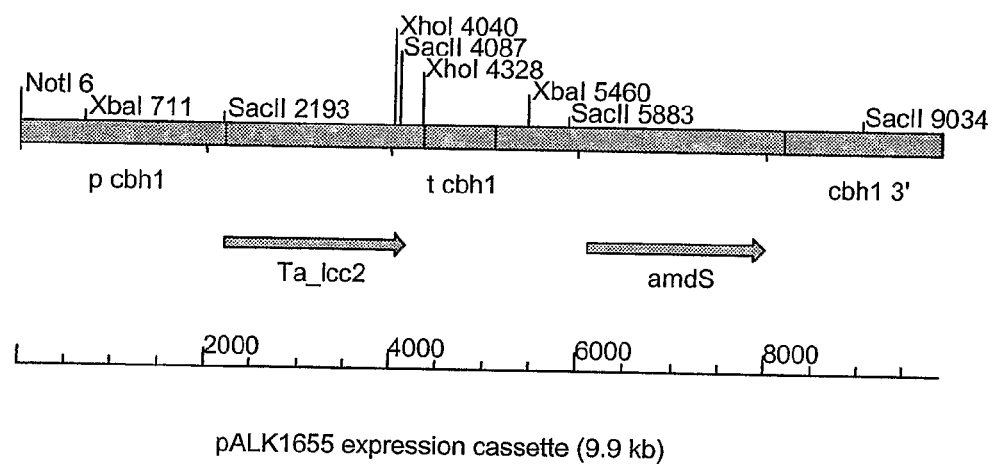
pALK1655 expression cassette (9.9 kb)
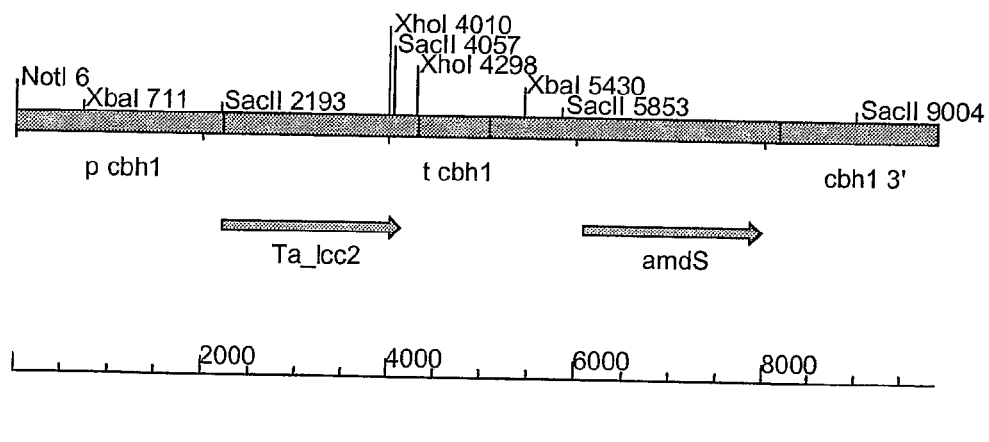
pALK1656 expression cassette (9.9 kb)
Fig. 7A

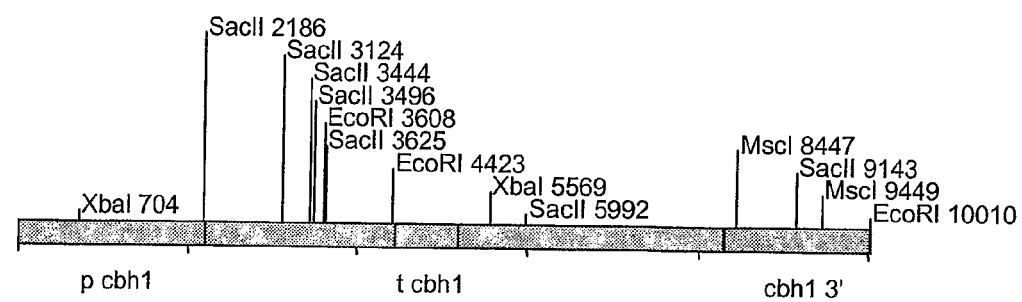
pALK1671 expression cassette (10.0 kb)
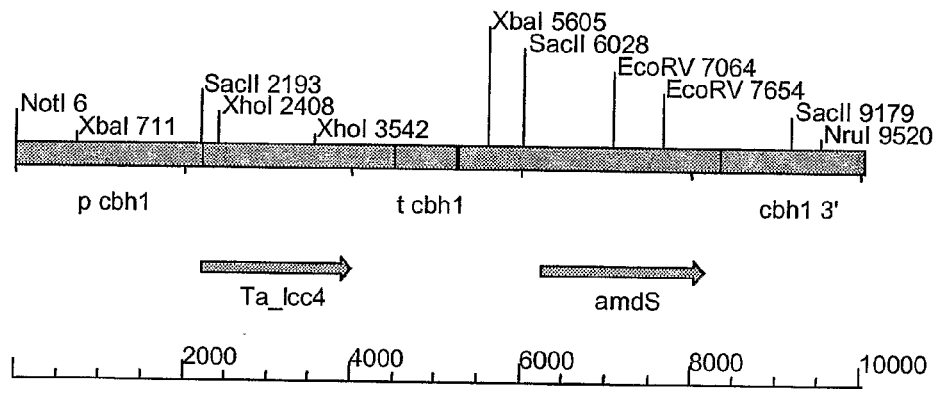
pALK1684 expression cassette (10.0 kb)
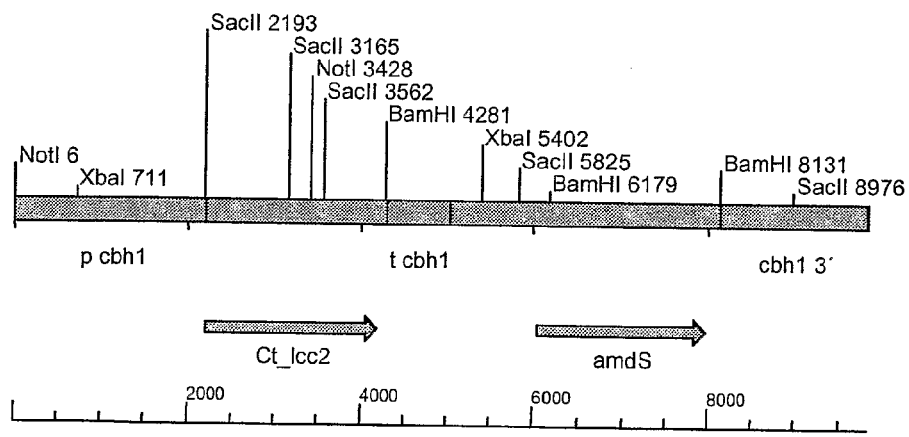
pALK1340 expression cassette (9.8 kb)
Fig. 7B

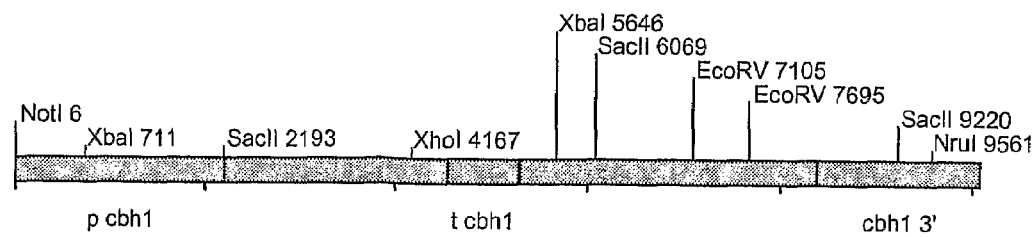
pALK1321 expression cassette (10.1 kb)
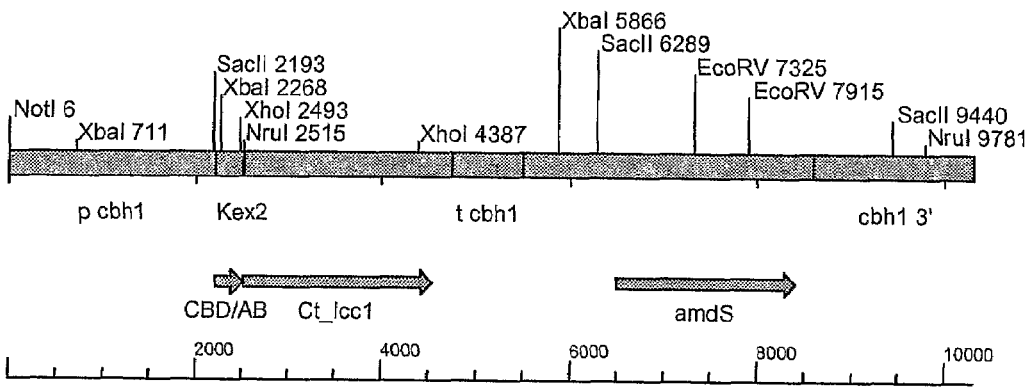
pALK1326 expression cassette (10.3 kb)
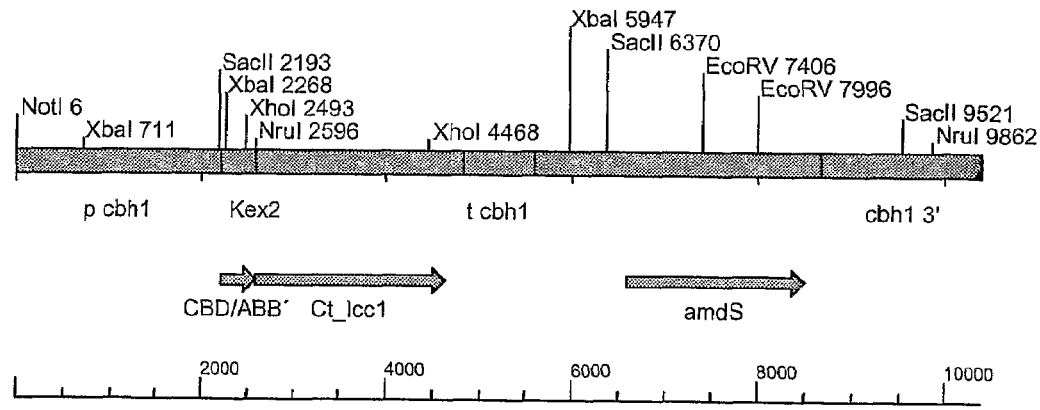
pALK1326 expression cassette (10.4 kb)
Fig. 7C

SEQUENCE LISTING

```
<160> NUMBER OF SEQ ID NOS: 51

<210> SEQ ID NO 1
<211> LENGTH: 19
<212> TYPE: PRT
<213> ORGANISM: Thielavia arenaria ALKO4197
<220> FEATURE:
<221> NAME/KEY: MISC_FEATURE
<222> LOCATION: (1)..(19)
<223> OTHER INFORMATION: Sequence of Peptide 1, a tryptic peptide from
      Thielavia arenaria ALKO 4197 Ta Lcc1 protein
<220> FEATURE:
<221> NAME/KEY: MISC_FEATURE
<222> LOCATION: (12)..(12)
<223> OTHER INFORMATION: Xaa can be Gln or Ile

<400> SEQUENCE: 1

Tyr Gln Gly Ala Pro Asn Thr Leu Pro Thr Asn Xaa Gly Leu Pro Val
1               5                   10                  15

Pro Asn His

<210> SEQ ID NO 2
<211> LENGTH: 11
<212> TYPE: PRT
<213> ORGANISM: Thielavia arenaria ALKO4197
<220> FEATURE:
<221> NAME/KEY: MISC_FEATURE
<222> LOCATION: (1)..(11)
<223> OTHER INFORMATION: Sequence of Peptide 2, a tryptic peptide from
      Thielavia arenaria ALKO 4197 Ta Lcc1 protein

<400> SEQUENCE: 2

Glu Asn Trp Ile Gly Pro Asp Gly Val Leu Lys
1               5                   10

<210> SEQ ID NO 3
<211> LENGTH: 9
<212> TYPE: PRT
<213> ORGANISM: Thielavia arenaria ALKO4179
<220> FEATURE:
<221> NAME/KEY: UNSURE
<222> LOCATION: (1)..(1)
<223> OTHER INFORMATION: First amino acid is unsure
<220> FEATURE:
<221> NAME/KEY: MISC_FEATURE
<222> LOCATION: (1)..(9)
<223> OTHER INFORMATION: Sequence of Peptide 3, a tryptic peptide from
      Thielavia arenaria ALKO 4197 Ta Lcc1 protein

<400> SEQUENCE: 3

Ser Leu Phe Leu Ala Val Gly Gln Arg
1               5

<210> SEQ ID NO 4
<211> LENGTH: 20
<212> TYPE: PRT
<213> ORGANISM: Chaetomium thermophilum ALKO4265
<220> FEATURE:
<221> NAME/KEY: MISC_FEATURE
<222> LOCATION: (1)..(20)
<223> OTHER INFORMATION: N-terminal sequence from Chaetomium
      thermophilum ALKO4265 CtLcc1 protein
<220> FEATURE:
<221> NAME/KEY: MISC_FEATURE
<222> LOCATION: (1)..(20)
<223> OTHER INFORMATION: N-terminal sequence from Chaetomium
      thermophilum ALKO4265 CtLcc1 protein
<220> FEATURE:
<221> NAME/KEY: MISC_FEATURE
```

```
<222> LOCATION: (1)..(20)
<223> OTHER INFORMATION: Xaa can be Glu, Ala or Asp

<400> SEQUENCE: 4

Xaa Gly Pro Gly Pro Cys His Thr Pro Ala Asn Tyr Ala Cys Trp Ala
1               5                   10                  15

Pro Gly Phe Asp
            20

<210> SEQ ID NO 5
<211> LENGTH: 15
<212> TYPE: PRT
<213> ORGANISM: Chaetomium thermophilum ALKO4265
<220> FEATURE:
<221> NAME/KEY: MISC_FEATURE
<222> LOCATION: (1)..(15)
<223> OTHER INFORMATION: Sequence of Peptide 18.9, a tryptic peptide
      from Chaetomium thermophilum ALKO 4265 Ct Lcc1 protein

<400> SEQUENCE: 5

Leu Thr Glu Asn Asp Asn Trp Thr Gly Pro Asp Gly Val Val Lys
1               5                   10                  15

<210> SEQ ID NO 6
<211> LENGTH: 16
<212> TYPE: PRT
<213> ORGANISM: Chaetomium thermophilum ALKO4265
<220> FEATURE:
<221> NAME/KEY: MISC_FEATURE
<222> LOCATION: (1)..(16)
<223> OTHER INFORMATION: Sequence of Peptide 22.4, a tryptic peptide
      from Chaetomium thermophilum ALKO4265 Ct Lcc1 protein

<400> SEQUENCE: 6

Asp His Asn Cys Leu Asp Leu Leu Asp Leu Val Pro Val Val Pro Arg
1               5                   10                  15

<210> SEQ ID NO 7
<211> LENGTH: 11
<212> TYPE: PRT
<213> ORGANISM: Chaetomium thermophilum ALKO4265
<220> FEATURE:
<221> NAME/KEY: MISC_FEATURE
<222> LOCATION: (1)..(1)
<223> OTHER INFORMATION: Xaa may be Thr or Ser
<220> FEATURE:
<221> NAME/KEY: MISC_FEATURE
<222> LOCATION: (7)..(7)
<223> OTHER INFORMATION: Xaa may be Thr or Leu
<220> FEATURE:
<221> NAME/KEY: MISC_FEATURE
<222> LOCATION: (10)..(10)
<223> OTHER INFORMATION: Xaa may be any naturally occuring aminoacid
<220> FEATURE:
<221> NAME/KEY: MISC_FEATURE
<222> LOCATION: (10)..(10)
<223> OTHER INFORMATION: Xaa  unsure; may be any naturally occuring
      aminoacid

<400> SEQUENCE: 7

Xaa Leu Gly Gly Thr Pro Xaa Phe Val Xaa Lys
1               5                   10

<210> SEQ ID NO 8
<211> LENGTH: 17
<212> TYPE: DNA
<213> ORGANISM: artificial
<220> FEATURE:
<223> OTHER INFORMATION: Sequence of the oligonucleotide primer POX1
<220> FEATURE:
```

-continued

```
<221> NAME/KEY: misc_feature
<222> LOCATION: (9)..(9)
<223> OTHER INFORMATION: n can be c or i

<400> SEQUENCE: 8
aaytaygcnt gytgggc                                                  17

<210> SEQ ID NO 9
<211> LENGTH: 17
<212> TYPE: DNA
<213> ORGANISM: artificial
<220> FEATURE:
<223> OTHER INFORMATION: Sequence of the oligonucleotide primer POX2
<220> FEATURE:
<221> NAME/KEY: misc_feature
<222> LOCATION: (9)..(9)
<223> OTHER INFORMATION: n can be c or i

<400> SEQUENCE: 9
gcccarcang crtartt                                                  17

<210> SEQ ID NO 10
<211> LENGTH: 32
<212> TYPE: DNA
<213> ORGANISM: artificial
<220> FEATURE:
<223> OTHER INFORMATION: Sequence of the oligonucleotide primer POX22

<400> SEQUENCE: 10
tgccayacsc ccgcyaacta cgcytgctgg gc                                 32

<210> SEQ ID NO 11
<211> LENGTH: 17
<212> TYPE: DNA
<213> ORGANISM: artificial
<220> FEATURE:
<223> OTHER INFORMATION: Sequence of oligonucleotide primer POX3

<400> SEQUENCE: 11
gtccarttrt crttytc                                                  17

<210> SEQ ID NO 12
<211> LENGTH: 17
<212> TYPE: DNA
<213> ORGANISM: artificial
<220> FEATURE:
<223> OTHER INFORMATION: Sequence of the oligonucleotide primer POX16

<400> SEQUENCE: 12
garaaygaya aytggac                                                  17

<210> SEQ ID NO 13
<211> LENGTH: 32
<212> TYPE: DNA
<213> ORGANISM: artificial
<220> FEATURE:
<223> OTHER INFORMATION: Sequence of the oligonucleotide primer POX23

<400> SEQUENCE: 13
gagaacgaya actggacsgg ccccgayggc gt                                 32

<210> SEQ ID NO 14
<211> LENGTH: 26
<212> TYPE: DNA
<213> ORGANISM: artificial
<220> FEATURE:
<223> OTHER INFORMATION: Sequence of the oligonucleotide primer POX26
```

```
<400> SEQUENCE: 14
gagaactgga tcggycccga yggygt                                              26

<210> SEQ ID NO 15
<211> LENGTH: 17
<212> TYPE: DNA
<213> ORGANISM: artificial
<220> FEATURE:
<223> OTHER INFORMATION: Sequence of the oligonucleotide primer POX27
<220> FEATURE:
<221> NAME/KEY: misc_feature
<222> LOCATION: (15)..(15)
<223> OTHER INFORMATION: n can be c or i

<400> SEQUENCE: 15
garaaytgga thggncc                                                        17

<210> SEQ ID NO 16
<211> LENGTH: 20
<212> TYPE: DNA
<213> ORGANISM: artificial
<220> FEATURE:
<223> OTHER INFORMATION: Sequence of the ologonucleotide primer POX28

<400> SEQUENCE: 16
ctcttcctcg cygtsggyca                                                     20

<210> SEQ ID NO 17
<211> LENGTH: 20
<212> TYPE: DNA
<213> ORGANISM: artificial
<220> FEATURE:
<223> OTHER INFORMATION: Sequence of the ologonucleotide primer POX29

<400> SEQUENCE: 17
tgrccsacrg cgaggaagag                                                     20

<210> SEQ ID NO 18
<211> LENGTH: 20
<212> TYPE: DNA
<213> ORGANISM: artificial
<220> FEATURE:
<223> OTHER INFORMATION: Sequence of the oligonucleotide primer POX30

<400> SEQUENCE: 18
taccagggyg cyccsaacac                                                     20

<210> SEQ ID NO 19
<211> LENGTH: 20
<212> TYPE: DNA
<213> ORGANISM: artificial
<220> FEATURE:
<223> OTHER INFORMATION: Sequence of the oligonucleotide primer POX31

<400> SEQUENCE: 19
gtgttsggrg crccctggta                                                     20

<210> SEQ ID NO 20
<211> LENGTH: 17
<212> TYPE: DNA
<213> ORGANISM: artificial
<220> FEATURE:
<223> OTHER INFORMATION: Sequence of the oligonucleotide primer POX4
<220> FEATURE:
<221> NAME/KEY: misc_feature
<222> LOCATION: (12)..(12)
```

-continued

```
<223> OTHER INFORMATION: n can be c or i

<400> SEQUENCE: 20
tggtaycayw sncaytt                                                  17

<210> SEQ ID NO 21
<211> LENGTH: 17
<212> TYPE: DNA
<213> ORGANISM: artificial
<220> FEATURE:
<223> OTHER INFORMATION: Sequence of the oligonucleotide primer POX5
<220> FEATURE:
<221> NAME/KEY: misc_feature
<222> LOCATION: (6)..(6)
<223> OTHER INFORMATION: n can be c or i

<400> SEQUENCE: 21
aartgnswrt grtacca                                                  17

<210> SEQ ID NO 22
<211> LENGTH: 20
<212> TYPE: DNA
<213> ORGANISM: artificial
<220> FEATURE:
<223> OTHER INFORMATION: Sequence of the oligonucleotide primer POX6
<220> FEATURE:
<221> NAME/KEY: misc_feature
<222> LOCATION: (9)..(9)
<223> OTHER INFORMATION: n can be c or i
<220> FEATURE:
<221> NAME/KEY: misc_feature
<222> LOCATION: (15)..(15)
<223> OTHER INFORMATION: n can be c or i

<400> SEQUENCE: 22
atgcayytnc ayggncayga                                               20

<210> SEQ ID NO 23
<211> LENGTH: 20
<212> TYPE: DNA
<213> ORGANISM: artificial
<220> FEATURE:
<223> OTHER INFORMATION: Sequence of the oligonucleotide primer POX7
<220> FEATURE:
<221> NAME/KEY: misc_feature
<222> LOCATION: (6)..(6)
<223> OTHER INFORMATION: n can be c or i
<220> FEATURE:
<221> NAME/KEY: misc_feature
<222> LOCATION: (12)..(12)
<223> OTHER INFORMATION: n can be c or i

<400> SEQUENCE: 23
tcrtgnccrt gnarrtgcat                                               20

<210> SEQ ID NO 24
<211> LENGTH: 17
<212> TYPE: DNA
<213> ORGANISM: artificial
<220> FEATURE:
<223> OTHER INFORMATION: Sequence of the oligonucleotide primer POX8
<220> FEATURE:
<221> NAME/KEY: misc_feature
<222> LOCATION: (6)..(6)
<223> OTHER INFORMATION: n can be c or i
<220> FEATURE:
<221> NAME/KEY: misc_feature
<222> LOCATION: (12)..(12)
<223> OTHER INFORMATION: n can be c or i

<400> SEQUENCE: 24
```
cayytncayg gncayga                                                    17

<210> SEQ ID NO 25
<211> LENGTH: 17
<212> TYPE: DNA
<213> ORGANISM: artificial
<220> FEATURE:
<223> OTHER INFORMATION: Sequence of the oligonucleotide primer POX9
<220> FEATURE:
<221> NAME/KEY: misc_feature
<222> LOCATION: (6)..(6)
<223> OTHER INFORMATION: n can be c or i
<220> FEATURE:
<221> NAME/KEY: misc_feature
<222> LOCATION: (12)..(12)
<223> OTHER INFORMATION: n can be c or i

<400> SEQUENCE: 25
tcrtgnccrt gnarrtg                                                    17

<210> SEQ ID NO 26
<211> LENGTH: 23
<212> TYPE: DNA
<213> ORGANISM: artificial
<220> FEATURE:
<223> OTHER INFORMATION: Sequence of the oligonucleotide primer POX10
<220> FEATURE:
<221> NAME/KEY: misc_feature
<222> LOCATION: (6)..(6)
<223> OTHER INFORMATION: n can be c or i

<400> SEQUENCE: 26
tgccangcda trtgrcartg cat                                             23

<210> SEQ ID NO 27
<211> LENGTH: 20
<212> TYPE: DNA
<213> ORGANISM: artificial
<220> FEATURE:
<223> OTHER INFORMATION: Sequence of the oligonucleotide primer POX11
<220> FEATURE:
<221> NAME/KEY: misc_feature
<222> LOCATION: (6)..(6)
<223> OTHER INFORMATION: n can be i or c

<400> SEQUENCE: 27
tgccangcda trtgrcartg                                                 20

<210> SEQ ID NO 28
<211> LENGTH: 17
<212> TYPE: DNA
<213> ORGANISM: artificial
<220> FEATURE:
<223> OTHER INFORMATION: Sequene of the oligonucleotide primer POX12

<400> SEQUENCE: 28
tggtaccact cgcattt                                                    17

<210> SEQ ID NO 29
<211> LENGTH: 17
<212> TYPE: DNA
<213> ORGANISM: artificial
<220> FEATURE:
<223> OTHER INFORMATION: Sequence of the oligonucleotide primer POX13

<400> SEQUENCE: 29
tcgtggccgt gcaggtg                                                    17

<210> SEQ ID NO 30
<211> LENGTH: 23
<212> TYPE: DNA
<213> ORGANISM: artificial
<220> FEATURE:
<223> OTHER INFORMATION: Sequence of the oligonucleotide primer POX14

<400> SEQUENCE: 30
tgccaggcaa tgtggcagtg cat                                          23

<210> SEQ ID NO 31
<211> LENGTH: 20
<212> TYPE: DNA
<213> ORGANISM: artificial
<220> FEATURE:
<223> OTHER INFORMATION: Sequence of the oligonucleotide primer POX15

<400> SEQUENCE: 31
tgccaggcaa tgtggcagtg                                              20

<210> SEQ ID NO 32
<211> LENGTH: 1056
<212> TYPE: DNA
<213> ORGANISM: Thielavia arenaria ALKO4197
<220> FEATURE:
<221> NAME/KEY: misc_feature
<222> LOCATION: (1)..(1056)
<223> OTHER INFORMATION: Sequence of the PCR fragment obtained from
      Thielavia arenaria ALKO4197 using the primers POX27 and POX31

<400> SEQUENCE: 32
gagaactgga tcgggcccga tggcgttctc aagaatgtgg tgatgttggt caatggtacg     60
ttgatgtcca attctgtata aagagaagaa acgtgctgat acgctccctt cgtctagaca    120
agattatagg tatgttgtca aacccgctgt aaccccaacc gccaagacct ggaggctcct    180
cgcctggacg tgttgtacaa tatgctgacc tcgccgccag ggccaaccat ccgcgcgaac    240
tggggtgaca atatcgaagt cactgtcatc aacaatctca aaaccaatgg gtacgaccac    300
ttgaatcatc ccgggcctac ccctaacaca aaatctcaac gtgcatccga tctgacgtat    360
tatatccatc tagtacctcg atgcactggc atggccttcg tcagctgggt aacgttttca    420
acgacggtgc caacgcgtg actgagtgcc aatcccgcc caaggagggg cgcaagacgt      480
acaagttccg tgcgacacag tatggcacca gctggtatca ctcccacttc tcggcccagt    540
acggcaacgg cgtggtcggc accatccaga tcgacggccc tgcctctctg ccatatgaca    600
ttgatctggg cgtgttccct ctcatggact actactacag gtcggccgat gagctggtgc    660
acttcaccca gagcaacggc gccccgccaa gcgacaacgt cctcttcaat ggcaccgccc    720
gtcaccctga cgggggca ggccagtggt acaacgtcac gctgactcca ggcaagcgac      780 accgctgcg catcatcaac acgtcgaccg acaaccactt tcaggtgtcg cttgtcggcc    840
acaacatgac cgtcattgcc accgacatgg tccccgtcaa cgcctttact gtcagcagcc    900
tattcctcgc cgtaggccag cgatacgatg tcaccatcga cgccaatagc ccggtgggca    960
actactggtt caacgtgact ttcggcgatg ggttgtgcgg ctccagtaac aacaaattcc   1020
cagccgccat cttccgctac cagggcgccc cgaaca                             1056

<210> SEQ ID NO 33
<211> LENGTH: 1296
<212> TYPE: DNA
<213> ORGANISM: Thielavia arenaria ALKO4197
<220> FEATURE:

```
<221> NAME/KEY: misc_feature
<222> LOCATION: (1)..(1296)
<223> OTHER INFORMATION: Sequence of the PCR fragment obtained from
      Thielavia arenaria ALKO4197 using the primers POX4 and POX11

<400> SEQUENCE: 33
tggtaccaca gccacttcag cctccagtac gccgagggtc tcttcggggg catgattctc     60
cgggggccca gcacggccaa ctgggacgag gacctcggag tcttgtttct gcaggactgg    120
tcacacgtcg aagccttcac taggtggcat gaagcgaaag ccgggtttcc tccatcactc    180
gatggcggcc tgatcaacgg cacaaacaca tttgactgct ccacactgtc gccgacggac    240
cccaagtgca ccggcaatgg caagaagttc gagaccgtct tcgaacccgg caagaagtat    300
cttatccgcc tcatcaacgt ggcaatcgac ggagtgttcc agttcagcat cgacggacac    360
agcctcaccg tcatagcgac ggatttggtg ccgattgtcc cctacgacga cgacagcgtc    420
cagatcacca tcggccagcg ttatgatatc attgtcgagg caaacgcaac gccgggaaac    480
tactggatgc gggccgactg ggtcacagcc tgcgtgacca cgatcacccc cgagcacatg    540
acgggcatcg ttcgctatga gcgagcagc atcgacccc cgacgtccga agcaacgtc      600 acaaaaacca gcagctgcct cggcgagccg aatgagaaaa cgatcccgca tttgtcgctc    660
gatgtcacca acattggcgg caccaacgtc gaggaactgt cctttgacac cacctctggc    720
gactacttcc agtggactct caatacgagc agcctggtgc tcgattgggg gaacccgacg    780
atggcccgaa tcttcaacgg ggatgccatc ttccccaccg agtacaacgt cgttgccgtc    840
aacgtgagtc tccccatgtt tgcagtaacc ccgaaccct agagagtgcg gcgatttcgc    900
taatcatggt tccctatccg cagaaaaccg gcactggacc ggaatggaca gtcctagtga    960
ttcaagatca aagcaatttg ccgtaagcct cccaaattcc caatccactt gtccctgccc   1020
ttgcaagtca ggtgcgctgc gtgggaatgg gatcccagct gacgtcaagg ctttttcatt   1080
tgtttgcagc attgcgcatc cgatccacct gcacggccac gacttttggg tgctggcggc   1140
cgaggagggc gtcttcaatg caacattag cagcttcaac acgaggaacc cggcgcggcg    1200
cgacgtcgcc acgctgccgg gcagaggcta cctggccatc gccttccaga tcgacaaccc   1260
gggcacctgg ctgacccact gccacattgc ctggca                             1296

<210> SEQ ID NO 34
<211> LENGTH: 1295
<212> TYPE: DNA
<213> ORGANISM: Thielavia arenaria ALKO4197
<220> FEATURE:
<221> NAME/KEY: misc_feature
<222> LOCATION: (1)..(1295)
<223> OTHER INFORMATION: Sequence of the PCR fragment obtained from
      Thielavia arenaria ALKO4197 using the primers POX27 and POX9

<400> SEQUENCE: 34
gagaactgga ttggccctga tggggttcgg aagcctgcca tgcttataaa cggtgtgttg      60
ccagagccca caagatcctc caaggtcact tctgacaaca aggcaggctc attccctggt    120
cccacaatct cagccgactg gggcgactac attattgtca atgtccacaa tgacatgcaa    180
gataacgggt aagaaatgca gcacggtacc cccggcatcc tcaaacctgc ttgctaacac    240
ataggtagaa cgtcaatcca ttggcatgga atccgtcagc ttggcgagag caaccaggac    300
ggcgcaaacg gcgtaacgga atgccccatt cctcccggat ccagcaaaac ctacgacttc    360
catgtgacgc agtacggcac ctcgtggtac cacagccact actccaacca gtacggcaat    420
ggggtcgtgg gcgccctgat cgtgcgcggc ccggcatcag ccaactacga catcgacctc    480
```

```
ggtccctacc tgatcagtga ctactactac gaaaccgcag accgcctcca tctccgagcc    540
gagctggtca gcaacggccc accgccagac agcgacaaca tcctgttccg cggcaaaaac    600 atcaaccccca gcgtgcagg cagcggctcc tacgaccgcc tcgtcctaac ccccggcaag    660
aagcatctaa tccggctcat caacgccagc gtggacaact ccttcgtcat ctccctcgtc    720
ggccacaact tcaccgtcat ctccaccgac atggtcccca tcaccctgt cgtgcgcagc    780 tccttattca tgggcgtcgg ccagcggtac gacgtcattg tcgaagccaa ccagcccgtg    840
ggcaactact ggctcaacgc gacgctcgag gcccagaaca actgcgggca ttcggtcaac    900
cccttccccg cggctattgt ccagtacgag ggcgccagct ccaccgccct gccgaccaac    960
cgcgggacgc ccctgacggc gacatgcaat ggcgagaaag ggttttcgcc cattgttaag   1020
cggacagttt caagttccct gttccagccg tctaccctgc cagtcagcct tgaattcccc   1080
actacagacc gcgggcaggt gtttgagtgg cgggttaaga acacgccgat aagcgtcgaa   1140
tgggagcatc ccgtgctgga gtacattttg caggggaaca cctccttccc ggcaaaggcc   1200
aatctcattg aagtcccgca ggcaaatgtc tggacgttct gggtgattca gaacgggttt   1260
gggctgccgc acccgattca cctgcacggg cacga                             1295

<210> SEQ ID NO 35
<211> LENGTH: 224
<212> TYPE: DNA
<213> ORGANISM: Chaetomium thermophilum ALKO 4265
<220> FEATURE:
<221> NAME/KEY: misc_feature
<222> LOCATION: (1)..(224)
<223> OTHER INFORMATION: Sequence of the PCR fragment obtained from
      Chaetomium thermophilum ALKO4265 using the primers POX8 and POX11

<400> SEQUENCE: 35
catctccatg ggcacgactt cctcattgtc ggccgctccc ccgacgtccc gccgggctcg     60
aaccagcgct acaacttcga ccccgccacc gacatctacc gcctgcgcgg tcagaacccg    120
acccgtcgtg acgtcgccat gcttcctgcc ggcggctggc tgctgctcgc cttcctcacc    180
gacaaccccg gtgcctggct cttccactgc acatcgcct ggca                      224

<210> SEQ ID NO 36
<211> LENGTH: 929
<212> TYPE: DNA
<213> ORGANISM: Chaetomium thermophilum ALKO4265
<220> FEATURE:
<221> NAME/KEY: misc_feature
<222> LOCATION: (1)..(929)
<223> OTHER INFORMATION: Sequence of the PCR fragment obtained from
      Chaetomium thermophilum ALKO4265 using the primers POX4 and POX9

<400> SEQUENCE: 36
tggtatcatt gccacttctc caaccagtac ggcaacggcg tgctcggcgc actggtggtc     60
aaaggcccgg cttccgccaa ctacgacatc gacctcggcc cgtacatcat tagcgactac    120
taccacgaga cggccgacag attacatctc caggcagagc tactccgcaa cgggccccct    180
ccagacagcg acaacatcct cttcaggggc aagaacatca ccctgacgg tcgggccgc     240 ggctcttatg accgattaac cctcatccca ggcaagaaac acctgctgcg tctgatcaac    300
gcaagcgtgg ataactcctt cacggtctcc ctcgtgggac acaacttcac ggtcattgcg    360
accgatatgg tccggtccga gcaaccgtc gcaggagcc tgttcatggc cgtcggccag     420
cgttatgatg ttattgttac cgccgaccag cccgtagata attattggct gaacgtcacc    480
```

-continued

| | |
|---|---|
| ctggaagcaa acaacaactg cggccgctct cgcaacccct acccagcagc catcatccac | 540 |
| tacgagggag ccagcccaac cgccctcccc accaaccgtg gcaccccct cgtagcaacc | 600 |
| tgcaccggcg agacaggctt caccccgtc gtgccgcgga atatccccc caacttcttc | 660 |
| cgcccttccg acatcgcctc caatacctg ccaatcggcc tcaacattgt caaccacacc | 720 |
| actaaaggcc aaatcttctc ctggcatgtg aagaacacgc ctatttccgt ggaatggggg | 780 |
| catccagtat tagagtacat cctcgaaggg aattactcct ttcccgcagc ggttaatctg | 840 |
| attcaactca accaaaaaga cacctggaca ctcttttttgg tgcatagttc gttatcatta | 900 |
| ccgcacccaa tccacctcca cgggcacga | 929 |

<210> SEQ ID NO 37
<211> LENGTH: 251
<212> TYPE: DNA
<213> ORGANISM: Chaetomium thermophilum ALKO4265
<220> FEATURE:
<221> NAME/KEY: misc_feature
<222> LOCATION: (1)..(251)
<223> OTHER INFORMATION: Sequence of the PCR fragment obtained from
      Chatomium thermophilum ALKO465 using the primers POX8 and POX11

<400> SEQUENCE: 37

| | |
|---|---|
| cacttccacg ggcacgactt ttacatcctc cacgagggcc ccggcgactg ggatggcacc | 60 |
| atggtccggc caagcaaccc ccacagacgg gacgtctacc tggtacgcgg gtttggtcat | 120 |
| cttgttctgc aattcgatgg tgaacctggt acgtgtgccg tagttctcag ccagactccg | 180 |
| tgtgcgcttg gaggaaggca atctaacaac ataataggag tctgggcctt ccactgtcac | 240 |
| atcgcgtggc a | 251 |

<210> SEQ ID NO 38
<211> LENGTH: 2680
<212> TYPE: DNA
<213> ORGANISM: Thielavia arenaria ALKO4197
<220> FEATURE:
<221> NAME/KEY: misc_feature
<222> LOCATION: (178)..(2456)
<223> OTHER INFORMATION: Talcc1
<220> FEATURE:
<221> NAME/KEY: Intron
<222> LOCATION: (406)..(456)
<220> FEATURE:
<221> NAME/KEY: Intron
<222> LOCATION: (536)..(597)
<220> FEATURE:
<221> NAME/KEY: Intron
<222> LOCATION: (610)..(700)
<220> FEATURE:
<221> NAME/KEY: Intron
<222> LOCATION: (771)..(853)
<220> FEATURE:
<221> NAME/KEY: Intron
<222> LOCATION: (1824)..(1902)
<220> FEATURE:
<221> NAME/KEY: Intron
<222> LOCATION: (1975)..(2033)

<400> SEQUENCE: 38

| | |
|---|---|
| ggatccccgg gtcagtctat ataaggggct gagtgtccag ctcttccatg cctttgattc | 60 |
| tcttgaatca ccaggacact cgggcggctt cagtcttgca taactcgggt cttcccttcc | 120 |
| tctcactgct tttcttcgct cagatatatt tcaggcgacc tcaaacagct cgccatcatg | 180 |
| aagtctgggg ccgccgccgt ggcgctcatg gtgggcattc tcagccctca tgctgccgcc | 240 |
| gcacctcctg caaacccggt ccagagagac atgctccagg tccttgaggc gagacagtct | 300 |

```
ggcccgactt gcaacacccc gtccaatcgt gcgtgctgga ccaatggttt cgacatcaac    360
accgactatg aagtcagcac tcctaatacc ggacgtactg tggccgtaag cttcccctcc    420
ctttaaggag gcagagctag gactaacaag caccagtacc aacttaccct cactgagaaa    480
gagaactgga tcggtcccga tggcgttctc aagaatgtgg tgatgttggt caatggtacg    540
ttgatgtcca attctgtata aagagaagaa acgtgctgat acgctccctt cgtctagaca    600
agattatagg tatgttgtca aacccgctgt aaccccaacc gccaagacct ggaggctcct    660
cgcctggacg tgttgtacaa tatgctgacc tcgccgccag ggccaaccat ccgcgcgaac    720
tggggtgaca atatcgaagt cactgtcatc aacaatctca aaaccaatgg gtacgaccac    780
ttgaatcatc ccgggcctac ccctaacaca aaatctcaac gtgcatccga tctgacgtat    840
tatatccatc tagtacctcg atgcactggc atggccttcg tcagctgggt aacgttttca    900
acgacggtgc caacggcgtg actgagtgcc caatcccgcc caaggagggg cgcaagacgt    960
acaagttccg tgcgacacag tatggcacca gctggtatca ctcccacttc tcggcccagt   1020
acggcaacgg cgtggtcggc accatccaga tcgacggccc tgcctctctg ccatatgaca   1080
ttgatctggg cgtgttccct ctcatggact actactacag gtcggccgat gagctggtgc   1140
acttcaccca gagcaacggc gccccgccaa gcgacaacgt cctcttcaat ggcaccgccc   1200
gtcaccctga cgggggcagg ccagtggt acaacgtcac gctgactcca ggcaagcgac   1260
accgcctgcg catcatcaac acgtcgaccg acaaccactt tcaggtgtcg cttgtcggcc   1320
acaacatgac cgtcattgcc accgacatgg tccccgtcaa cgcctttact gtcagcagcc   1380
tattcctcgc cgtaggccag cgatacgatg tcaccatcga cgccaatagc ccggtgggca   1440
actactggtt caacgtgact ttcggcgatg ggttgtgcgg ctccagtaac aacaaattcc   1500
cagccgccat cttccgctac cagggcgccc ccgctacgct cccgacggat cagggtctac   1560
ccgtgcccaa tcacatgtgt ttggacaacc tgaacctaac tcctgtggtg acacggagcg   1620
cgcccgtcaa caactttgtc aagcgtccgt ccaacacgct gggcgtcact ctcgatatcg   1680
gcggcacgcc gctctttgtg tggaaggtca acggcagcgc catcaacgtc gactggggca   1740
agccgatcct tgactatgtc atgagcggca acacgagcta cccggtcagc gataacattg   1800
tgcaggtgga cgctgttgac caggtacgcc cctcttgaag cccctagcag ttcacgctag   1860
tatacaatac aagtacatgc taacacttcc ctccctattc agtggactta ctggctgatc   1920
gagaacgacc cgaccaatcc cattgtcagc ttgccgcacc cgatgcatct gcacgtacgt   1980
tcaaacctcc cccccacccc cacttcatac aaaatatact gacaaatcga cagggccacg   2040
acttcctcgt cctgggccga tcacccgacg agctccccag cgcgggggtc cgtcacatct   2100
ttgacccggc caaggacctg ccccggctta agggcaacaa ccccgtgcgg cgggacgtga   2160
cgatgcttcc ggcgggcggc tggctgctgc tggcgttcaa gacggacaac ccgggcgcat   2220
ggctgttcca ctgccacatt gcgtggcacg tgtcggcgg cctgtcggtc gacttcctcg   2280
agcggcccaa cgaccttcgc acgcagctca acagcaacgc caagcgcgcc gaccgcgacg   2340
acttcaaccg cgtctgccgc gagtggaacg cctactggcc taccaacccg ttccccaaga   2400
tcgactcggg cttgaggcac cggtttgttg aggagagcga gtggatggtt cgctaaactg   2460
cctggctgtg ccaattgatt tgatgggtac atgtacctgt tggtgttact gttgacgagg   2520
ctgtgtaagt accatggcaa aggggtgttt tcagggtgc tctggggtaa ttggcacagt   2580
acatggaggg gtctggggtt gggtatacaa ggcttgctgc tccgttttta tcttttggct   2640
tgattaagac tttcttgtct gatgtacgag tcaggccgcc                         2680
```

<210> SEQ ID NO 39
<211> LENGTH: 617
<212> TYPE: PRT
<213> ORGANISM: Thielavia arenaria ALKO4197
<220> FEATURE:
<221> NAME/KEY: MISC_FEATURE
<222> LOCATION: (1)..(617)
<223> OTHER INFORMATION: Deduced amino acid sequence of Thielavia arenaria ALKO4197 TaLcc1

<400> SEQUENCE: 39

```
Met Lys Ser Trp Ala Ala Val Ala Leu Met Val Gly Ile Leu Ser
1               5                   10                  15

Pro His Ala Ala Ala Pro Pro Ala Asn Pro Val Gln Arg Asp Met
                20                  25                  30

Leu Gln Val Leu Glu Ala Arg Gln Ser Gly Pro Thr Cys Asn Thr Pro
            35                  40                  45

Ser Asn Arg Ala Cys Trp Thr Asn Gly Phe Asp Ile Asn Thr Asp Tyr
        50                  55                  60

Glu Val Ser Thr Pro Asn Thr Gly Arg Thr Val Ala Tyr Gln Leu Thr
65                  70                  75                  80

Leu Thr Glu Lys Glu Asn Trp Ile Gly Pro Asp Gly Val Leu Lys Asn
                85                  90                  95

Val Val Met Leu Val Asn Asp Lys Ile Ile Gly Pro Thr Ile Arg Ala
                100                 105                 110

Asn Trp Gly Asp Asn Ile Glu Val Thr Val Ile Asn Asn Leu Lys Thr
            115                 120                 125

Asn Gly Thr Ser Met His Trp His Gly Leu Arg Gln Leu Gly Asn Val
        130                 135                 140

Phe Asn Asp Gly Ala Asn Gly Val Thr Glu Cys Pro Ile Pro Pro Lys
145                 150                 155                 160

Gly Gly Arg Lys Thr Tyr Lys Phe Arg Ala Thr Gln Tyr Gly Thr Ser
                165                 170                 175

Trp Tyr His Ser His Phe Ser Ala Gln Tyr Gly Asn Gly Val Val Gly
                180                 185                 190

Thr Ile Gln Ile Asp Gly Pro Ala Ser Leu Pro Tyr Asp Ile Asp Leu
            195                 200                 205

Gly Val Phe Pro Leu Met Asp Tyr Tyr Arg Ser Ala Asp Glu Leu
        210                 215                 220

Val His Phe Thr Gln Ser Asn Gly Ala Pro Pro Ser Asp Asn Val Leu
225                 230                 235                 240

Phe Asn Gly Thr Ala Arg His Pro Glu Thr Gly Ala Gly Gln Trp Tyr
                245                 250                 255

Asn Val Thr Leu Thr Pro Gly Lys Arg His Arg Leu Arg Ile Ile Asn
                260                 265                 270

Thr Ser Thr Asp Asn His Phe Gln Val Ser Leu Val Gly His Asn Met
            275                 280                 285

Thr Val Ile Ala Thr Asp Met Val Pro Val Asn Ala Phe Thr Val Ser
        290                 295                 300

Ser Leu Phe Leu Ala Val Gly Gln Arg Tyr Asp Val Thr Ile Asp Ala
305                 310                 315                 320

Asn Ser Pro Val Gly Asn Tyr Trp Phe Asn Val Thr Phe Gly Asp Gly
                325                 330                 335

Leu Cys Gly Ser Ser Asn Asn Lys Phe Pro Ala Ala Ile Phe Arg Tyr
                340                 345                 350
```

```
Gln Gly Ala Pro Ala Thr Leu Pro Thr Asp Gln Gly Leu Pro Val Pro
        355                 360                 365

Asn His Met Cys Leu Asp Asn Leu Asn Leu Thr Pro Val Val Thr Arg
        370                 375                 380

Ser Ala Pro Val Asn Asn Phe Val Lys Arg Pro Ser Asn Thr Leu Gly
385                 390                 395                 400

Val Thr Leu Asp Ile Gly Gly Thr Pro Leu Phe Val Trp Lys Val Asn
                405                 410                 415

Gly Ser Ala Ile Asn Val Asp Trp Gly Lys Pro Ile Leu Asp Tyr Val
            420                 425                 430

Met Ser Gly Asn Thr Ser Tyr Pro Val Ser Asp Asn Ile Val Gln Val
        435                 440                 445

Asp Ala Val Asp Gln Trp Thr Tyr Trp Leu Ile Glu Asn Asp Pro Thr
    450                 455                 460

Asn Pro Ile Val Ser Leu Pro His Pro Met His Leu His Gly His Asp
465                 470                 475                 480

Phe Leu Val Leu Gly Arg Ser Pro Asp Glu Leu Pro Ser Ala Gly Val
                485                 490                 495

Arg His Ile Phe Asp Pro Ala Lys Asp Leu Pro Arg Leu Lys Gly Asn
            500                 505                 510

Asn Pro Val Arg Arg Asp Val Thr Met Leu Pro Ala Gly Gly Trp Leu
        515                 520                 525

Leu Leu Ala Phe Lys Thr Asp Asn Pro Gly Ala Trp Leu Phe His Cys
    530                 535                 540

His Ile Ala Trp His Val Ser Gly Gly Leu Ser Val Asp Phe Leu Glu
545                 550                 555                 560

Arg Pro Asn Asp Leu Arg Thr Gln Leu Asn Ser Asn Ala Lys Arg Ala
                565                 570                 575

Asp Arg Asp Asp Phe Asn Arg Val Cys Arg Glu Trp Asn Ala Tyr Trp
            580                 585                 590

Pro Thr Asn Pro Phe Pro Lys Ile Asp Ser Gly Leu Arg His Arg Phe
        595                 600                 605

Val Glu Glu Ser Glu Trp Met Val Arg
    610                 615

<210> SEQ ID NO 40
<211> LENGTH: 3084
<212> TYPE: DNA
<213> ORGANISM: Thielavia arenaria ALKO4197
<220> FEATURE:
<221> NAME/KEY: misc_feature
<222> LOCATION: (1)..(2600)
<223> OTHER INFORMATION: Nucleotide sequence of Thielavia arenaria
      ALKO4197 Ta lcc2 gene.
<220> FEATURE:
<221> NAME/KEY: misc_feature
<222> LOCATION: (644)..(2600)
<223> OTHER INFORMATION: Ta lcc2
<220> FEATURE:
<221> NAME/KEY: misc_feature
<222> LOCATION: (644)..(646)
<223> OTHER INFORMATION: putative start ,ATG
<220> FEATURE:
<221> NAME/KEY: misc_feature
<222> LOCATION: (674)..(676)
<223> OTHER INFORMATION: putative start ,ATG
<220> FEATURE:
<221> NAME/KEY: Intron
<222> LOCATION: (2003)..(2082)
<220> FEATURE:
<221> NAME/KEY: Intron
```

<222> LOCATION: (2142)..(2248)

<400> SEQUENCE: 40

```
ggatcccgta gtcaacaaga cccagcaccc agggtaacca tcctatacgg ggcaagatct      60
accacttgca gcgatatatt gaagtccaat acatcgtcac tgtagtagtc atggtgttct     120
gtaagttccg gcagggactg tagtactcga cgggttcctc tccttccagt tagccctcgt     180
agagcatgtt gacgttacga taggtttccc ccccccatt tggagctgtg atatactttc     240
aagttgttga aggcctttag ctgagcataa cgatcgtggc tgacgaaagc ctccgtgcgg     300
cacacctaaa attacgattc cgaatgctcc tccaaggagt tgtcatatga tactattgat     360
gtgagcttca ggggagcagg cccattacgg aaggtagacc agggacaact ccttctcggc     420
ttaaccgggc cggatcgtgg aatgcctcgc caaagactca ttgcgaggcg acatggagcc     480
aagcccacct tctcttgagg ctctgatatt gatgctgtac gagtataaag tcgatgatct     540
cctgcaatgt cccagagtct atccaagcag ctcttggacc aaggaagcca tcggtcactc     600
aacaggcgcg gccacattcg ttcaactttg aattggtagc accatgttaa ccgagacact     660
caagtcaaga aacatgttgc aatcaatcct tgctcttctt gccaccgccc tgggctcatc     720
tgccttcgcc atccctgaac tcccagaggt ctcgcttcag ccccggcaag cttgcgagaa     780
cactgcaacg tctcgccaat gctggggtga ccttcaatc acaccaact actatgaagt     840
tcttcccagc accgggcgcc cgccgcagga gtattggctg agtgtcgtgg aaggcccttg     900
tgccccagac ggatataaca ggacctgtat gacctttaac ggcaccgtgc cggggccaac     960
cctcttcgcc gattggggcg acgagctcgt tatccatgtc acaaacaaca tggtcaacaa    1020
tggcaccgcg atccactggc acgggattcg catgctgaat aacacgctca acgacggcgt    1080
tcccggagtg acgcagtgcg ccatcgcccc gggcgagtcc atgacatacc ggttcaacgt    1140
cacccagtac ggctcgactt ggtaccacag ccacttcagc ctccagtacg ccagggtct    1200
cttcggggc atgattctcc gggggcccag cacggccaac tgggacgagg acctcggagt    1260
cttgtttctg caggactggt cacacgtcga agccttcact aggtggcatg aagcgaaagc    1320
cgggtttcct ccatcactcg atggcggcct gatcaacggc acaaacacat ttgactgctc    1380
cacactgtcg ccgacggacc ccaagtgcac cggcaatggc aagaagttcg agaccgtctt    1440
cgaacccggc aagaagtatc ttatccgcct catcaacgtg gcaatcgacg gagtgttcca    1500
gttcagcatc gacggacaca gcctcaccgt catagcgacg gatttggtgc cgattgtccc    1560
ctacacgacc gacagcgtcc agatcaccat cggccagcgt tatgatatca ttgtcgaggc    1620
aaacgcaacg ccgggaaact actggatgcg ggccgactgg gtcacagcct gcgtgaccaa    1680
cgatcacccc gagcacatga cgggcatcgt tcgctatgac gcgagcagca tcgaccccc    1740
gacgtccgaa agcaacgtca caaaaaccag cagctgcctc ggcgagccga atgagaaaac    1800
gatcccgcat ttgtcgctcg atgtcaccaa cattggcggc accaacgtcg aggaactgtc    1860
ctttgacacc acctctggcg actacttcca gtggactctc aatacgagca gcctggtgct    1920
cgattggggg aacccgacga tggcccgaat cttcaacggg gatgccatct tcccaccgga    1980
gtacaacgtc gttgccgtca acgtgagtct ccccatgttt gcagtaaccc cgaacccta    2040
gagagtgcgc cgatttcgct aatcatggtt ccctatccgc agaaaaccgg cactggaccg    2100
gaatggacag tcctagtgat tcaagatcaa agcaatttgc cgtaagcctc ccaaattccc    2160
aatccacttg tccctgccct tgcaagtcag gtgcgctgcg tgggaatggg atcccagctg    2220
acgtcaaggc ttttcattt gtttgcagca ttgcgcatcc gatccacctg cacggccacg    2280
```

```
actttttgggt gctggcggcc gaggagggcg tcttcaatgg caacattagc agcttcaaca    2340
cgaggaaccc ggcgcggcgc gacgtcgcca cgctgccggg cagaggctac ctggccatcg    2400
ccttccagat cgacaacccg ggcacctggc tgacccactg ccacattgcc tggcacgcca    2460
gccagggcct ttcgctcgag tttgtcgaga gccagtccga gattgtgacc gacgaggtca    2520
gccgcggcgt gtttaacgac gtctgcgctt cctggcgggc acatgacccc ctttgggagc    2580
aggaggactc gggaatttga atctgagggc gtcgtttctt tccttccggt gtttgagagt    2640
aagatatgta tcatgaaatt tctttattct ttattttttg ttctttcttt ggtccgtgtt    2700
gtctgctctg cgggttagaa tacacgagga aacccaactg ggtgttgagt ggactcttcg    2760
ggctcgagcc caacgctcat tgtttcccta agttgtctt tgtttctgg ttcaccactc     2820
caccatttgt acggggtagt tgacggattg ttcggctcac tcaaccggct gtaagtgttg    2880
gagatgtttc aactctcaat ctcggaggtt gggctgcggc tcctgcgatg aggggatggt    2940
cgcagtatgt gctgttagta cagaaaaaca cagcataaag caatacgaac tgtgtgcccg    3000
tccgtaccta aggaacaaac cggtcaacaa gacacccagt gaaaggttat cagtccaagc    3060
cactcgggtt gaatttctca gctc                                           3084
```

<210> SEQ ID NO 41
<211> LENGTH: 589
<212> TYPE: PRT
<213> ORGANISM: Thielavia arenaria ALKO4197
<220> FEATURE:
<221> NAME/KEY: MISC_FEATURE
<222> LOCATION: (1)..(589)
<223> OTHER INFORMATION: Deduced amino acid sequence of Thielavia
      arenaria ALKO4197 TaLacc2

<400> SEQUENCE: 41

```
Met Leu Thr Glu Thr Leu Lys Ser Arg Asn Met Leu Gln Ser Ile Leu
1               5                   10                  15

Ala Leu Leu Ala Thr Ala Leu Gly Ser Ser Ala Phe Ala Ile Pro Glu
            20                  25                  30

Leu Pro Glu Val Ser Leu Gln Pro Arg Gln Ala Cys Glu Asn Thr Ala
        35                  40                  45

Thr Ser Arg Gln Cys Trp Gly Asp Leu Ser Ile Asp Thr Asn Tyr Tyr
    50                  55                  60

Glu Val Leu Pro Ser Thr Gly Arg Pro Pro Gln Glu Tyr Trp Leu Ser
65                  70                  75                  80

Val Val Glu Gly Pro Cys Ala Pro Asp Gly Tyr Asn Arg Thr Cys Met
                85                  90                  95

Thr Phe Asn Gly Thr Val Pro Gly Pro Thr Leu Phe Ala Asp Trp Gly
            100                 105                 110

Asp Glu Leu Val Ile His Val Thr Asn Asn Met Val Asn Asn Gly Thr
        115                 120                 125

Ala Ile His Trp His Gly Ile Arg Met Leu Asn Asn Thr Leu Asn Asp
    130                 135                 140

Gly Val Pro Gly Val Thr Gln Cys Ala Ile Ala Pro Gly Glu Ser Met
145                 150                 155                 160

Thr Tyr Arg Phe Asn Val Thr Gln Tyr Gly Ser Thr Trp Tyr His Ser
                165                 170                 175

His Phe Ser Leu Gln Tyr Ala Glu Gly Leu Phe Gly Gly Met Ile Leu
            180                 185                 190

Arg Gly Pro Ser Thr Ala Asn Trp Asp Glu Asp Leu Gly Val Leu Phe
```

```
                195                 200                 205
Leu Gln Asp Trp Ser His Val Glu Ala Phe Thr Arg Trp His Glu Ala
210                 215                 220
Lys Ala Gly Phe Pro Pro Ser Leu Asp Gly Gly Leu Ile Asn Gly Thr
225                 230                 235                 240
Asn Thr Phe Asp Cys Ser Thr Leu Ser Pro Thr Asp Pro Lys Cys Thr
                245                 250                 255
Gly Asn Gly Lys Lys Phe Glu Thr Val Phe Glu Pro Gly Lys Lys Tyr
            260                 265                 270
Leu Ile Arg Leu Ile Asn Val Ala Ile Asp Gly Val Phe Gln Phe Ser
        275                 280                 285
Ile Asp Gly His Ser Leu Thr Val Ile Ala Thr Asp Leu Val Pro Ile
290                 295                 300
Val Pro Tyr Thr Thr Asp Ser Val Gln Ile Thr Ile Gly Gln Arg Tyr
305                 310                 315                 320
Asp Ile Ile Val Glu Ala Asn Ala Thr Pro Gly Asn Tyr Trp Met Arg
                325                 330                 335
Ala Asp Trp Val Thr Ala Cys Val Thr Asn Asp His Pro Glu His Met
            340                 345                 350
Thr Gly Ile Val Arg Tyr Asp Ala Ser Ser Ile Asp Pro Pro Thr Ser
        355                 360                 365
Glu Ser Asn Val Thr Lys Thr Ser Ser Cys Leu Gly Glu Pro Asn Glu
370                 375                 380
Lys Thr Ile Pro His Leu Ser Leu Asp Val Thr Asn Ile Gly Gly Thr
385                 390                 395                 400
Asn Val Glu Glu Leu Ser Phe Asp Thr Thr Ser Gly Asp Tyr Phe Gln
                405                 410                 415
Trp Thr Leu Asn Thr Ser Ser Leu Val Leu Asp Trp Gly Asn Pro Thr
            420                 425                 430
Met Ala Arg Ile Phe Asn Gly Asp Ala Ile Phe Pro Thr Glu Tyr Asn
        435                 440                 445
Val Val Ala Val Asn Lys Thr Gly Thr Gly Pro Glu Trp Thr Val Leu
450                 455                 460
Val Ile Gln Asp Gln Ser Asn Leu Pro Ile Ala His Pro Ile His Leu
465                 470                 475                 480
His Gly His Asp Phe Trp Val Leu Ala Ala Glu Gly Val Phe Asn
                485                 490                 495
Gly Asn Ile Ser Ser Phe Asn Thr Arg Asn Pro Ala Arg Arg Asp Val
            500                 505                 510
Ala Thr Leu Pro Gly Arg Gly Tyr Leu Ala Ile Ala Phe Gln Ile Asp
        515                 520                 525
Asn Pro Gly Thr Trp Leu Thr His Cys His Ile Ala Trp His Ala Ser
530                 535                 540
Gln Gly Leu Ser Leu Glu Phe Val Glu Ser Gln Ser Glu Ile Val Thr
545                 550                 555                 560
Asp Glu Val Ser Arg Gly Val Phe Asn Asp Val Cys Ala Ser Trp Arg
                565                 570                 575
Ala His Asp Pro Leu Trp Glu Gln Glu Asp Ser Gly Ile
            580                 585

<210> SEQ ID NO 42
<211> LENGTH: 2971
<212> TYPE: DNA
<213> ORGANISM: Thielavia arenaria ALKO4197
```

```
<220> FEATURE:
<221> NAME/KEY: misc_feature
<222> LOCATION: (1)..(2971)
<223> OTHER INFORMATION: Nucleotide sequence of Thielavia arenaria
      AKO4197 Talcc3 gene
<220> FEATURE:
<221> NAME/KEY: misc_feature
<222> LOCATION: (275)..(2289)
<223> OTHER INFORMATION: Talcc3
<220> FEATURE:
<221> NAME/KEY: Intron
<222> LOCATION: (521)..(585)
<220> FEATURE:
<221> NAME/KEY: Intron
<222> LOCATION: (662)..(715)
<220> FEATURE:
<221> NAME/KEY: Intron
<222> LOCATION: (798)..(857)

<400> SEQUENCE: 42
acggctgcgg ttatcggagc acgttgcatg gcaatgtcca tactcttact gagaaaagag      60
ttcggtcaag ggacggtgct ggggaataga tgcccgtcta ggaattccgg tagtggcggt     120
ctttcggaaa tataaccgag caggacgttc agcccatcgt ccctgtgtat ataaagcatg     180
aagttattct atgtagaatc ctagactatc ttagaagcga acctttcgtc gcagatgctt     240
cgtgttttcc atcattactt cccgtagtac tagtatggtc tgccttcagt atcagctcac     300
agcagcctgc tttgctgtgt tagcggtcgt caccacccca gcttcctgct ctcctgtcca     360
gccgagcccc gttcacgatc tcttaccaag acaaacaata atccccggcg gtaagccatg     420
tggtcaaaat aatgccacga ataggggtg ctggaaaaac aactggaaca tcaccaccga      480
ctatgaagtc gacacgcccc ctgcgttcaa caccagagtg gtatgtcctt gctcataata     540
agtggctagc ctcgaagatc aggccaaaga ctgataggag ctcagtatga ccttcacatc     600
accaatgtca ccaactggct cggccctgat ggggttcgga agcctgccat gcttataaac     660
ggtgtgttgc cagagcccac aagatcctcc aaggtcactt ctgacaacaa ggcaggctca     720
ttccctggtc ccacaatctc agccgactgg ggcgactaca ttattgtcaa tgtccacaat     780
gacatgcaag ataacgggta agaaatgcag cacggtaccc ccggcatcct caaacctgct     840
tgctaacaca taggtagaac gtcaatccat tggcatggaa tccgtcagct tggcgagagc     900
aaccaggacg gcgcaaacgg cgtaacggaa tgccccattc ctcccggatc cagcaaaacc     960
tacgacttcc atgtgacgca gtacggcacc tcgtggtacc acagccacta ctccaaccag    1020
tacggcaatg gggtcgtggg cgccctgatc gtgcgcggcc cggcatcagc caactacgac    1080
atcgacctcg gtccctacct gatcagtgac tactactacg aaaccgcaga ccgcctccat    1140
ctccgagccg agctggtcag caacggccca ccgccagaca gcgacaacat cctgttccgc    1200
ggcaaaaaca tcaaccccaa gcgtgcaggc agcggctcct acgaccgcct cgtcctaacc    1260
cccggcaaga agcatctaat ccggctcatc aacgccagcg tggacaactc cttcgtcatc    1320
tccctcgtcg gccacaactt caccgtcatc tccaccgaca tggtccccat caccctgtc     1380 gtgcgcagct ccttattcat gggcgtcggc cagcggtacg acgtcattgt cgaagccaac    1440
cagcccgtgg gcaactactg gctcaacgcg acgctcgagg cccagaacaa ctgcgggcat    1500
tcggtcaacc cctccccgc ggctattgtc cagtacgagg cgccagctc caccgccctg      1560 ccgaccaacc gcgggacgcc cctgacggcg acatgcaatg cgagaaagg gttttcgccc     1620 attgttaagc ggacagtttc aagttccctg ttccagccgt ctaccctgcc agtcagcctt    1680
gaattcccca ctacagaccg cgggcaggtg tttgagtggc gggttaagaa cacgccgata    1740
```

-continued

```
agcgtcgaat gggagcatcc cgtgctggag tacattttgc aggggaacac ctccttcccg    1800
gcaaaggcca atctcattga agtcccgcag gcaaatgtct ggacgttctg ggtgattcag    1860
aacgggtttg gctgccgca cccgattcac ctgcatgggc atgatttcct ggtgcttggg    1920
gtcggcaacg ggactttga tgctgcgtct atgagggggc tgttgaattt taataatcct    1980
gttcgtaggg atgtcgagca gatgcctggc aatgggtggc tcgtgattgc gttcaagacg    2040
gataatccgg ggtgctggtt gatgcattgc catattggct ggcatgtggc tatgggctg    2100
gggatacagt ttttggaacg gaggagtgat atcctagcgc tcatgaagct ggatcagatg    2160
gtgcccaatt gtgaggcttg gagggcctat gcaaggacga gtccatatct gccaaagctt    2220
gattcggggc tgaaaagggg ggtggagatg agggagggga tggagccggc tgtgaggcgc    2280
attggttaga ttgaggtatc gtactcaact tgcttccaag ctggctatgg ctatgagtgg    2340
ttcaggaaga agagggaatc tcactattct tgcagcatgc ccaactaaga taaaaaggaa    2400
ctgaaaaaga actcacccat tgtgcgggtt gaacgacatg ggaccgcctg accgctgaag    2460
tgacatcatt actatcttca ccacgctgag cattcgaatt cccagacgcc cttggtagtg    2520
gccatttgga tggcttaccg tgactctgga cgaaagaggt gcgcaagact ccgcatggtc    2580
aggggtcata tcgccaatgg cgtcatcccg ccagggatta aggcagctca taaaccctac    2640
tttggtctct tgccttacaa cgccttcctg acattaggac atggaataga catcattact    2700
attgaagatg tttggacaca tgcaatgcgt actttgagtt gctatcaaaa agcatgaaac    2760
agcgatgtag gtgaggtact caatagatat ggcgtttaag cagaaatacc aatcatttca    2820
ggagataata accgtcaact cacgcagggc ttcaacgttg gagtggtgac gacaggcccc    2880
tgacgtcttg gttgctggag ggatcgtcag ggggttaaaaa taagggttag ggttcaagtc    2940
ttccgtcaac tccctaagga ggcaaggatc c                                    2971
```

<210> SEQ ID NO 43
<211> LENGTH: 611
<212> TYPE: PRT
<213> ORGANISM: Thielavia arenaria ALKO4197
<220> FEATURE:
<221> NAME/KEY: MISC_FEATURE
<222> LOCATION: (1)..(611)
<223> OTHER INFORMATION: Deduced amino acid sequence of Thielavia
      arenaria LAKO4197 TaLcc3
<220> FEATURE:
<221> NAME/KEY: MISC_FEATURE
<222> LOCATION: (1)..(611)
<223> OTHER INFORMATION: Deduced amino acid sequence of Thielavia
      arenaria ALKO4197 TaLcc3

<400> SEQUENCE: 43

Met Val Cys Leu Gln Tyr Gln Leu Thr Ala Ala Cys Phe Ala Val Leu
1               5                   10                  15

Ala Val Thr Thr Pro Ala Ser Cys Ser Pro Val Gln Pro Ser Pro
            20                  25                  30

Val His Asp Leu Leu Pro Arg Gln Thr Ile Ile Pro Gly Gly Lys Pro
        35                  40                  45

Cys Gly Gln Asn Asn Ala Thr Asn Arg Gly Cys Trp Lys Asn Asn Trp
    50                  55                  60

Asn Ile Thr Thr Asp Tyr Glu Val Asp Thr Pro Ala Phe Asn Thr
65                  70                  75                  80

Arg Val Tyr Asp Leu His Ile Thr Asn Val Thr Asn Trp Leu Gly Pro
                85                  90                  95

Asp Gly Val Arg Lys Pro Ala Met Leu Ile Asn Gly Ser Phe Pro Gly

-continued

```
            100                 105                 110
Pro Thr Ile Ser Ala Asp Trp Gly Asp Tyr Ile Ile Val Asn Val His
            115                 120                 125

Asn Asp Met Gln Asp Asn Gly Thr Ser Ile His Trp His Gly Ile Arg
130                 135                 140

Gln Leu Gly Glu Ser Asn Gln Asp Gly Ala Asn Gly Val Thr Glu Cys
145                 150                 155                 160

Pro Ile Pro Pro Gly Ser Ser Lys Thr Tyr Asp Phe His Val Thr Gln
                165                 170                 175

Tyr Gly Thr Ser Trp Tyr His Ser His Tyr Ser Asn Gln Tyr Gly Asn
            180                 185                 190

Gly Val Val Gly Ala Leu Ile Val Arg Gly Pro Ala Ser Ala Asn Tyr
            195                 200                 205

Asp Ile Asp Leu Gly Pro Tyr Leu Ile Ser Asp Tyr Tyr Tyr Glu Thr
            210                 215                 220

Ala Asp Arg Leu His Leu Arg Ala Glu Leu Val Ser Asn Gly Pro Pro
225                 230                 235                 240

Pro Asp Ser Asp Asn Ile Leu Phe Arg Gly Lys Asn Ile Asn Pro Lys
                245                 250                 255

Arg Ala Gly Ser Gly Ser Tyr Asp Arg Leu Val Leu Thr Pro Gly Lys
            260                 265                 270

Lys His Leu Ile Arg Leu Ile Asn Ala Ser Val Asp Asn Ser Phe Val
            275                 280                 285

Ile Ser Leu Val Gly His Asn Phe Thr Val Ile Ser Thr Asp Met Val
290                 295                 300

Pro Ile Thr Pro Val Val Arg Ser Ser Leu Phe Met Gly Val Gly Gln
305                 310                 315                 320

Arg Tyr Asp Val Ile Val Glu Ala Asn Gln Pro Val Gly Asn Tyr Trp
                325                 330                 335

Leu Asn Ala Thr Leu Glu Ala Gln Asn Asn Cys Gly His Ser Val Asn
            340                 345                 350

Pro Phe Pro Ala Ala Ile Val Gln Tyr Glu Gly Ala Ser Ser Thr Ala
            355                 360                 365

Leu Pro Thr Asn Arg Gly Thr Pro Leu Thr Ala Thr Cys Asn Gly Glu
370                 375                 380

Lys Gly Phe Ser Pro Ile Val Lys Arg Thr Val Ser Ser Ser Leu Phe
385                 390                 395                 400

Gln Pro Ser Thr Leu Pro Val Ser Leu Glu Phe Pro Thr Thr Asp Arg
                405                 410                 415

Gly Gln Val Phe Glu Trp Arg Val Lys Asn Thr Pro Ile Ser Val Glu
            420                 425                 430

Trp Glu His Pro Val Leu Glu Tyr Ile Leu Gln Gly Asn Thr Ser Phe
            435                 440                 445

Pro Ala Lys Ala Asn Leu Ile Glu Val Pro Gln Ala Asn Val Trp Thr
            450                 455                 460

Phe Trp Val Ile Gln Asn Gly Phe Gly Leu Pro His Pro Ile His Leu
465                 470                 475                 480

His Gly His Asp Phe Leu Val Leu Gly Val Gly Asn Gly Thr Phe Asp
                485                 490                 495

Ala Ala Ser Met Arg Gly Leu Leu Asn Phe Asn Asn Pro Val Arg Arg
            500                 505                 510

Asp Val Glu Gln Met Pro Gly Asn Gly Trp Leu Val Ile Ala Phe Lys
            515                 520                 525
```

-continued

```
Thr Asp Asn Pro Gly Cys Trp Leu Met His Cys His Ile Gly Trp His
    530                 535                 540
Val Ala Met Gly Leu Gly Ile Gln Phe Leu Glu Arg Arg Ser Asp Ile
545                 550                 555                 560
Leu Ala Leu Met Lys Leu Asp Gln Met Val Pro Asn Cys Glu Ala Trp
                565                 570                 575
Arg Ala Tyr Ala Arg Thr Ser Pro Tyr Leu Pro Lys Leu Asp Ser Gly
            580                 585                 590
Leu Lys Arg Gly Val Glu Met Arg Glu Gly Met Glu Pro Ala Val Arg
        595                 600                 605
Arg Ile Gly
    610

<210> SEQ ID NO 44
<211> LENGTH: 2731
<212> TYPE: DNA
<213> ORGANISM: Thielavia arenaria ALKO4197
<220> FEATURE:
<221> NAME/KEY: misc_feature
<222> LOCATION: (1)..(2731)
<223> OTHER INFORMATION: Nucleotide sequence of Thielavia arenaria
      ALKO4197 Talcc4 gene
<220> FEATURE:
<221> NAME/KEY: misc_feature
<222> LOCATION: (455)..(2247)
<220> FEATURE:
<221> NAME/KEY: Intron
<222> LOCATION: (1371)..(1442)

<400> SEQUENCE: 44
ggatccggga aggtgactga gaagatgtcc acgctatggc ctcgccgtgt ctcaaagaga      60
tggcgttctc tggctcgtga tgttcggatt tgacgacggc ggtgattggc aacgactttg     120
cgggacgttg gatttggaca cttgggggt tgacaatgg cgagagcgag acaagtaggt       180
actaaccgct ttcctccagg atttctgtgc tgggaggcgc cagggaggcg ggctgacgat     240
ggacttggtt acaagggagt gaagatgtgg cttacaggga cgtacatcta ctatataagc     300
tgaacactgt ggcacttctc tgagaaaagc aatgggcagg tatctcagta catgttcagg     360
accccttaag ttgaccattt caacttacat gcttcttcca actcgttcct ccctcgtcgg     420
cccttggaag tttagaccgg gctcttacat gacaatgatt tcgcgtcttc ttttcacaag     480
cagtttcact gctacactgg cttctgctct gccaggtcta ttatacgccc ctcattcaag     540
cgcactgctg gctcgttcct cctgtagcgg caatacggcg tcaacccggt cccagtggtg     600
cgactactcc atcgacaccg actatacgac agagcccgtt gacaccgggg ttactcgaga     660
gtactggctt gagttaacgg acgtaaccgt gtcgccagac ggggtgtcgc ggtcagcgat     720
ggctgtcaat ggctccatcc ctggtccaac catcttcgct gactggggtg ataccgtcgt     780
cgttcacgtc accaactcgt tatccacttc tctgaacgga acaagcatcc actggcatgg     840
catccgccaa aactacacca accagaacga cggtgttgcc tccattacgc agtgtcctct     900
ggcggttggc gaatcaacca cctacacctg gaaagcaaca caatatggct catcttggta     960
ccattctcac ttcagccttc aggcctggga aggcgtcttt ggtgggatca tcatcaatgg    1020
tccttctacc gccaactatg acgaggatct tggcatgctt ttcctcaatg attgggatca    1080
ccaaactgtc gatgagctct attccagtgc tgaaacctct gggccacca ccttggccaa    1140 cggtctcatc aacggtacga acgtctacgg ggaagatggt gattcatccc agaccggaac    1200
aagattggct gtctcattca cgtctggcac ctcataccgc atgcggctgg tgaatgccgc    1260
```

-continued

```
cgtcgacacg cattggaaat tctccatcgg caaccacaca atgactgtga tggccgctga    1320
tctcgttccg attgagccat atgaaacgac ggtcttaaca attgggatgg gtaagtacct    1380
acatcatcag accacctact tattcggttt cttaggacac ccgagactga gttccacata    1440
ggacaaagat acgacatagt cgtcacggca gatcaagctg atgtcgcgga taacttctgg    1500
atgagggcta tcccacaatc agcatgctct gataacgaca gcgccgacaa tatcagaggg    1560
atcgtctact atggtgatag tcccggcacc ccttcaacaa ctggctacga cttcgaggac    1620
gcctgcgatg atgagacggc caacatcacc ccttacatct ccaagacggt ttcttcagca    1680
gaatggaatg acttggaaac tgcctcagtc tctaggaact cggccggcct tttcaaatgg    1740
tatctcaaca gcacgaccat gctagttgac tgggcaaaac ccactctcga gatggtgacg    1800
gacaacgtga ccgaatacga ttcggatgac gccatcattg agctgaatga agccaaccag    1860
tgggtgtaca tggtggttca acaacgctc caggttccac acccaatcca tctgcacggt    1920
cacgatttct tcattctcgc ccaaggttca gggacatacg attcgtcgac agtaacattg    1980
aagacggata acccacccag acgcgacacg gccatgctgc catcgcaggg atacttggtc    2040
atggcctggg agacggacaa ccctggcgtt tggctgatgc actgtcacat cggttggcat    2100
acctcagagg gcttcgccct ccagttcatt gagcggaaga gcgagatcgc gtcgatcgtc    2160
agtacgtcga ctatgaaaga tatttgcacc aagtgggagg agtttcagga ggaatattca    2220
attgaacaag aagactctgg tgtatgagat ggatgtgcgt tgaccatttt gcgtcaaaga    2280
catcctgcct gtcggtaact ctgatttgcc gtgtgaactt ggtttactag gtatttacag    2340
atacctacat cattggacat gtacataagg tacttaagta tccccgtat gcatctgtca    2400 tctgtcaagt catcctcaac cgttctagcc catcatgcac gtatgtacat gaatgtaatg    2460
atggaaccta gcacattagc aacagtttgc aaacgagtat cggcatggtc ctaagagtca    2520
tgattagggg gcagcgcagg ttcgacttgt tgtttataca gttaatcgtg cgcccccggt    2580
tacatattat gtaccctgct tacacatcca tatatactaa ggtgcttgag gtcgttgtac    2640
cgctgttgag ctcctagcat tcattccagg gagcgtggca atgactggta tgtctgtggg    2700
cgcgggcgta gatggtgggg tgggagatat c                                   2731
```

<210> SEQ ID NO 45
<211> LENGTH: 573
<212> TYPE: PRT
<213> ORGANISM: Thielavia arenaria ALKO4197
<220> FEATURE:
<221> NAME/KEY: MISC_FEATURE
<222> LOCATION: (1)..(573)
<223> OTHER INFORMATION: Deduced amino acid sequence of Thielavia
      arenaria ALKO4197 TaLcc4

<400> SEQUENCE: 45

```
Met Ile Ser Arg Leu Leu Phe Thr Ser Ser Phe Thr Ala Thr Leu Ala
1               5                   10                  15

Ser Ala Leu Pro Gly Leu Leu Tyr Ala Pro His Ser Ser Ala Leu Leu
            20                  25                  30

Ala Arg Ser Ser Cys Ser Gly Asn Thr Ala Ser Thr Arg Ser Gln Trp
        35                  40                  45

Cys Asp Tyr Ser Ile Asp Thr Asp Tyr Thr Thr Glu Pro Val Asp Thr
    50                  55                  60

Gly Val Thr Arg Glu Tyr Trp Leu Glu Leu Thr Asp Val Thr Val Ser
65                  70                  75                  80
```

-continued

```
Pro Asp Gly Val Ser Arg Ser Ala Met Ala Val Asn Gly Ser Ile Pro
                85                  90                  95

Gly Pro Thr Ile Phe Ala Asp Trp Gly Asp Thr Val Val His Val
            100                 105                 110

Thr Asn Ser Leu Ser Thr Ser Leu Asn Gly Thr Ser Ile His Trp His
            115                 120                 125

Gly Ile Arg Gln Asn Tyr Thr Asn Gln Asn Asp Gly Val Ala Ser Ile
        130                 135                 140

Thr Gln Cys Pro Leu Ala Val Gly Glu Ser Thr Thr Tyr Thr Trp Lys
145                 150                 155                 160

Ala Thr Gln Tyr Gly Ser Ser Trp Tyr His Ser His Phe Ser Leu Gln
                165                 170                 175

Ala Trp Glu Gly Val Phe Gly Gly Ile Ile Asn Gly Pro Ser Thr
            180                 185                 190

Ala Asn Tyr Asp Glu Asp Leu Gly Met Leu Phe Leu Asn Asp Trp Asp
        195                 200                 205

His Gln Thr Val Asp Glu Leu Tyr Ser Ser Ala Glu Thr Ser Gly Pro
    210                 215                 220

Pro Thr Leu Ala Asn Gly Leu Ile Asn Gly Thr Asn Val Tyr Gly Glu
225                 230                 235                 240

Asp Gly Asp Ser Ser Gln Thr Gly Thr Arg Leu Ala Val Ser Phe Thr
                245                 250                 255

Ser Gly Thr Ser Tyr Arg Met Arg Leu Val Asn Ala Ala Val Asp Thr
            260                 265                 270

His Trp Lys Phe Ser Ile Gly Asn His Thr Met Thr Val Met Ala Ala
        275                 280                 285

Asp Leu Val Pro Ile Glu Pro Tyr Glu Thr Thr Val Leu Thr Ile Gly
    290                 295                 300

Met Gly Gln Arg Tyr Asp Ile Val Val Thr Ala Asp Gln Ala Asp Val
305                 310                 315                 320

Ala Asp Asn Phe Trp Met Arg Ala Ile Pro Gln Ser Ala Cys Ser Asp
                325                 330                 335

Asn Asp Ser Ala Asp Asn Ile Arg Gly Ile Val Tyr Tyr Gly Asp Ser
            340                 345                 350

Pro Gly Thr Pro Ser Thr Thr Gly Tyr Asp Phe Glu Asp Ala Cys Asp
        355                 360                 365

Asp Glu Thr Ala Asn Ile Thr Pro Tyr Ile Ser Lys Thr Val Ser Ser
    370                 375                 380

Ala Glu Trp Asn Asp Leu Glu Thr Ala Ser Val Ser Arg Asn Ser Ala
385                 390                 395                 400

Gly Leu Phe Lys Trp Tyr Leu Asn Ser Thr Thr Met Leu Val Asp Trp
                405                 410                 415

Ala Lys Pro Thr Leu Glu Met Val Thr Asp Asn Val Thr Glu Tyr Asp
            420                 425                 430

Ser Asp Asp Ala Ile Ile Glu Leu Asn Glu Ala Asn Gln Trp Val Tyr
        435                 440                 445

Met Val Val Gln Thr Thr Leu Gln Val Pro His Pro Ile His Leu His
    450                 455                 460

Gly His Asp Phe Phe Ile Leu Ala Gln Gly Ser Gly Thr Tyr Asp Ser
465                 470                 475                 480

Ser Thr Val Thr Leu Lys Thr Asp Asn Pro Pro Arg Arg Asp Thr Ala
                485                 490                 495

Met Leu Pro Ser Gln Gly Tyr Leu Val Met Ala Trp Glu Thr Asp Asn
```

-continued

```
                       500                 505                 510
    Pro Gly Val Trp Leu Met His Cys His Ile Gly Trp His Thr Ser Glu
            515                 520                 525

Gly Phe Ala Leu Gln Phe Ile Glu Arg Lys Ser Glu Ile Ala Ser Ile
            530                 535                 540

Val Ser Thr Ser Thr Met Lys Asp Ile Cys Thr Lys Trp Glu Glu Phe
    545                 550                 555                 560

Gln Glu Glu Tyr Ser Ile Glu Gln Glu Asp Ser Gly Val
                    565                 570

<210> SEQ ID NO 46
<211> LENGTH: 2954
<212> TYPE: DNA
<213> ORGANISM: Chaetomium thermophilum ALKO4265
<220> FEATURE:
<221> NAME/KEY: misc_feature
<222> LOCATION: (1)..(2954)
<223> OTHER INFORMATION: Nucleotide sequence of Chaetomium thermophilum
      ALKKO4265 Ctlcc1 gene
<220> FEATURE:
<221> NAME/KEY: misc_feature
<222> LOCATION: (1)..(2954)
<223> OTHER INFORMATION: Nucleotide sequence of Chaetomium thermophilum
      ALKO4265 Ctlcc1 gene
<220> FEATURE:
<221> NAME/KEY: misc_feature
<222> LOCATION: (371)..(2497)
<223> OTHER INFORMATION: Ctlcc1
<220> FEATURE:
<221> NAME/KEY: Intron
<222> LOCATION: (581)..(630)
<220> FEATURE:
<221> NAME/KEY: Intron
<222> LOCATION: (710)..(762)
<220> FEATURE:
<221> NAME/KEY: Intron
<222> LOCATION: (775)..(824)
<220> FEATURE:
<221> NAME/KEY: Intron
<222> LOCATION: (895)..(949)
<220> FEATURE:
<221> NAME/KEY: Intron
<222> LOCATION: (1992)..(2086)

<400> SEQUENCE: 46
ttcccgaagg cttcaactca cactcggtcc tcactccaac caagcctgtc gtatacacga      60
actcgtcccg cgtctaccgg gcgaggttgc tgcacctgcc ttgacgacat tccgaatctg     120
ggaactaaga cggcatcacc gtcgatatat tggataggat ccgagttttc gcgatctttg     180
ttgccttcac tgaggagaag gtgcactctg ggtgttgagt ctgtcgtcta tataacgacc     240
agaccttgcg acagtgagtt gactccagtt cttcatcgtc accatcagca tcagacgctt     300
cagtgtcttg agcctcgttc ttttaacaaa tcgctcactc aatcatagtt ggcttggtgc     360
catcagcatc atgaagttcc taacctatgc caccgccctc ctgggtgccc ttacagccgt     420
cgtaggggca atcccaactc gttctggcac caagaaaaag tacattagag atggccctgg     480
accctgccat accccaagta atcgggcatg ctgggcccct gggttcgaca tcaatactga     540
ctacgaagtc aacacaccca acgggtgt tacccgcaat gtaagtcttc atcgttacta       600
gtgcagtgaa tttcgtgctg acagaggtag tacactctca ctctgacgga ggaagacaac     660
tggaccggcc cggatggggt ggtcaaggaa aagattatgc tggttaatgg tatgtcagcc     720
cctgagctag gtatgatatg atgactaacc atatatgtgc aggcaaaact ttaggtatgt     780
ctctcctggt gaagttaagc tagatgatgt actaacctat gcaggccga ccattgaggc      840
```

```
caactggggt gactggatcg aagtcaaggt catcaataac ctcttgacta atgggtatgt    900
cttgttcttc cccctttagt ggagtgccca agctgactga ctcccataga acttccatcc    960
actggcacgg cattcaccag aagggcagta accttcacga cggtgccaac ggcgttactg   1020
aatgccccat ccctcccaac ggtggccagc gcacctatcg cttccgtgcc cagcagtatg   1080
gcaccagctg gtaccactct cacttctctg ctcagtatgg caatggcatc gtcggtccca   1140
tcgttatcca cggtccagct tctctgccct atgacatcga ccttggcccc ttccctctta   1200
cggactacta ctacaagagc gcggatgagc tggtgcgcca cactcagaac aacggcccac   1260
cgttcagcga caacgtcctc ttcaacggca ccggcgttca tccccagact ggccatggtc   1320
agtatgctaa ggtgaccctg accccgggca agcgtcaccg cctgcgcatc atcaacatgt   1380
cgacggagaa ccacttccag gtctctctcg tcggccacca gttcaccgtc attgccgctg   1440
acatggtccc cgtccactcc tacactactg acagcctgtt tctcgctgtc gggcagcgtt   1500
atgatgtcac catcgacgct tcgcagaccc ccggtaacta ctggttcaac gtcacctttg   1560
gcggcggttt cgcttgcggt ggttccttca accctaaccc agctgccatc ttccactatg   1620
agggtgcccc cgatgctctg ccgactgacc ctggtgttcc tccgcgcgac cacaactgct   1680
tggacactct ggatctcgtc cctgtcgtac ctcgtaatgt tcaggtcaac cagttcgtca   1740
agaagcctga gaacaccctg cctgttgagc tgtcccttgg tggtacccg ctcttcgttt    1800
ggaaggtcaa cggcagcgcc attgatgttg actggggcaa ccccgtcctt cagtatgtga   1860
tggaccgcaa caccagctac cgccaagccg acaacatcgt cgaggttaat ggtgtcaacc   1920
agtggactta ctggctgatt gagaacgacc ccaatggtgc cttcagcctg ccccaccccc   1980
tgcatcttca cgtaagttat ttccctcttt ctcttttacc tacccccctt tattgcagat   2040
tagtcccttc tttagcccat atctcagata actaacctcc ttccagggcc acgacttcct   2100
cattgtcggc cgctcccccg acgtcccgcc gggctcgaac cagcgctaca acttcgaccc   2160
cgccaccgac atctaccgcc tgcgcggtca gaacccgacc cgtcgtgacg tcgccatgct   2220
tcctgccggc ggctggctgc tgctcgcctt cctcaccgac aaccccggtg cctggctctt   2280
ccactgccac attgcttggc acgtgtcggg cggtctgtct gtcgacttcc tcgagcggcc   2340
gaacgacctg cgcaacagca tcctccagca tgataaggac gagttcaacc gcgtgtgcaa   2400
tgagtggcgc acgtactggc taatagtcc ccatcctaag attgactctg gtttgaagca    2460
ccgctgggtt gaggagagtg agtggctggt tcgatagggg gtgttgtgca gagttggggt   2520
gtgatttggg tcatgggttt tgagcgttgg gatatgggcg ttgataatca ttaatgtgtt   2580
ttggttgggc atatttcgga gttttggcta tcggttatcg tagtggtcaa tagtagtcaa   2640
cccttctcta tcgtcaatag taatcaaccc ttctctacac aatttgatat cgtgacgttg   2700
atgacttggg actgaaggcc aaacttaagt tgggccattt ttccggctct tttcctcatg   2760
tgataggtaa atgagcctag tttgaactat gtgtgctgtt cagcactcac tgcactatgt   2820
acagccaaga tgtccccaag tgttcgatat gtcaagttcc agcattgacg atcagctctc   2880
tatgttatca ctttgcactc gctttttta tgctaatgtc ctctaccact gaaaatccct    2940
agccctgcca ccgg                                                      2954
```

<210> SEQ ID NO 47
<211> LENGTH: 607
<212> TYPE: PRT
<213> ORGANISM: Chaetomium thermophilum ALKO4265
<220> FEATURE:
<221> NAME/KEY: MISC_FEATURE
<222> LOCATION: (1)..(607)
<223> OTHER INFORMATION: Deduced amino acid sequence of Chaetomium
      thermophilum ALKO4265 CtLcc1

<400> SEQUENCE: 47

```
Met Lys Phe Leu Thr Tyr Ala Thr Ala Leu Leu Gly Ala Leu Thr Ala
1               5                   10                  15

Val Val Gly Ala Ile Pro Thr Arg Ser Gly Thr Lys Lys Lys Tyr Ile
            20                  25                  30

Arg Asp Gly Pro Gly Pro Cys His Thr Pro Ser Asn Arg Ala Cys Trp
        35                  40                  45

Ala Pro Gly Phe Asp Ile Asn Thr Asp Tyr Glu Val Asn Thr Pro Asn
    50                  55                  60

Thr Gly Val Thr Arg Asn Tyr Thr Leu Thr Leu Thr Glu Glu Asp Asn
65                  70                  75                  80

Trp Thr Gly Pro Asp Gly Val Val Lys Glu Lys Ile Met Leu Val Asn
                85                  90                  95

Gly Lys Thr Leu Gly Pro Thr Ile Glu Ala Asn Trp Gly Asp Trp Ile
            100                 105                 110

Glu Val Lys Val Ile Asn Asn Leu Leu Thr Asn Gly Thr Ser Ile His
        115                 120                 125

Trp His Gly Ile His Gln Lys Gly Ser Asn Leu His Asp Gly Ala Asn
    130                 135                 140

Gly Val Thr Glu Cys Pro Ile Pro Pro Asn Gly Gly Gln Arg Thr Tyr
145                 150                 155                 160

Arg Phe Arg Ala Gln Gln Tyr Gly Thr Ser Trp Tyr His Ser His Phe
                165                 170                 175

Ser Ala Gln Tyr Gly Asn Gly Ile Val Gly Pro Ile Val Ile His Gly
            180                 185                 190

Pro Ala Ser Leu Pro Tyr Asp Ile Asp Leu Gly Pro Phe Pro Leu Thr
        195                 200                 205

Asp Tyr Tyr Tyr Lys Ser Ala Asp Glu Leu Val Arg His Thr Gln Asn
    210                 215                 220

Asn Gly Pro Pro Phe Ser Asp Asn Val Leu Phe Asn Gly Thr Gly Val
225                 230                 235                 240

His Pro Gln Thr Gly His Gly Gln Tyr Ala Lys Val Thr Leu Thr Pro
                245                 250                 255

Gly Lys Arg His Arg Leu Arg Ile Ile Asn Met Ser Thr Glu Asn His
            260                 265                 270

Phe Gln Val Ser Leu Val Gly His Gln Phe Thr Val Ile Ala Ala Asp
        275                 280                 285

Met Val Pro Val His Ser Tyr Thr Thr Asp Ser Leu Phe Leu Ala Val
    290                 295                 300

Gly Gln Arg Tyr Asp Val Thr Ile Asp Ala Ser Gln Thr Pro Gly Asn
305                 310                 315                 320

Tyr Trp Phe Asn Val Thr Phe Gly Gly Gly Phe Ala Cys Gly Gly Ser
                325                 330                 335

Phe Asn Pro Asn Pro Ala Ala Ile Phe His Tyr Glu Gly Ala Pro Asp
            340                 345                 350

Ala Leu Pro Thr Asp Pro Gly Val Pro Pro Arg Asp His Asn Cys Leu
        355                 360                 365

Asp Thr Leu Asp Leu Val Pro Val Pro Arg Asn Val Gln Val Asn
    370                 375                 380

Gln Phe Val Lys Lys Pro Glu Asn Thr Leu Pro Val Glu Leu Ser Leu
```

```
                385                 390                 395                 400
Gly Gly Thr Pro Leu Phe Val Trp Lys Val Asn Gly Ser Ala Ile Asp
            405                 410                 415
Val Asp Trp Gly Asn Pro Val Leu Gln Tyr Val Met Asp Arg Asn Thr
            420                 425                 430
Ser Tyr Arg Gln Ala Asp Asn Ile Val Glu Val Asn Gly Val Asn Gln
            435                 440                 445
Trp Thr Tyr Trp Leu Ile Glu Asn Asp Pro Asn Gly Ala Phe Ser Leu
    450                 455                 460
Pro His Pro Met His Leu His Gly His Asp Phe Leu Ile Val Gly Arg
465                 470                 475                 480
Ser Pro Asp Val Pro Pro Gly Ser Asn Gln Arg Tyr Asn Phe Asp Pro
                485                 490                 495
Ala Thr Asp Ile Tyr Arg Leu Arg Gly Gln Asn Pro Thr Arg Arg Asp
            500                 505                 510
Val Ala Met Leu Pro Ala Gly Gly Trp Leu Leu Leu Ala Phe Leu Thr
            515                 520                 525
Asp Asn Pro Gly Ala Trp Leu Phe His Cys His Ile Ala Trp His Val
530                 535                 540
Ser Gly Gly Leu Ser Val Asp Phe Leu Glu Arg Pro Asn Asp Leu Arg
545                 550                 555                 560
Asn Ser Ile Leu Gln His Asp Lys Asp Glu Phe Asn Arg Val Cys Asn
                565                 570                 575
Glu Trp Arg Thr Tyr Trp Pro Asn Ser Pro His Pro Lys Ile Asp Ser
            580                 585                 590
Gly Leu Lys His Arg Trp Val Glu Glu Ser Glu Trp Leu Val Arg
            595                 600                 605

<210> SEQ ID NO 48
<211> LENGTH: 2516
<212> TYPE: DNA
<213> ORGANISM: Chaetomium thermophilum ALKO4265
<220> FEATURE:
<221> NAME/KEY: misc_feature
<222> LOCATION: (1)..(2516)
<223> OTHER INFORMATION: Nucleotide sequence of Chaetomium thermophilum
      ALKO4265 Ctlcc2 gene
<220> FEATURE:
<221> NAME/KEY: Misc_feature
<222> LOCATION: (246)..(2231)
<223> OTHER INFORMATION: Ctlcc2
<220> FEATURE:
<221> NAME/KEY: Intron
<222> LOCATION: (483)..(531)
<220> FEATURE:
<221> NAME/KEY: Intron
<222> LOCATION: (608)..(668)
<220> FEATURE:
<221> NAME/KEY: Intron
<222> LOCATION: (751)..(829)

<400> SEQUENCE: 48
tctagaagat atcggcagtc gcggtagctt gaatcatgag cggggatata cgagagaggg      60
agcagcccct cgggtaacat gcggatgaga acatggcagc atcatcgatt cctacgtcta     120
tatcttggag acgtataaga ggaagtggtg atgacgataa tcgtggagat ctactgaccg     180
ctctctcacg gcatattatg aattcgtgac tttatccctc tctgacgtgg tttctgacaa     240
ctgccatgcc agacgtagt ctcatactcc ttctcctcgc cttccttggg ctcctacact      300
taaccctagc aaaccccatc aaggcaaacc caaacccctt cctcctagcc agacaaacca     360
```

-continued

```
tcacccctgg aggccagccc tgtggccaac atggcccaga gaacagactc tgttggcgaa    420
acctttggaa tatcagtact gatccggacg tcagcatccc ccctgcctac aacaatcgat    480
atgtaagtct cctcaagcct ctgaatacta gtcgtcactg acatcatcca gtatgatttg    540
cacatcacca atgagacaaa ctggctaggg ccagacggcg tgcggaagca cgctatgctc    600
atcaacagtc agtccccctt ggccgtgacc ccctccctta tcttctgtca gagggctaac    660
aaccccagat caatttcccg gccctaccat gaagcagaa tggggtgact atatcgtagt     720
gaatgtctac aatgacctgg aggacaacgg gtaagcctct cttcctcatt tgggctactc    780
gcctaacacc gtcaacaact taccccctcac taccgctgac tccatccagg acatccatcc   840
attggcatgg catccgccaa ttcggcgaaa gcaaccaaga tggcaccaat ggcgtcaccg    900
agtgccccat tccaccgggg cacatgaaaa catacagttt ccacgtcact cagtacggaa    960
cgtcctggta ccacagccac ttctccaacc agtacggcaa cggcgtgctc ggcgcactgg   1020
tggtcaaagg cccggcttcc gccaactacg acatcgacct cggcccgtac atcattagcg   1080
actactacca cgagacggcc gacagattac atctccaggc agagctactc cgcaacgggc   1140
cccctccaga cagcgacaac atcctcttca ggggcaagaa catcaaccct gacggctcgg   1200
gccgcggctc ttatgaccga ttaaccctca tcccaggcaa gaaacacctg ctgcgtctga   1260
tcaacgcaag cgtggataac tccttcacgg tctcccctcgt gggacacaac ttcacggtca  1320
ttgcgaccga tatggtcccg gtccagccaa ccgtccgcag gagcctgttc atggccgtcg   1380
gccagcgtta tgatgttatt gttaccgccg accagcccgt agataattat tggctgaacg   1440
tcaccctgga agcaaacaac aactgcggcc gctctcgcaa cccctaccca gcagccatca   1500
tccactacga gggagccagc ccaaccgccc tccccaccaa ccgtggcacc cccctcgtag   1560
caacctgcac cggcgagaca ggcttcaccc ccgtcgtgcc gcggaatatc ccccccaact   1620
tcttccgccc ttccgacatc gcctccaata ccctgccaat cggcctcaac attgtcaacc   1680
acaccactaa aggccaaatc ttctcctggc atgtgaagaa cacgcctatt tccgtggaat   1740
gggggcatcc agtattagag tacatcctcg aagggaatta ctccttttccc gcagcggtta   1800
atctgattca actcaaccaa aaagacacct ggacactctt tttggtgcat agttcgttat   1860
cattaccgca cccaatccac ctccacggac acgacttcct cgtcctgggc ctgggcagcg   1920
gcacctttga tcctcagaca catctccccct tgctaaacta ctcaaacccc gtccggcgag   1980
acgttgaaca gctcccccggc ttggggtggg ccgccatcgc gttcaagacg ataaacccgg   2040
gcgtgtggct catgcactgc catattgggt ggcatgtggc gatggggctg ggggtgcagt   2100
ttttggagag agcgagcgag atgagggtgc tgatgaagct ggatcaggtg gtgccgaatt   2160
gtaacgcgtg gagggagtac gaacgggtgg ggaattggtt gcctagggg gatacggatt    2220
cggggttgtg aggggggtgaa gagtgaggat gggcggacgg tagacgtctg gttatcagcc   2280
tggggatcgc atcatggccg gtagatcctt tcatcttgga tccgcttatg ttgtcatttg   2340
actgggatgc tgcgcagtag aggctgagct ctgttaacgc cagtgtgtaa aactcagcag   2400
agtgccattt tgaggcattg tgagatgttc ggaccactat cacacacctt aacattcgat   2460
agccttacgt taaggtgctt gatcatggcc tgaggatgtc gtcaccattg ttccca        2516
```

```
<210> SEQ ID NO 49
<211> LENGTH: 598
<212> TYPE: PRT
<213> ORGANISM: Chaetomium thermophilum ALKO4265
<220> FEATURE:
<221> NAME/KEY: MISC_FEATURE
```

<222> LOCATION: (1)..(598)
<223> OTHER INFORMATION: Deduced amino acid sequence of Chaetomium
      thermophilum ALKO4265 CtLcc2

<400> SEQUENCE: 49

```
Met Pro Arg Arg Ser Leu Ile Leu Leu Leu Ala Phe Leu Gly Leu
1               5                   10                  15

Leu His Leu Thr Leu Ala Asn Pro Ile Lys Ala Asn Pro Asn Pro Phe
        20                  25                  30

Leu Leu Ala Arg Gln Thr Ile Thr Pro Gly Gly Gln Pro Cys Gly Gln
            35                  40                  45

His Gly Pro Glu Asn Arg Leu Cys Trp Arg Asn Leu Trp Asn Ile Ser
        50                  55                  60

Thr Asp Pro Asp Val Ser Ile Pro Pro Ala Tyr Asn Asn Arg Tyr Tyr
65                  70                  75                  80

Asp Leu His Ile Thr Asn Glu Thr Asn Trp Leu Gly Pro Asp Gly Val
                85                  90                  95

Arg Lys His Ala Met Leu Ile Asn Asn Gln Phe Pro Gly Pro Thr Ile
            100                 105                 110

Glu Ala Glu Trp Gly Asp Tyr Ile Val Val Asn Val Tyr Asn Asp Leu
            115                 120                 125

Glu Asp Asn Gly Thr Ser Ile His Trp His Gly Ile Arg Gln Phe Gly
130                 135                 140

Glu Ser Asn Gln Asp Gly Thr Asn Gly Val Thr Glu Cys Pro Ile Pro
145                 150                 155                 160

Pro Gly His Met Lys Thr Tyr Ser Phe His Val Thr Gln Tyr Gly Thr
                165                 170                 175

Ser Trp Tyr His Ser His Phe Ser Asn Gln Tyr Gly Asn Gly Val Leu
            180                 185                 190

Gly Ala Leu Val Val Lys Gly Pro Ala Ser Ala Asn Tyr Asp Ile Asp
            195                 200                 205

Leu Gly Pro Tyr Ile Ile Ser Asp Tyr Tyr His Glu Thr Ala Asp Arg
        210                 215                 220

Leu His Leu Gln Ala Glu Leu Leu Arg Asn Gly Pro Pro Asp Ser
225                 230                 235                 240

Asp Asn Ile Leu Phe Arg Gly Lys Asn Ile Asn Pro Asp Gly Ser Gly
                245                 250                 255

Arg Gly Ser Tyr Asp Arg Leu Thr Leu Ile Pro Gly Lys Lys His Leu
            260                 265                 270

Leu Arg Leu Ile Asn Ala Ser Val Asp Asn Ser Phe Thr Val Ser Leu
        275                 280                 285

Val Gly His Asn Phe Thr Val Ile Ala Thr Asp Met Val Pro Val Gln
    290                 295                 300

Pro Thr Val Arg Arg Ser Leu Phe Met Ala Val Gly Gln Arg Tyr Asp
305                 310                 315                 320

Val Ile Val Thr Ala Asp Gln Pro Val Asp Asn Tyr Trp Leu Asn Val
                325                 330                 335

Thr Leu Glu Ala Asn Asn Asn Cys Gly Arg Ser Arg Asn Pro Tyr Pro
            340                 345                 350

Ala Ala Ile Ile His Tyr Glu Gly Ala Ser Pro Thr Ala Leu Pro Thr
        355                 360                 365

Asn Arg Gly Thr Pro Leu Val Ala Thr Cys Thr Gly Glu Thr Gly Phe
    370                 375                 380

Thr Pro Val Val Pro Arg Asn Ile Pro Pro Asn Phe Phe Arg Pro Ser
```

```
                385                 390                 395                 400
Asp Ile Ala Ser Asn Thr Leu Pro Ile Gly Leu Asn Ile Val Asn His
                405                 410                 415
Thr Thr Lys Gly Gln Ile Phe Ser Trp His Val Lys Asn Thr Pro Ile
                420                 425                 430
Ser Val Glu Trp Gly His Pro Val Leu Glu Tyr Ile Leu Glu Gly Asn
            435                 440                 445
Tyr Ser Phe Pro Ala Ala Val Asn Leu Ile Gln Leu Asn Gln Lys Asp
        450                 455                 460
Thr Trp Thr Leu Phe Leu Val His Ser Ser Leu Ser Leu Pro His Pro
465                 470                 475                 480
Ile His Leu His Gly His Asp Phe Leu Val Leu Gly Leu Gly Ser Gly
                485                 490                 495
Thr Phe Asp Pro Gln Thr His Leu Pro Leu Leu Asn Tyr Ser Asn Pro
            500                 505                 510
Val Arg Arg Asp Val Glu Gln Leu Pro Gly Leu Gly Trp Ala Ala Ile
        515                 520                 525
Ala Phe Lys Thr Asp Asn Pro Gly Val Trp Leu Met His Cys His Ile
    530                 535                 540
Gly Trp His Val Ala Met Gly Leu Gly Val Gln Phe Leu Glu Arg Ala
545                 550                 555                 560
Ser Glu Met Arg Val Leu Met Lys Leu Asp Gln Val Val Pro Asn Cys
                565                 570                 575
Asn Ala Trp Arg Glu Tyr Glu Val Gly Asn Trp Leu Pro Arg Gly
            580                 585                 590
Asp Thr Asp Ser Gly Leu
        595

<210> SEQ ID NO 50
<211> LENGTH: 3025
<212> TYPE: DNA
<213> ORGANISM: Chaetomium thermophilum ALKO4265
<220> FEATURE:
<221> NAME/KEY: misc_feature
<222> LOCATION: (1)..(3025)
<223> OTHER INFORMATION: Nucleotide sequence of Chaetomium thermophilum
      ALKO4265
<220> FEATURE:
<221> NAME/KEY: Intron
<222> LOCATION: (711)..(768)
<223> OTHER INFORMATION: Intron 1
<220> FEATURE:
<221> NAME/KEY: Intron
<222> LOCATION: (1326)..(1390)
<223> OTHER INFORMATION: Intron 2
<220> FEATURE:
<221> NAME/KEY: Intron
<222> LOCATION: (2187)..(2255)
<223> OTHER INFORMATION: Intron 3

<400> SEQUENCE: 50
ccgcggctga tactaccaga aaacgcccca gttacacata tacacgccgg gaatctctgt      60
acaggttgtc tcaactgtgt cggttccgct cctgggaacg acattagcac cacctctttg     120
agccgtcata atattttct ttcttctttt ccccgtgct acgcaatcca gacaaccctg       180
gcaaagattg cctattgaga gctgggaaac tgccaagatg gcaacgctga ccggcgatca     240
tctgtcgaga cagcattaac gctcaacagc caccggcaac catccctaga cactgccaac     300
ttgctgccgt gtgccctgca ctacatgtgg cgtgacatgg atacgatgtt ttcggatatc     360
cagaaagctt catccgccga taggtctgct atctctctct tttctgccct ttcctgtctt     420
```

```
ttccaggacc ccctaaaatt tcatatgctc tcacatcggg gccagcatat ctattccatg    480
tctcccggtt ccatggtctt catcacccgt cacagattct gttccttctg ttattgcttc    540
ttactggcag agtgtgttgg cttgtggtga aagaccacct gctgcccctt cctagccatc    600
atgggggtca ttttggagga tttaaacaac attgcgtccg tggtagagca ggctctcagt    660
accgtggtag agaaggtcac ctccgcccta tcacagctgg acactaatgg gtacgtcagt    720
gacaggtcca ctccccttga atgtaccgac cctaactcag ctatgtagat actcgatctg    780
gggaactttg cttgcctcct cattggctcc cttttttgaca gataacccgc tgcctgatgg    840
atatccatgg ggcaacttga cggactacgg caacaacccg tatcgtgaat gtccacatac    900
cggcattact agatcctatc acttcaccat cagtcgggga gtcattgctc cagatggcta    960
cgaacgcgag gtgctccttg tgaacggggc cttcccggga ccacttattg aagcaaattg   1020
gggagacacc atcattgtga agttttcaa caatatatca aaccccgaag agggcacctc    1080
catacactgg cacggcttcc tccagcacca cactccctgg gaagatggca ctcctggcat   1140
cacccaatgt cccatcccct cgggaaaagc ttacacctac aagttcaacg ccagtctgta   1200
cggtacaacc tggtatcatg cccattactc agcccaatat gctggtggca ttgttgggcc   1260
tattgttatc catggaccaa ccaaagaagg ctatgatatt gatgtcggtc ctgtcatgct   1320
gggtggtaag ctctatccga ccgggagatg actggcaact agatgtcacg aagactcata   1380
acttccacag attggtatca ccaagaatac tacaatatcg tcaagacaat gctgagcccc   1440
agcgaaagtc ctctccgggt ttattccgac aacaacctga tcaacggcaa gatggacttc   1500
aactgttcga ccgtctctga agacgacccg caccgatgca caccaaacgc ggggatatcc   1560
aaattccgct tccaggccgg tcaggttcat cgcttgcgcc tcatcaacct aggcggcgac   1620
ggtatccagc gcttctccat agatgagcac gtcctaaccg tcatcgccga ggactttgtg   1680
ccggtcaagc cgtacaacac gacagtggta gtgctgggcg tcggccagcg cgctgatgtt   1740
ttggtgactg ccaatgcggg agggcccaag tctacgttct ggatgcgctc cagcctcacg   1800
acatgctcgc cggccaggca gccgaacgct gtggctgttg tgttgtatga tgaggcggac   1860
gagaatgcgg tgccgaatag caagccgtgg gagataccga atcctgatgt gtgtgctaat   1920
ctgccgctgg agatcaccga gccactgtac ccaattccgc tgcctgagcc gacctttaca   1980
gagagaatgg agatcgagat cttcaaaaat gagtccaaga tttggctgtg aagttcaat    2040 gatatatcaa tgcggacgca ttacaacaag ccggtgctgc tgctcgccaa ccaaggagaa   2100
tatgactacc ccgaagaatg gaacgtcgtg aactactatc aaaacgagtc cgtccgaatt   2160
gttgtgaaaa acaactctcc taccccgtag gtatacctca gaggaatctt ctgctcttgt   2220
tgtccgcata ccatgactaa cccctgactc aacagccacc cgatgcatct ccacggccac   2280 aactttttaca tcctccacga gggccccggc gactgggatg caccatggt ccggccaagc    2340 aacccccaca gacgggacgt ctacctggta cgcgggtttg gtcatcttgt tctgcaattc   2400
gatggtgaac ctggtacgtg tgccgtagtt ctcagccaga ctccgtgtgc gcttggagga   2460
aggcaatcta acaacataat aggagtctgg gccttccact gccatattgc atggcacgca   2520
tcgggtggtt ttctagcgac gcttattgtc cagcccgata cggttgagaa attcaacgtt   2580
ccggaggatg tgtggaataa ctgcaacgcg tgggatcact acacaaagca taacgttgtt   2640
gagcagattg acagtggtac ataattttta ggttcgtttc gttggccgag tcggcagct   2700 gataggacac ggtttaaatt ccccgtcgga ataatgtcga tgtagttttt gcatatatac   2760
```

```
tcatcgttga tggagactca cagtcaacac tcgaaattgg atcgtaatac atggcagttt    2820
gtgcacagcc aaattgcacg aaaatgtgct tattgagcga ccgtgggcat tatatcattc    2880
aagaagcaaa caactgtaca tcgcacgtac gtactgtcaa ggagtcgata catgcatcat    2940
aaaccgaata tcaggccaag gtattcaagc aaaaatgata gacagtccgt gagtctgagt    3000
ccagtccaaa cccgagtcca agctt                                          3025
```

```
<210> SEQ ID NO 51
<211> LENGTH: 623
<212> TYPE: PRT
<213> ORGANISM: Chaetomium thermophilum ALKO4265
<220> FEATURE:
<221> NAME/KEY: MISC_FEATURE
<222> LOCATION: (1)..(623)
<223> OTHER INFORMATION: Deduced amino acid sequence of  Chaetomium
      thermophilum ALKO4265 CtLcc3

<400> SEQUENCE: 51

Met Gly Val Ile Leu Glu Asp Leu Asn Asn Ile Ala Ser Val Val Glu
1               5                   10                  15

Gln Ala Leu Ser Thr Val Val Glu Lys Val Thr Ser Ala Leu Ser Gln
            20                  25                  30

Leu Asp Thr Asn Gly Tyr Ser Ile Trp Gly Thr Leu Leu Ala Ser Ser
        35                  40                  45

Leu Ala Pro Phe Leu Thr Asp Asn Pro Leu Pro Asp Gly Tyr Pro Trp
    50                  55                  60

Gly Asn Leu Thr Asp Tyr Gly Asn Asn Pro Tyr Arg Glu Cys Pro His
65                  70                  75                  80

Thr Gly Ile Thr Arg Ser Tyr His Phe Thr Ile Ser Arg Gly Val Ile
                85                  90                  95

Ala Pro Asp Gly Tyr Glu Arg Glu Val Leu Leu Val Asn Gly Ala Phe
            100                 105                 110

Pro Gly Pro Leu Ile Glu Ala Asn Trp Gly Asp Thr Ile Ile Val Lys
        115                 120                 125

Val Phe Asn Asn Ile Ser Asn Pro Glu Glu Gly Thr Ser Ile His Trp
    130                 135                 140

His Gly Phe Leu Gln His His Thr Pro Trp Glu Asp Gly Thr Pro Gly
145                 150                 155                 160

Ile Thr Gln Cys Pro Ile Pro Ser Gly Lys Ala Tyr Thr Tyr Lys Phe
                165                 170                 175

Asn Ala Ser Leu Tyr Gly Thr Thr Trp Tyr His Ala His Tyr Ser Ala
            180                 185                 190

Gln Tyr Ala Gly Gly Ile Val Gly Pro Ile Val Ile His Gly Pro Thr
        195                 200                 205

Lys Glu Gly Tyr Asp Ile Asp Val Gly Pro Val Met Leu Gly Asp Trp
    210                 215                 220

Tyr His Gln Glu Tyr Tyr Asn Ile Val Lys Thr Met Leu Ser Pro Ser
225                 230                 235                 240

Glu Ser Pro Leu Arg Val Tyr Ser Asp Asn Asn Leu Ile Asn Gly Lys
                245                 250                 255

Met Asp Phe Asn Cys Ser Thr Val Ser Glu Asp Pro His Arg Cys
            260                 265                 270

Thr Pro Asn Ala Gly Ile Ser Lys Phe Arg Phe Gln Ala Gly Gln Val
        275                 280                 285

His Arg Leu Arg Leu Ile Asn Leu Gly Gly Asp Gly Ile Gln Arg Phe
    290                 295                 300
```

```
Ser Ile Asp Glu His Val Leu Thr Val Ile Ala Glu Asp Phe Val Pro
305                 310                 315                 320

Val Lys Pro Tyr Asn Thr Thr Val Val Leu Gly Val Gly Gln Arg
            325                 330                 335

Ala Asp Val Leu Val Thr Ala Asn Ala Gly Gly Pro Lys Ser Thr Phe
            340                 345                 350

Trp Met Arg Ser Ser Leu Thr Thr Cys Ser Pro Ala Arg Gln Pro Asn
            355                 360                 365

Ala Val Ala Val Val Leu Tyr Asp Glu Ala Asp Glu Asn Ala Val Pro
            370                 375                 380

Asn Ser Lys Pro Trp Glu Ile Pro Asn Pro Asp Val Cys Ala Asn Leu
385                 390                 395                 400

Pro Leu Glu Ile Thr Glu Pro Leu Tyr Pro Ile Pro Leu Pro Glu Pro
            405                 410                 415

Thr Phe Thr Glu Arg Met Glu Ile Glu Ile Phe Lys Asn Glu Ser Lys
            420                 425                 430

Ile Trp Leu Trp Lys Phe Asn Asp Ile Ser Met Arg Thr His Tyr Asn
            435                 440                 445

Lys Pro Val Leu Leu Leu Ala Asn Gln Gly Glu Tyr Asp Tyr Pro Glu
    450                 455                 460

Glu Trp Asn Val Val Asn Tyr Tyr Gln Asn Glu Ser Val Arg Ile Val
465                 470                 475                 480

Val Lys Asn Asn Ser Pro Thr Pro His Pro Met His Leu His Gly His
            485                 490                 495

Asn Phe Tyr Ile Leu His Glu Gly Pro Gly Asp Trp Asp Gly Thr Met
            500                 505                 510

Val Arg Pro Ser Asn Pro His Arg Arg Asp Val Tyr Leu Val Arg Gly
            515                 520                 525

Phe Gly His Leu Val Leu Gln Phe Asp Gly Glu Pro Gly Thr Cys Ala
            530                 535                 540

Val Val Leu Ser Gln Thr Pro Cys Ala Leu Gly Gly Arg Gln Ser Asn
545                 550                 555                 560

Asn Ile Ile Gly Val Trp Ala Phe His Cys His Ile Ala Trp His Ala
            565                 570                 575

Ser Gly Gly Phe Leu Ala Thr Leu Ile Val Gln Pro Asp Thr Val Glu
            580                 585                 590

Lys Phe Asn Val Pro Glu Asp Val Trp Asn Asn Cys Asn Ala Trp Asp
            595                 600                 605

His Tyr Thr Lys His Asn Val Val Glu Gln Ile Asp Ser Gly Thr
610                 615                 620
```

LACCASE ENZYMES AND THEIR USES

FIELD OF THE INVENTION

This invention relates to novel laccase enzymes useful in many applications. This invention relates also to nucleic acids encoding the enzymes, vectors, host cells and methods for producing the enzymes as well as enzyme preparations comprising the enzymes. Furthermore, this invention relates to methods for treating denim, methods for stain removal, methods for treating natural or man-made fibre or lignocellulosic fibre, methods for treating wool, methods for treating hair and methods for bleaching pulp and dye house effluents and methods for decolorizing dyes. This invention relates also to various uses and compositions, which can be used in the mentioned applications.

BACKGROUND OF THE INVENTION

Laccases (EC. 1.10.3.2 p-benzenediol:oxygen oxidoreductase) belong to a family of multi-copper oxidases. Laccases are widely distributed enzymes in higher plants, fungi, some insects and bacteria. They are characterized by low substrate specificity, oxidizing various substrate, including diphenols, polyphenols, different substituted phenols, diamines, aromatic amines, and even inorganic compounds like iodine. Laccases oxidize their substrates by a one-electron oxidation mechanism, and they use molecular oxygen as an electron acceptor. Among laccases the primary sequence, induction mechanism, physico-chemical (e.g. isoelectric point and carbohydrate content) and biochemical characteristics are variable. The copper binding sites of laccases are, however, strictly conserved.

Several laccase proteins and genes encoding these laccases have been previously isolated. For example WO 01/92498 describes a fungal laccase enzyme isolated from *Melanocarpus albomyces* strain, the patent publication EP 0765394 B1 (corresponding U.S. Pat. No. 5,981,243) describes the cloning of a laccase gene from *Myceliophthora thermophila* and its expression in *Aspergillus* and U.S. Pat. No. 5,750,388 describes the cloning of a laccase gene from *Scytalidium thermophilum* and its expression in *Aspergillus*.

Chefetz et al. (1998a) describe isolation and preliminary characterization of a laccase from composted municipal soil waste. The microbe producing this laccase was later identified as *Chaetomium thermophilum*, and the enzyme was further purified and characterized (Chefetz et al., 1998b). The reported enzyme had pI 5.1. The laccase was stable for 1 h at 70° C. and had half-lives of 24 and 12 h at 40 and 50° C., respectively. The enzyme was stable at pH 5 to 10 and the pH optimum was 6. Saito et al. (2003) describe purification and characterization of an extracellular laccase of a fungus from family Chaetomiaceae. The molecular mass of the enzyme was approximately 73 to 80 kDa and pI of 3.5. The optimum pH for the oxidation of syringaldazine was 7.0 and the optimum temperature was 42° C. The laccase was stable for up to 288 h at 4° C. and its respective half-life times at 25 and 40° C. were estimated to be 150 and 20 h.

Laccases have many industrially potential applications, such as delignification of wood pulps, methods for treating lignin containing fibers, methods for treating wood fibers in order to functionalize them or glue the fibers, improval of the production of fuel ethanol from renewable raw materials, food applications (for example in baking or clarification of beer or wine), various bioremediative processes and textile applications, such as denim treatment, stain removal, treatment of various fibers for textile industry, methods for decolorizing dyes and methods for treating dye house effluents, or use in hair dyeing composition, in hard-surface cleaning or in detergent formulations.

"Stone washed" look or an abraded look has been denim producers' interest in recent years. Traditional stone washing with pumice stones reduces the strength of fabric and burdens the laundering apparatuses. Past years the trend has been towards enzymatic denim finishing processes. "Bleached look" of denim is normally obtained by means of bleaching chemicals, e.g. sodium hypochlorite. So far bleaching with hypochlorite has been the most efficient bleaching method for denim dyed with Indigo, since almost all shades can be obtained. However, hypochlorite process is environmentally very harmful, it is difficult to control and it damages the fabric easily. It is also very inconvenient or even harmful method for the user, it cannot be used for Lycra containing products and antichlor treatment with several rinsing/washing steps is required. There is thus a need for development of ecologically less harmful alternative for sodium hypochlorite, in particular laccases have been studied for that purpose.

WO 97/25468 describes the use of laccase in a method for providing to dyed denim an abraded look. The method comprises a cellulase treatment and simultaneous or subsequent treatment with a phenol oxidizing enzyme, such as laccase, and an enhancing agent, such as methylsyringate. *Myceliophthora thermophila* laccase is the example of laccases in the patent publication.

In textile industry new materials, finishes and dyes have been developed in recent years. Although the new developments have many advantageous properties, such as easy drying, stain and water resistance, or bright colours of the textiles, their disadvantage quite often is that they must be washed at low temperatures. Low temperatures are preferred also for economical reasons, since the use of low temperatures saves energy. There is thus a need for laccases which function at low temperatures.

Even though numerous publications describing laccases from various microorganisms are available, there is still a need for novel laccases, which would function more effectively and be more suitable for the various conditions in different applications.

SUMMARY OF THE INVENTION

It is an aim of the present invention to eliminate at least some of the problems associated with the prior art. In particular, it is an aim of this invention to provide novel laccase enzymes having varying properties suitable for different applications.

This invention is based on the surprising finding that laccase enzymes having novel and diverse properties can be isolated from the same genus, species and even from the same strain. Some of the laccases are in particular suitable for use at relatively low temperatures.

One object of this invention is a laccase enzyme, which comprises the amino acid sequence SEQ ID 41 (TaLcc2) or a sequence showing at least 60% identity to the sequence SEQ ID NO: 41.

More specifically the laccase enzyme of this invention is characterized by what is stated in the characterizing part of claim 1.

The enzyme is preferably obtainable from a microorganism, more preferably from a filamentous fungus, in particular from the genus *Thielavia*, more specifically from the species *Thielavia arenaria*. Advantageously, the enzyme is obtainable from the strain CBS 116071 deposited on 2 Sep. 2004 at Centraalbureau voor Schimmelcultures, Upsalalaan 8, 3584 CT, Utrecht, the Netherlands.

The enzyme functions at broad pH range from pH 3 to 9, preferably at pH 4 to 8, most preferably at pH 4.5 to 6.5. The enzyme functions also at broad temperature range. For example, in denim treatment the enzyme is effective at 30 to 80 ° C., preferably at temperatures 40 to 60° C. The enzyme is most active at temperatures 40 to 50° C. and is thus very useful in applications, where lower temperatures are more advantageous.

In particular, in denim treatment laccases that can be used at low temperatures have advantages over laccases which function better in conventional temperatures, such as about 60° C. Lower temperatures save energy and are more economical.

The laccase enzymes of the present invention are suitable also for other applications, where low temperatures are more advantageous. Such applications are for example other textile applications, such as stain removal, or for example hair dyeing.

One object of this invention is also a laccase enzyme, which comprises the amino acid sequence SEQ ID 43 (TaLcc3) or a sequence showing at least 58% identity to the sequence SEQ ID NO: 43.

The enzyme is preferably obtainable from a microorganism, more preferably from a filamentous fungus, in particular from the genus *Thielavia*, more specifically from the species *Thielavia arenaria*. Advantageously, the enzyme is obtainable from the strain CBS 116071 deposited on 2 Sep. 2004 at Centraalbureau voor Schimmelcultures, Upsalalaan 8, 3584 CT, Utrecht, the Netherlands.

The enzyme functions at pH 3.5 to 7.5, preferably at pH 4 to 6.5.

One object of this invention is also a laccase enzyme, which comprises the amino acid sequence SEQ ID NO: 45 (TaLcc4) or a sequence showing at least 78% identity to the sequence SEQ ID NO: 45.

The enzyme is preferably obtainable from a microorganism, more preferably from a filamentous fungus, in particular from the genus *Thielavia*, more specifically from the species *Thielavia arenaria*. Advantageously, the enzyme is obtainable from the strain CBS 116071 deposited on 2 Sep. 2004 at Centraalbureau voor Schimmelcultures, Upsalalaan 8, 3584 CT, Utrecht, the Netherlands.

The enzyme functions at pH 3.5 to 7.5, more preferably at pH 4 to 7, most preferably at pH 5 to 6.5.

One object of this invention is also a laccase enzyme, which comprises the amino acid sequence SEQ ID NO: 47 (CtLcc1) or a sequence showing at least 74% identity to the sequence SEQ ID NO: 47.

The enzyme is preferably obtainable from a microorganism, more preferably from a filamentous fungus, in particular from the genus *Chaetomium*, preferably from the species *Chaetomium thermophilum*. Advantageously, the enzyme is obtainable from the strain CBS 730.95 deposited on Nov. 8, 1995 at the Centralbureau Voor Schimmelcultures at Oosterstraat 1, 3742 SK Baarn, The Netherlands.

The enzyme functions at pH 3.5 to 8, preferably at pH 4 to 7, most preferably at pH 4.5 to 6. For example, in denim treatment the enzyme is effective at temperatures 30 to 80° C., preferably at 40 to 70° C., most preferably at 50 to 60° C.

One object of this invention is a laccase enzyme, which comprises the amino acid sequence SEQ ID 49 (CtLcc2) or a sequence showing at least 55% identity to the sequence SEQ ID NO: 49.

The enzyme is preferably obtainable from a microorganism, more preferably from a filamentous fungus, in particular from the genus *Chaetomium* preferably from the species *Chaetomium thermophilum*. Advantageously, the enzyme is obtainable from the strain CBS 730.95 deposited on Nov. 8, 1995 at the Centralbureau Voor Schimmelcultures at Oosterstraat 1, 3742 SK BAARN, The Netherlands.

One object of this invention a laccase enzyme, which comprises the amino acid sequence SEQ ID 51 (CtLcc3) or a sequence showing at least 53% identity to the sequence SEQ ID NO: 51.

The enzyme is preferably obtainable from a microorganism, more preferably from a filamentous fungus, in particular from the genus *Chaetomium* preferably from the species *Chaetomium thermophilum*. Advantageously, the enzyme is obtainable from the strain CBS 730.95 deposited on Nov. 8, 1995 at the Centralbureau Voor Schimmelcultures at Oosterstraat 1, 3742 SK Baarn, The Netherlands.

The present invention relates in particular to laccase enzymes, which show at least 60% identity to the amino acid sequence SEQ ID NO:41 (TaLcc2), laccase enzymes, which show at least 58% identity to the amino acid sequence SEQ ID NO:43 (TaLcc3), laccase enzymes, which show at least 78% identity to the amino acid sequence SEQ ID NO:45 (TaLcc4) and laccase enzymes, which show at least 74% identity to the amino acid sequence SEQ ID NO:47 (CtLcc1) and which are most effective at temperature 40 to 60° C.

One object of this invention is also a nucleic acid sequence, which encodes at least one of the enzymes of the invention.

Further objects of this invention are a vector comprising the nucleic acid sequence and a host comprising the nucleic acid sequence or the vector, and a process for the production of a polypeptide having laccase activity.

One further object of the invention is a process for obtaining an enzyme preparation comprising the polypeptide or enzyme, which comprises the steps of culturing a host cell comprising the nucleic acid sequence encoding the enzyme or a vector comprising the nucleic acid sequence and either recovering the polypeptide from the cells or separating the cells from the culture medium and obtaining the supernatant. Furthermore, an object of the invention is the enzyme preparation comprising the laccase enzyme of the invention.

One object of this invention is a method for treating denim, which comprises contacting denim in an aqueous medium with the laccase enzyme or enzyme preparation of the invention under suitable conditions for the function of the enzyme.

One object of this invention is a method for removing stains, which comprises that material to be treated with the method is contacted with a laccase enzyme of the present invention under suitable conditions for the function of the enzyme.

This invention provides also a method of bleaching pulp, for treating natural or man-made fibers, a method for treating wool, a method for treating hair, a method for treating dye house effluents and a method for decolorizing dyes by using the laccase enzyme of the present invention.

Still further objects of this invention are uses of laccase enzyme of the present invention in various applications and compositions.

By using the laccase enzymes of this invention in denim bleaching it is possible to obtain many advantages. By using the laccase enzymes of this invention it is possible to decrease or even avoid avoid the environmentally harmful effects of sodium hypochlorite. If sodium hypochlorite not used, no antichlor treatment is required. By the laccases of the present invention it is also possible to obtain various shades as by sodium hypochlorite bleaching. One advantage of the laccase enzymes of the invention is that the treatment does not damage the fabric. The laccases can also be used for treating Lycra containing products. In addition, the laccase treatment is also convenient for the user.

Furthermore, the enzymes can function on a broad temperature and pH range. Some of the enzymes are in particular suitable for use at low temperatures, in particular at temperatures 40 to 50° C.

Other features, aspects and advantages of the present invention will become apparent from the following description and appended claims.

BRIEF DESCRIPTION OF THE DRAWINGS

FIG. 5. The peptide sequences used in the planning of the PCR primers for cloning the *Thielavia arenaria* ALKO4197 and *Chaetomium thermophilum* ALKO4265 laccase genes. All possible codons to encode the sequences are shown. A. The homologous peptide sequences chosen from alignment of several fungal laccase sequences. The first methionine in Peptides II and III (in parenthesis) was not present in all the laccase sequences. B. The tryptic peptide sequences obtained from the purified *Thielavia arenaria* ALKO4197 TaLcc1. Peptide I is according to SEQ ID NO:1, Peptide II is according to SEQ ID NO:2, and Peptide III is according to SEQ ID NO:3. C. The N-terminal sequence (SEQ ID NO:4) and the tryptic peptide sequences (SEQ ID NO:5) obtained from the purified *Chaetomium thermophilum* ALKO4265 CtLcc1.

FIG. 6 A-G. The nucleotide and the deduced amino acid sequences of the *Thielavia arenaria* ALKO4197 and *Chaetomium thermophilum* ALKO4265 laccase genes. Nucleotide sequence of TaLcc1 is according to SEQ ID NO:38, and the deduced amino acid sequence according to SEQ ID NO:39, Nucleotide sequence of TaLcc2 is according to SEQ ID NO:40 and the deduced amino acid sequence according to SEQ ID NQ:41. Nucleotide sequence of TaLcc3 is according to SEQ ID NO:42 and the deduced amino acid sequence according to SEQ ID NQ:43. Nucleotide sequence of TaLcc4 is according to SEQ ID NQ:44 and the deduced amino acid sequence is according to SEQ ID NO:45. Nucleotide sequence of CtLcc1 is according to SEQ ID NO:46 and the deduced amino acid sequence is according to SEQ ID NQ:47. Nucleotide sequence CtLcc2 is according to SEQ ID NQ:48 and the deduce amino acid sequence is according to SEQ ID NO:49. Nucleotide sequence of CtLcc3 is according to SEQ ID NO:50 and the deduced amino acid sequence is according to SEQ ID NO:51. The stop codon is shown by an asterisk below the sequence. The location of the putative introns and the consensus intron splicing signals (5' GTPuNGPy, 3' PyAG, internal NNCTPuAPy) are marked in the sequence by using lowercase letters and by bolding, respectively. The putative signal peptides, analyzed by SignalP V2.0 program, and the mature C-terminal amino acid sequences, determined from the purified recombinant TaLcc1 and TaLcc2 proteins, are underlined. A double underlining is used for the other potential signal sequence encoded by the longer Talcc2 gene. The location of the N-terminal peptide from CtLcc1 and the tryptic peptide sequences obtained from purified TaLcc1 and CtLcc1 are marked by dotted lines below the sequences. The conserved residues involved in copper binding are highlighted. The sites for putative N-glycosylation (N-X-S/T) in are bolded. The two putative translation start sites of TaLcc2 and CtLcc3 are boxed. A. Talcc1, B. Talcc2, C. Talcc3, D. Talcc4, E. Ctlcc1, F. Ctlcc2, G. Ctlcc3.

FIG. 7A-C. The expression cassettes used in the transformation of *Trichoderma reesei* protoplasts for producing the recombinant fungal laccases. The laccase genes were under the control of the cbh1 (cel7A) promoter (p cbh1) and the termination of the transcription was ensured by using the cbh1 terminator sequence (t cbh1). The amdS gene was included as a transformation marker and the cbh1 3'-flanking region, together with the cbh1 promoter, was used to enable targeting of the expression cassette into the cbh1 locus by homologous recombination.

SEQUENCES

Figure 1A:
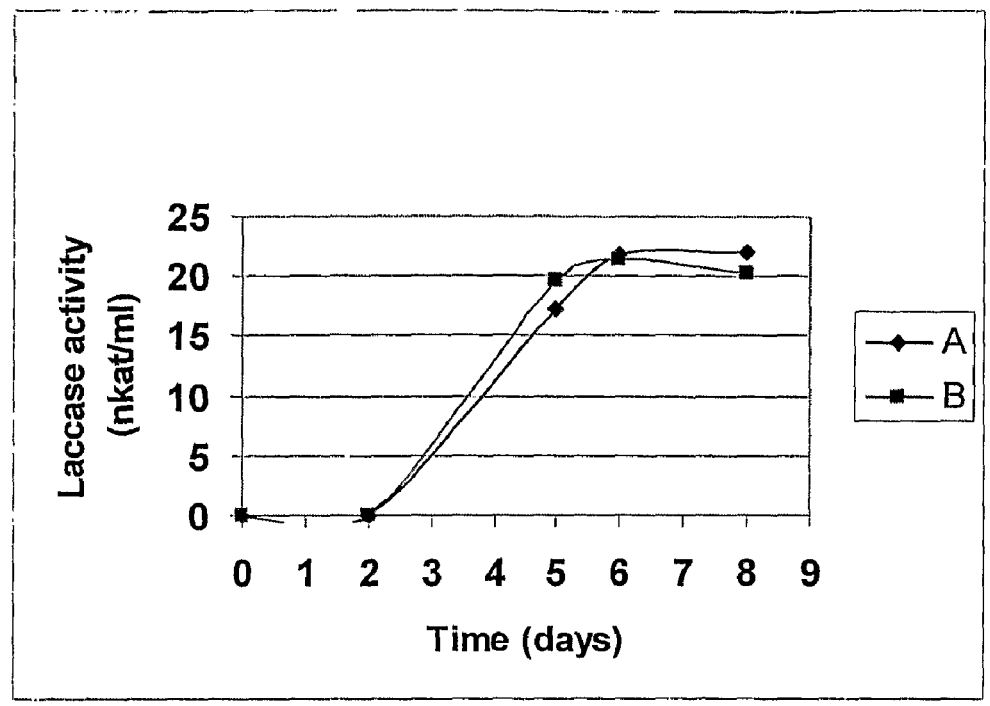
FIG. 1A. Production of the *Thielavia* laccase in 50 ml shake flask cultivation.

SEQ ID NO: 1 Sequence of Peptide 1, a tryptic peptide from *Thielavia arenaria* ALKO 4197 TaLcc1 protein.

SEQ ID NO: 2 Sequence of Peptide 2, a tryptic peptide from *Thielavia arenaria* ALKO 4197 TaLcc1 protein.

SEQ ID NO: 3 Sequence of Peptide 3, a tryptic peptide from *Thielavia arenaria* ALKO 4197 TaLcc1 protein.

SEQ ID NO: 4 N-terminal sequence from *Chaetomium thermophilum* ALKO 4265 CtLcc1 protein.

SEQ ID NO: 5 Sequence of Peptide 18.9, a tryptic peptide from *Chaetomium thermophilum* ALKO 4265 CtLcc1 protein.

SEQ ID NO: 6 Sequence of Peptide 22.4, a tryptic peptide from *Chaetomium thermophilum* ALKO 4265 CtLcc1 protein.

SEQ ID NO: 7 Sequence of Peptide 22.7, a tryptic peptide from *Chaetomium thermophilum* ALKO 4265 CtLcc1 protein.

SEQ ID NO: 8 Sequence of the oligonucleotide primer POX1

SEQ ID NO 9: Sequence of the oligonucleotide primer POX2

SEQ ID NO 10: Sequence of the oligonucleotide primer POX22

SEQ ID NO 11: Sequence of the oligonucleotide primer POX3

SEQ ID NO 12: Sequence of the oligonucleotide primer POX16

SEQ ID NO 13: Sequence of the oligonucleotide primer POX23

SEQ ID NO: 14 Sequence of the oligonucleotide primer POX26.

SEQ ID NO: 15 Sequence of the oligonucleotide primer POX27.

SEQ ID NO: 16 Sequence of the oligonucleotide primer POX28.

SEQ ID NO: 17 Sequence of the oligonucleotide primer POX29.

SEQ ID NO: 18 Sequence of the oligonucleotide primer POX30.

SEQ ID NO: 19 Sequence of the oligonucleotide primer POX31.

SEQ ID NO: 20 Sequence of the oligonucleotide primer POX4

SEQ ID NO: 21 Sequence of the oligonucleotide primer POX5

SEQ ID NO: 22 Sequence of the oligonucleotide primer POX6

SEQ ID NO: 23 Sequence of the oligonucleotide primer POX7

SEQ ID NO: 24 Sequence of the oligonucleotide primer POX8

SEQ ID NO: 25 Sequence of the oligonucleotide primer POX9

SEQ ID NO: 26 Sequence of the oligonucleotide primer POX10

SEQ ID NO: 27 Sequence of the oligonucleotide primer POX11

SEQ ID NO: 28 Sequence of the oligonucleotide primer POX12

SEQ ID NO: 29 Sequence of the oligonucleotide primer POX13

SEQ ID NO: 30 Sequence of the oligonucleotide primer POX14

SEQ ID NO: 31 Sequence of the oligonucleotide primer POX15

SEQ ID NO: 32 Sequence of the PCR fragment obtained from *Thielavia arenaria* ALKO 4197 using the primers POX27 and POX31.

SEQ ID NO: 33
Sequence of the PCR fragment obtained from *Thielavia arenaria* ALKO 4197 using the primers POX4 and POX11.

SEQ ID NO: 34
Sequence of the PCR fragment obtained from *Thielavia arenaria* ALKO 4197 using the primers POX27 and POX9.

SEQ ID NO: 35
Sequence of a PCR fragment obtained from *Chaetomium thermophilum* ALKO 4265 using the primers POX8 and POX11.

SEQ ID NO: 36
Sequence of the PCR fragment obtained from *Chaetomium thermophilum* ALKO 4265 using the primers POX4 and POX9.

SEQ ID NO: 37
Sequence of a PCR fragment obtained from *Chaetomium thermophilum* ALKO 4265 using the primers POX8 and POX11.

SEQ ID NO:38
The nucleotide sequence of the *Thielavia arenaria* ALKO 4197 Talcc1 gene.

SEQ ID NO: 39
The deduced amino acid sequence of the *Thielavia arenaria* ALKO 4197 TaLcc1.

SEQ ID NO: 40
The nucleotide sequence of the *Thielavia arenaria* ALKO 4197 Talcc2 gene.

SEQ ID NO: 41
The deduced amino acid sequence of the *Thielavia arenaria* ALKO 4197 TaLcc2.

SEQ ID NO: 42
The nucleotide sequence of the *Thielavia arenaria* ALKO 4197 Talcc3 gene.

SEQ ID NO: 43
The deduced amino acid sequence of the *Thielavia arenaria* ALKO 4197 TaLcc3.

SEQ ID NO: 44
The nucleotide sequence of the *Thielavia arenaria* ALKO 4197 Talcc4 gene.

SEQ ID NO: 45
The deduced amino acid sequence of the *Thielavia arenaria* ALKO 4197 TaLcc4.

SEQ ID NO: 46
The nucleotide sequence of the *Chaetomium thermophilum* ALKO 4265 Ctlcc1 gene.

SEQ ID NO: 47
The deduced amino acid sequence of the *Chaetomium thermophilum* ALKO 4265 CtLcc1.

SEQ ID NO: 48
The nucleotide sequence of the *Chaetomium thermophilum* ALKO 4265 Ctlcc2 gene.

SEQ ID NO: 49
The deduced amino acid sequence of the *Chaetomium thermophilum* ALKO 4265 CtLcc2.

SEQ ID NO: 50
The nucleotide sequence of the *Chaetomium thermophilum ALKO* 4265 Ctlcc3 gene.

SEQ ID NO: 51
The deduced amino acid sequence of the *Chaetomium thermophilum* ALKO 4265 CtLcc3.

DEPOSITIONS

*Thielavia arenaria* ALKO 4197 was deposited at the Centralbureau Voor Schimmelcultures at Upsalalaan 8, 3584 CT, Utrecht, the Netherlands on 2 Sep. 2004 and assigned accession number CBS 116071.

*Chaetomium thermophilum* ALKO 4265 was deposited at the Centralbureau Voor Schimmelcultures at Oosterstraat 1, 3742 SK BAARN, The Netherlands on Nov. 8, 1995 and assigned accession number CBS 730.95. After termination of the current deposit period, samples will be stored under agreements as to make the strain available beyond the enforceable time of the patent.

The *E.coli* strain including the plasmid pALK1342 was deposited at the Deutsche Sammlung von Mikroorganismen und Zellkulturen GmbH (DSMZ), Mascheroder Weg 1 b, D-38124 Braunschweig, Germany on 7 Mar. 2003 and assigned accession number DSM 15484.

The *E.coli* strain including the plasmid pALK1347 was deposited at the Deutsche Sammlung von Mikroorganismen und Zellkulturen GmbH (DSMZ), Mascheroder Weg 1 b, D-38124 Braunschweig, Germany on 7 Mar. 2003 and assigned accession number DSM 15486.

The *E.coli* strain including the plasmid pALK1345 was deposited at the Deutsche Sammlung von Mikroorganismen und Zellkulturen GmbH (DSMZ), Mascheroder Weg 1 b, D-38124 Braunschweig, Germany on 7 Mar. 2003 and assigned accession number DSM 15485.

The *E.coli* strain including the plasmid pALK1664 was deposited at the Deutsche Sammlung von Mikroorganismen und Zellkulturen GmbH (DSMZ), Mascheroder Weg 1 b, D-38124 Braunschweig, Germany on 7 Mar. 2003 and assigned accession number DSM 15487.

The *E.coli* strain including the plasmid pALK1304 was deposited at the Deutsche Sammlung von Mikroorganismen und Zellkulturen GmbH (DSMZ), Mascheroder Weg 1 b, D-38124 Braunschweig, Germany on 27 Jun. 2002 and assigned accession number DSM 15075.

The *E.coli* strain including the plasmid pALK1305 was deposited at the Deutsche Sammlung von Mikroorganismen und Zellkulturen GmbH (DSMZ), Mascheroder Weg 1 b, D-38124 Braunschweig, Germany on 27 Jun. 2002 and assigned accession number DSM 15076.

The *E.coli* strain including the plasmid pALK1685 was deposited at the Deutsche Sammlung von Mikroorganismen und Zellkulturen GmbH (DSMZ), Mascheroder Weg 1 b, D-38124 Braunschweig, Germany on 20 Nov. 2003 and assigned accession number DSM 16040.

DETAILED DESCRIPTION

The present invention provides several laccase enzymes, which have diverse properties and which are suitable for different applications.

By "the laccase of the present invention" or "the laccases of the present invention" is here meant the group of laccases as defined in the claims and described herein.

By "laccase enzyme" is in connection of this invention meant an enzyme classified as EC 1.10.3.2 by the enzyme nomenclature. The laccase enzyme may originate from any organism including plants, preferably it may originate from microorganisms. It may originate from bacteria, for example from a genus selected from the group comprising *Bacillus*, *Azospirillum* and *Streptomyces*. Preferably the enzyme originates from fungi (including filamentous fungi and yeasts), for example from a genus selected from the group comprising *Thielavia*, *Chaetomium*, *Achaetomium*, *Aspergillus*, *Botrytis*, *Collybia*, *Fomes*, *Humicola*, *Hypocrea*, *Lentinus*, *Melanocarpus*, *Myceliophthora*, *Neurospora*, *Phlebia*, *Pleurotus*, *Podospora*, *Polyporus*, *Rhizoctonia*, *Scytalidum*, *Pycnoporus*, *Trametes* and *Trichoderma*.

According to a preferred embodiment of the invention the laccases of the present invention are obtainable from genus *Thielavia*, more preferably from *Thielavia arenaria*. According to a most preferred embodiment of the invention the enzyme is obtainable from a strain deposited at Centraalbureau voor Schimmelcultures under number CBS 116071.

According to another preferred embodiment of the invention the laccases of the present invention are obtainable from genus *Chaetomium*, more preferably from *Chaetomium thermophilum*. According to a most preferred embodiment of the invention the enzyme is obtainable from a strain deposited at Centraalbureau voor Schimmelcultures under number CBS 730.95.

The origin of the laccases of the present invention is not restricted to genus *Thielavia* or to the species *T. arenaria* or to *Chaetomium* or to species *C. thermophilum*. By using the description provided herein, a person skilled in the art can find and isolate laccases of the present invention from other genera of fungi, from other microorganisms and also from higher organisms, such as plants.

Laccase of the present invention can be isolated from any organism producing laccase. Preferably the laccase enzyme of the present invention is isolated from a microbial source. Organisms capable of producing laccase can be screened, the activity on various substrates can be determined, and the enzyme characterized. For example, the pH and temperature ranges, where the enzyme functions, pH and temperature optima, and enzyme stability in various temperatures, can be determined. Alternatively, genes encoding laccases in various organisms can be isolated and the amino acid sequences encoded by the genes can be compared with the amino acid sequence of the laccases isolated and characterized in the Examples here. This includes direct cloning from environmental samples.

Microorganisms that produce the laccase of the present invention can be isolated from nature or they can be screened from already isolated and identified strains of culture collections by using screening methods that are well known to a person skilled in the art. Screening can be carried out by studying the production of the enzyme either on a solid culture on plate cultivations or in a liquid culture medium by measuring the enzyme activity. Suitable substrates for measuring the activity include ABTS, dimethoxyphenol (DMP), guaiacol, and syringaldazine. Fungi can be screened for their ability to produce laccases for example by the methods referred in Example 1 with indicators, such as Remazol Brilliant Blue R-478 and guaiacol or ABTS. Suitable laccases can be isolated and the genes encoding them can be cloned also from higher organisms, such as plants.

Microorganism strains, which are found as a result of screening can be cultivated on a suitable medium, and the formation of laccase in the culture solution or plate can be observed. After a sufficient amount of laccase of interest has been produced, the enzyme can be purified and its properties can be more thoroughly characterized.

The produced laccase enzymes can be isolated and purified by using conventional methods of protein chemistry, such as salt precipitation, ultrafiltration, ion exchange chromatography, and hydrophobic interaction chromatography. Purification can be monitored by protein determination, enzyme activity assays and by SDS polyacrylamide gel electrophoresis. The enzyme activity of the purified enzyme at various temperatures and pH values can be determined; similarly, the molecular weight and the isoelectric point can be determined.

The purified enzyme refers to an enzyme preparation, which has no other proteins or very low amount of other proteins in addition to the laccase protein. The purity of the obtained laccase that is essentially free from other proteins is $\geq 90\%$.

The purification of the preferred laccases of the present invention has been exemplified in Example 1. Concentrated *Thielavia* culture filtrate was loaded on Q Sepharose FF column, proteins were eluted with an increasing salt gradient and laccase active fractions were loaded on Sephacryl S100 gel filtration resin. Purification was followed by activity assays and by SDS-PAGE and subsequent staining with Coomassie Brilliant Blue. In order to obtain high purity samples an additional Resource Q anion exchange step was included. The culture supernatant of *Chaetomium* laccase was concentrated and buffer changed to binding buffer by ultrafiltration. Proteins were bound to DEAE Sepharose FF, eluted with a sodium sulphate gradient and laccase positive fractions were pooled and further purified with hydrophobic interaction chromatography. Finally the purity of active fractions were analysed by SDS-PAGE and subsequent Coomassie staining. Naturally, it is possible to separate the enzymes of the present invention by using other known purification methods instead, or in addition to the methods described here.

Molecular weight of the laccase can be determined on SDS-PAGE according to Laemanli (1970) and the isoelectric point of the laccase can be determined with isoelectric focusing and bands containing laccase activity can be visualized by staining the gel with ABTS, for example, as described in Example 2.

Determination of laccase activity at various temperatures can be carried out by using ABTS as a substrate, as described in Example 1 in accordance with the method developed by Niku-Paavola et al. (1988) or by other methods described in literature.

The pH optimum of the laccase can be determined on a suitable substrate in a suitable buffer at different pH values by measuring activity.

The thermal stability can be determined by incubating an enzyme sample for different time periods at various temperatures in a suitable buffer at a certain pH. The residual activity of the enzyme at each temperature can be defined pH values by measuring activity.

Specific activities of the purified laccase can be determined towards different laccase substrates, such as ABTS, di-methoxy-phenol (DMP), syringaldazine, and guaiacol.

The effect of various inhibitors on laccase activity can be determined by measuring the oxygen consumption during the enzyme reaction with ABTS, for example, in sealed and fully filled containers with oxygen electrode or following the enzyme activity by spectroscopic means in the presence of an inhibitor.

The N-terminus of the protein as well as the internal peptides can be sequenced according to Edman degradation chemistry [Edman and Begg (1967)] as described in Example 2 or by other methods described in the literature.

The molecular weight of the purified major laccase enzymes isolated from *Thielavia arenaria* and *Chaetomium thermophilum* culture supernatants were both approximately 80 kDa. The purified *Thielavia* laccase showed multiple bands in isoelectric focusing at pIs 5.5, 5.9, 6.4, 6.8, and 6.9. The purified *Chaetomium* laccase showed 3-4 bands in isolelectric focusing at pIs 4.1 to 4.3.

The pH optimum for the purified *Thielavia* laccase was 5.5 determined on guaiacol, and the enzyme showed substantially high activity still at pH 7. The pH optimum for the purified *Chaetomium* laccase was at pH 5.0. The accurary of the measurement is ±0.5.

The specific activity of the *Thielavia* laccase enzyme was the highest on ABTS, 1020 nkat/mg of protein at pH 4.5. The specific activity on DMS was 260, on syringaldazin 490 and on guaiacol 63 nkat/mg at pH 5.5. The specific activity of the *Chaetomium* laccase enzyme was the highest on ABTS, 750 nkat/mg of protein at pH 4.5. The specific activity on DMP was 290, on syringaldazin 400 and on guaiacol 85 nkat/mg at pH 5.5.

The laccase which shows advantageous properties may be either produced by the original or recombinant host by a method comprising cultivating under suitable conditions a host into which a DNA sequence encoding said laccase and sequences needed for expressing said enzyme, have been introduced, and optionally isolating the enzyme. The production host can be any organism capable of expressing the laccase. Preferably the host is a microbial cell, more preferably a fungus. Most preferably the host is a filamentous fungus. Preferably the recombinant host is modified to express and secrete laccase as its main activity or one of its main activities. The spent culture medium of the production host can be used as such, or it may be concentrated, filtrated or fractionated. It may also be dried.

Suitable expression and production host systems are for example the production system developed for the fungus host *Trichoderma* (EP 244 234), or *Aspergillus* production system, such as *A. oryzae* or *A. niger* (WO 9708325 and WO 9533386, U.S. Pat. No. 5,843,745, U.S. Pat. No. 5,770,418), or the production system developed for fungal species of *Fusarium*, such as *F. oxysporum* (Malardier et al., 1989). Suitable production systems developed for bacteria are a production system developed for *Bacillus*, for example *B. subtilis* or for *E. coli*, or for actinomycete *Streptomyces*. Suitable production systems developed for yeasts are systems developed for *Saccharomyces, Shizosaccharomyces* or *Pichia pastoris*. Production systems in some other microbes or in mammalian cell can also be used.

Preferred hosts for producing laccase enzyme of the present invention are in particular strains from genus *Trichoderma* or *Aspergillus*.

Within the scope of protection of the present invention are also vectors which can be used when the nucleic acid sequence encoding the chosen laccase are introduced into a host. Within the scope of protection are also sequences facilitating the expression and secretion of the laccase encoding sequence, such as promoters and signal sequences.

Standard molecular biology methods can be used in the cloning of the laccase enzyme i.e. in the isolation and enzyme treatments of DNA, in *E. coli* transformations, etc. The basic methods used are described in the standard molecular biology handbooks, e.g. Sambrook et al. (1989) and Sambrook and Russell (2001).

Genomic library prepared from the chosen host organism was screened with probes prepared by PCR. The sequences of the oligonucleotide primers used in the PCR reactions based on the amino acid sequences of the peptides obtained from the purified laccase enzyme produced by the natural host and on the consensus sequences of fungal laccases. The DNA products obtained were characterized by sequencing and by performing Southern blot hybridizations to the genomic *Thielavia* and *Chaetomium* DNA digested with several restriction enzymes.

Four laccase genes were isolated from *Thielavia* and three from *Chaetomium*. All these genes were included into plasmid vectors and deposited in an *E.coli* strain to the DSMZ collection. The full-length *Thielavia* laccase gene Talcc1 was included in the plasmid pALK1342 and deposited under number DSM 15484. Accordingly, *Thielavia* laccase gene Talcc2 was included in the plasmid pALK1347 and deposited under number DSM 15486, Taclc3 gene was included in the plasmid pALK1345 and deposited under number DSM 15485 and Talcc4 gene was included in the plasmid pALK1664 under number DSM 15487. *Chaetomium* laccase gene Ctlcc1 was included in the plasmid pALK1304 and deposited under number DSM 15075. Ctlcc2 was included in the plasmid pALK1305 and deposited under number DSM 15076. Ctlcc3 was included in the plasmid pALK1685 and deposited under number DSM 16040. The deduced amino acid sequences of the laccases were analyzed from the DNA sequence.

The sequences of the laccase genes and deduced laccase proteins are shown FIG. 6. The relevant information on the genes and the deduced amino acid sequences are summarized in Tables 8 and 9, respectively.

For example, the length of the Talcc2 gene was 1957 bp (or 1737 bp depending on the translation start site) including the stop codon and the gene had two introns. The deduced protein sequence consisted of 589 amino acids (for the shorter deduced amino acid sequence 579 amino acids) including a predicted signal sequence of 29/24 amino acids and no "tail" after the consensus sequence DSGI. The predicted molecular mass was 61811/62274 Da for the mature polypeptide and the predicted pI was 4.65/4.65 (signal sequence removed). The deduced amino acid sequence included 12 putative N-glycosylation sites.

The length of the Ctlcc1 gene was 2127 bp (including the stop codon) and the gene had five introns. The deduced protein sequence consisted of 607 amino acids including a predicted signal sequence of 20 amino acids and a "tail" of 13 amino acids after the consensus sequence DSGL. The predicted molecular mass was 63905Da for the mature polypeptide (signal sequence and tail not included) and the predicted pI was 6.09 (signal sequence removed). The deduced amino acid sequence included 9 putative N-glycosylation sites.

The deduced amino acid sequences of TaLcc1 and CtLcc1 were found to be the most homologous to each other, as were also the TaLcc3 and CtLcc2 (also at the gene level, e.g. in the organization of introns of the respective genes). The identity value obtained for TaLcc1 and CtLcc1 using Needleman-Wunsch global alignment (EMBLOSUM62, Gap penalty 10.0, Extend penalty 0.5; European Molecular Biology Open Software Suite program package, version 2.9.0; Rice et al., 2000) was 69.5% and that for TaLcc3 and CtLcc2 was 67.3% (Table 10). The identity values of the other laccase proteins were lower, when aligned with each other and with TaLcc1, CtLcc1, TaLcc3 and CtLcc2 as can be seen in Table 10.

By the term "identity" is here meant the identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite) program package, version 2.9.0, with the following parameters: EMBLOSUM62, Gap penalty 10.0, Extend penalty 0.5.

Within the scope of the present invention are enzymes or polypeptides which comprise amino acid sequences which have laccase activity and which show at least 60% identity to the amino acid sequence SEQ ID NO:41 (TaLcc2). Preferred enzymes comprise amino acid sequences which show at least 65%, more preferably at least 70%, even more preferably at least 75% identity. Still more preferable the amino acid sequences show at least 80%, more preferably at least 85%, more and more preferably at least 90%, most preferably at least 95% identity to the amino acid sequence SEQ ID NO:41.

Within the scope of the present invention are also enzymes or polypeptides which comprise amino acid sequences which have laccase activity and which show at least 58% identity to the amino acid sequence SEQ ID NO:43 (TaLcc3). Preferred enzymes comprise amino acid sequences which show at least 65%, more preferably at least 68%, even more preferably at least 75% identity. Still more preferably the amino acid sequences show at least 80%, more preferably at least 85%, more and more preferably at least 90%, most preferably at least 95% identity to the amino acid sequence SEQ ID NO:43.

Within the scope of the present invention are also enzymes or polypeptides which comprise amino acid sequences which have laccase activity and which show at least 78% identity to the amino acid sequence SEQ ID NO:45 (TaLcc4). Preferred enzymes comprise amino acid sequences which show at least 80%, more preferably at least 85%, even more preferably at least 90% identity. Most preferable the amino shows at least 95% identity to the amino acid sequence SEQ ID NO:45.

Within the scope of the present invention are enzymes or polypeptides which comprise amino acid sequences which have laccase activity and which show at least 74% identity to the amino acid sequence SEQ ID NO:47 (CtLcc1). Preferred enzymes comprise amino acid sequences which show at least 76%, more preferably at least 80%, even more preferably at least 85% identity. Still more preferable the amino acid sequences show at least 90%, most preferably at least 95% identity to the amino acid sequence SEQ ID NO:47.

Within the scope of the present invention are enzymes or polypeptides which comprise amino acid sequences which have laccase activity and which show at least 55% identity to the amino acid sequence SEQ ID NO:49 (CtLcc2). Preferred enzymes comprise amino acid sequences which show at least 60%, more preferably at least 68% identity. Still more preferable the amino acid sequences show at least 75%, more preferably at least 80%, still more preferably at least 85%, more and more preferably at least 90%, most preferably at least 95% identity to the amino acid sequence SEQ ID NO:49.

Within the scope of the present invention are enzymes or polypeptides which comprise amino acid sequences which have laccase activity and which show at least 53% identity to the amino acid sequence SEQ ID NO:51 (CtLcc3). Preferred enzymes comprise amino acid sequences which show at least 60%, more preferably at least 65%, even more preferably at least 70% identity. Still more preferable the amino acid sequences show at least 75%, more preferably at least 80%, Still more preferable the amino acid sequences show at least 85%, more and more preferably at least 90%, most preferably at least 95% identity to the amino acid sequence SEQ ID NO:51.

Within the scope of the present invention are also enzymes and truncated polypeptides as defined above, but which lack signal sequence or tail or both. The signal sequence or the tail or both may be cut for example during posttranslational phases of the production or in the spent culture medium or during the storage of the culture medium or enzyme preparation. In addition, a propeptide from the protein may be cleaved by the host. The truncation can also be achieved e.g. by shortening the gene encoding the polypeptide prior to transforming it to the production host.

The laccase according to the invention can be produced to the culture medium of its natural host or a recombinant host, from where it can be isolated and purified by using known methods of protein chemistry. If the culture medium contains a sufficiently high amount of laccase but no other detrimental proteins, it is possible to use the culture medium as such by simply separating the cells. When so desired, the culture solution can be concentrated, filtrated, fractionated and/or purified. It may also be dried. It is preferable to use, in various applications, an enzyme preparation containing an increased amount of laccase. Such an enzyme preparation can be prepared by producing the increased amount of laccase enzyme in the culture medium of the production host by means of gene technology or by optimising the culture conditions. The increased amount refers to an amount of laccase enzyme, which exceeds the amount of laccase enzyme naturally produced by the natural host. By "spent culture medium" is here meant the culture medium of the host comprising the produced enzymes.

According to a preferred embodiment of the invention *Thielavia* and *Chaetomium* laccases can be produced in a filamentous fungus host, preferably in a *Trichoderma* host. The production is described in more detail in Example 4. The purification and characterization of recombinant laccases in terms of pH optimum, thermal stability, and pI is described in Example 5. *Thielavia* laccase TaLcc2 had pH optimum on guaiacol at pH 5.5, TaLcc3 at pH 5.0 on guaiacol, TaLcc4 at pH 6.0 on DMP. CtLcc 1 had pH optimum on guaiacol at pH 5.0.

TaLcc2 enzyme functions at a broad pH range from pH 3 to 9, preferably at pH 4 to 8, most preferably at pH 4.5 to 6.5 determined on guaiacol. TaLcc3 enzyme functions at pH 3.5 to 7.5, preferably at pH 4 to 6.5 determined on guaiacol. TaLcc4 enzyme functions at pH 3.5 to 7.5, more preferably at pH 4 to 7, most preferably at pH 5 to 6.5 determined on DMP.

CtLcc1 enzyme functions at pH 3.5 to 8, preferably at pH 4 to 7, most preferably at pH 4.5 to 6 determiner guaiacol.

Of the mentioned pH ranges the first pH range means that 20% or more of the maximal activity is on this region, the second pH range means that 40% or more of the activity is on this region. The third region means that 80% or more of the activity is on this region.

The specific activities were determined towards ABTS, DMP, syringaldazine and guaiacol as described in Example 6. The specific activity of TaLcc2 was highest on ABTS, 360 nkat/mg at pH 4.5, of TaLcc3 8.3 nkat/mg at pH 4.5, of TaLcc4 1000 nkat/mg at pH 4.5, respectively. The specific activity of CtLcc1 was 705 nkat/mg at pH 4.5.

Within the scope of the present invention are also laccase enzymes, which show at least 60% identity to the amino acid sequence SEQ ID NO:41 (TaLcc2) and have a specific activity of at least 300, preferably at least 350 nkat/mg towards ABTS at pH 4.5, laccase enzymes, which show at least 58% identity to the amino acid sequence SEQ ID NO:43 (TaLcc3) and have a specific activity of at least 7, preferably at least 8 nkat/mg towards ABTS at pH 4.5, laccase enzymes, which show at least 78% identity to the amino acid sequence SEQ ID NO:45 (TaLcc4) and have a specific activity of at least 900, preferably at least 1000 nkat /mg towards ABTS at pH 4.5.

Within the scope of the present invention are also laccase enzymes, which show at least 74% identity to the amino acid sequence SEQ ID NO:47 (CtLcc1) and has a specific activity of at least 600, preferably at least 700 nkat /mg towards ABTS at pH 4.5.

The production of laccase can also be improved by optimising the culture conditions and the culture medium of a wild or a recombinant strain. The carbon/nitrogen ratio can be optimised to be the best for the production of enzyme. The growing conditions, pH, temperature, mixing and air supply can be optimised to be the best possible for the enzyme production in question. In fermentation, inducers of laccase production, such as veratryl alcohol, xylidine, or lignin or other aromatic compounds can also be used. The way and the time of adding the inducers, as well as their concentration can be optimised.

The term "enzyme preparation" denotes here to any enzyme product, which contains at least one laccase enzyme. Thus, such an enzyme preparation may be a spent culture medium or filtrate containing one or more laccases or one or more laccases and other enzymes, an isolated laccase enzyme or a mixture of one or more laccase enzymes or a mixture of one or more laccase enzymes and one or more other enzymes. In addition to the laccase activity, such a preparation may contain additives, such as mediators, stabilizers, buffers, preservatives, surfactants and/or culture medium components. Preferred additives are such, which are commonly used in enzyme preparations intended for the application, where the enzyme preparation is used. The enzyme preparation may be in the form of liquid, powder or granulate.

The enzyme preparation may comprise in addition to laccase, one or more other enzymes, which may be for example amylases, cellulases and/or peroxidases. Alternatively, before, during or after the laccase treatment of the present invention, another enzyme treatment may be carried out. The enzyme treatment may comprise, for example, one or more amylase treatments, one or more cellulase treatments and/or one or more peroxidase treatments. Which other enzymes are included to the enzyme preparation or are used in the enzyme treatment, depends on the application.

The enzyme preparation may comprise one or more laccase enzymes of the present invention or other laccase enzymes together with one or more laccase enzymes of the present invention. For example, laccase enzymes having different properties may be combined to make the enzyme preparation more useful for different conditions.

By "mediators" are here meant additives which are often needed for enhancing the effect of laccases. Many of the prior art laccases do not function or do not function effectively in the absence of mediators. Also the laccases obtainable from *Thielavia* or *Chaetomium*, function more effectively in the presence of mediators. Suitable mediators include, for example methylsyringate, acetosyringon, ethylsyringate, butylsyringate and laurylsyringate, propionic acid-phenothiazine (PPT) 2,2'azinobis-3-ethylbenzthiazole-6-sulphonate (ABTS), 2,2,6,6-tetramethyl-1-piperidinyloxy (Tempo), 1-hydroxybenzotriazole (HBT), violuric acid, N-hydroxyacetanilide (NHA). The mediator may be used in the range 0.1 to 100 mg/g or 0.1 to 100 mg/l, preferably 1 to 10 mg/g or 1 to 10 mg/l of the treated material depending on the application.

Denim Bleaching

The enzymes of the present invention are in particular suitable for denim bleaching. By "increasing lightness" of denim is here meant a visible and measurable increase in the lightness in denim fabric. By "increasing lightness" of denim is meant in particular increasing lightness of denim on the face side of denim. The increase can be measured for example by measuring the colour as reflectance values with a chromameter using L*a*b* color space coordinates as described in Examples 7-10.

"Bleached look" means the effects, which are obtained on denim fabric in the prior art by means of bleaching chemicals, e.g. sodium hypochlorite. So far the "chlorine bleaching" has been the most effective bleaching method for denim dyed with Indigo since almost all shades have been obtained with it. If a "white bleaching" effect has been desirable, the bleaching has been carried out 2 to 3 times one after the other in different treatment baths, or by using high concentrations of hypochlorite. Bleaching with glucose, sulphinic acid derivatives or laccases have been suggested for denim treatment to replace sodium hypochlorite.

To "increase the lightness" of denim fabric, according to the prior art, treatment with various bleaching chemicals or enzymes is carried out. Bleaching is often done after treatment with cellulases or pumice stones or both.

When using the laccases of the present invention, if more whitish effect is desired, higher dosages can be used or the enzyme treatment can be repeated or combined with other bleaching methods. The laccase treatment of the present invention can be combined also with any other bleaching treatment, with one or more chemical bleaching treatments or with one or more other enzyme treatments having capability of increasing lightness of denim.

The denim treatment according to the invention comprises generally the following steps:

desized or optionally desized and cellulase treated denim is contacted in aqueous medium with an effective amount of laccase enzyme under suitable conditions for the function of the enzyme; and one or more rinses with water are carried out.

The laccase treatment is preferably carried out on cellulase treated denim. Laccase treatment is followed by one or more rinses with hot or cold water optionally with detergents. Enzyme inactivation is usually not needed after laccase treatment since it does not reduce the strength of fabric, but if needed it is carried out by methods well known to a person skilled in the art. The treatment is typically carried out in an equipment normally used for wet processes in textile industry, such as industrial machines used for washing, cellulase treatment, dyeing or finishing.

By "denim" is in connection of this invention meant denim fabric, usually denim jeans.

Performance of the laccase preparations of the present invention in denim bleaching was exemplified at different pH-values as described in the Example 7. Recombinant laccase preparations produced using *Thrichoderma* as a host were tested for their ability to bleach denim and compared to a commercial laccase preparation DeniLite II Base from Novozymes.

Figure 8:
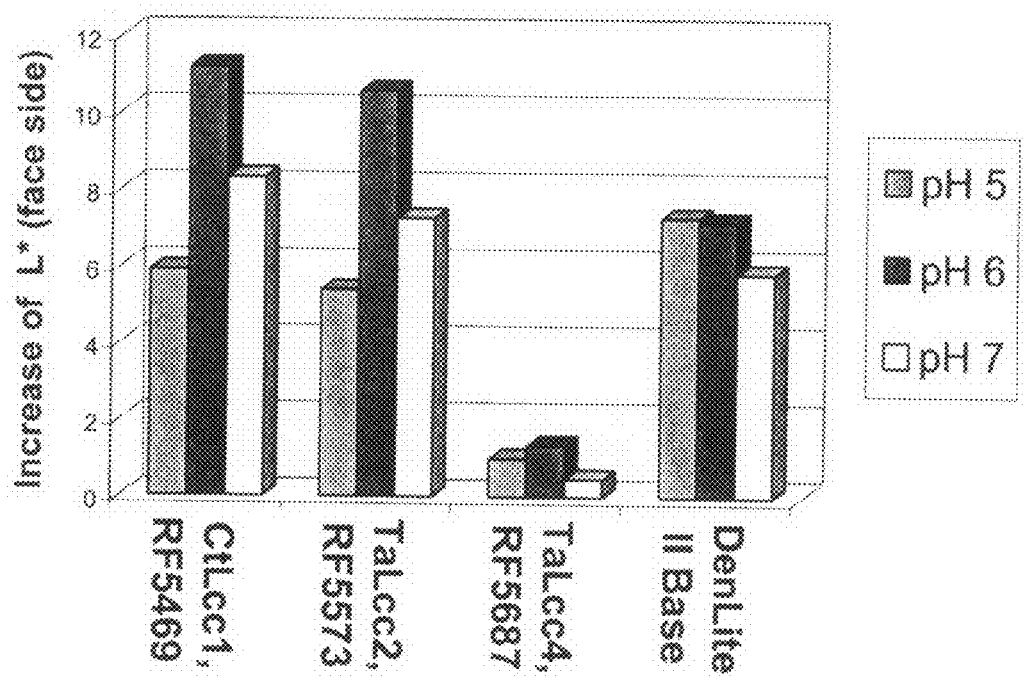
FIG. 8. The performance of laccase preparations in denim bleaching at different pH values at conditions described in Example 7.

Both CtLcc1 and TaLcc2 laccases were more efficient in decolorisation of indigo dye of denim compared to the prior art laccase at pH values 6 and 7 as can be seen in Table 18 and in FIG. 8. The look of the denim fabric was in particular at pH 6 much lighter.

The ability of the laccases of the present invention to bleach denim at different temperatures was tested and compared to the prior art laccase as described in Example 8.

CtLcc1 and in particular TaLcc2 were more efficient in decolorization of denim (higher increase of lightness) compared to the prior art laccase at 40 to 50° C. The two enzymes are thus very suitable for use in applications where low temperatures are preferred. However, CtLcc1 was more effective also at 60° C. and functions thus at broad temperature range.

According to a preferred embodiment of this invention denim treatment by the laccases of the present invention is carried out at the temperature of 30 to 80° C., preferably at the temperature of 40 to 70 ° C., more preferably at the temperature of 40 to 60° C. The pH during the treatment may be in the range from pH 3 to 9, preferably from pH 4 to 8, most preferably from pH 5 to 7. The treatment may be carried out in 15 minutes to 2 hours, preferably in 30 minutes to 90 minutes, more preferably in 30 minutes to 60 minutes.

The dosage used in the treatment can be 2 to 500 nkat, more preferably 20 to 200, most preferably 20 to 100 nkat/g fabric.

By the laccase enzyme of the present invention any kind of denim fabric can be treated. Advantageously the denim is Indigo dyed denim. By "Indigo dyed" is here meant that the denim to be treated is dyed with Indigo, with derivatives of Indigo or denim dyed with Indigo together with some other dye, for example indigo-dyed denim with sulphur bottom.

The denim fabric may be cellulase treated or stone washed, or both, or the denim fabric may be treated by laccase of the present invention already after desizing. Higher increasing of lightness of denim can be obtained when laccase treatment is carried out on cellulase treated fabric.

The "desizing" process is normally the first wet treatment of jeans and means the removal of starch or other sizing agents applied usually to the warp yarns to prevent damage during the weaving process. Alpha-amylases are used to remove starch-based size for improved and uniform wet processing. After desizing the jeans are normally rinsed with water.

The term "abraded" means here the appearance of denim fabric when it has been treated by cellulase enzymes or stone washed, or both. As a result of uneven dye removal there are contrasts between dyed areas and areas from which dye has been removed. Synonymous expressions are "stone washed look" or "worn look". The cellulase treatment may be done using neutral or acid cellulases or both. If a fabric is not cellulase treated or stone washed, the appearance of the fabric is said to be "dull", since the fashionable contrasts would be missing.

Stain Removal

The laccase enzymes of the present invention can be used also for stain removal under similar conditions as in denim bleaching.

According to a preferred embodiment of this invention denim treatment by the laccases of the present invention is carried out at the temperature of 30 to 80° C., preferably at the temperature of 40 to 70 ° C., more preferably at the temperature of 40 to 60° C. The pH during the treatment may be in the range from pH 3 to 9, preferably from pH 4 to 8, most preferably from pH 5 to 7. The treatment may be carried out in 15 minutes to 2 hours, preferably in 30 minutes to 90 minutes, more preferably in 30 minutes to 60 minutes.

The dosage used in the treatment can be 0.2 to 2000 nkat/g of fabric, preferably 1 to 500, more preferably from 2 to 200 nkat/g of fabric.

The laccases of the present invention and Denilite II Base laccase preparations were tested for their ability to remove stains as is described in Example 9. In the tests artificially soiled test cloths for grass soiling and for tea soiling were used with or without the mediator (methyl syringate). The dosages of the enzymes were 20 and 200 nkat/g of fabric and the test was run at 40, 50 or 60° C. and pH 6 for 60 min.

As can be seen in Tables 21 and 22 and in FIGS. 10 to 13 CtLcc1 laccase was effective in removal of grass and tea soiling with mediator at 60° C. and TaLcc2 laccase at 50° C. The effect was also seen at 40° C.

Decolorization of Dyes

The laccase enzymes of the present invention can be used also in decolorization of dyes. Dye-house effluents, for example cannot be discharged to natural waters without degrading the dyes and/or decolorizing them. The decolorization can be carried out under similar conditions as used in denim bleaching. Suitable dosage of the enzyme and treatment time depends on the amount of the dye to be decolorized and the treatment conditions.

According to a preferred embodiment of this invention decolorization of dyes is carried out at the temperature of 30 to 80° C., preferably at the temperature of 40 to 70° C., more preferably at the temperature of 40 to 60° C. The pH during the treatment may be in the range from pH 3 to 9, preferably from pH 4 to 8, most preferably from pH 5 to 7.

The enzyme dosages and treatment times can be tested and chosen to be most suitable for the application. As guidance can be used dosages of 0.2 to 2000 nkat/l of the treatment solution. The treatment time is preferably 15 min to 24 hours, more preferably 30 min to 12 hours. If the treatment is carried out at lower temperature, for example 18 to 30° C. the treatment time may be longer.

As described in Example 10 the laccases of the present invention were tested for their ability to decolourize different dyes in the presence or absence of a mediator. CtLcc1 and TaLcc2 laccases were able to decolorize Indigocarmine and Remazol Brilliant Blue very effectively. Also Cibacron Brilliant Red 3B-P was partly decolorized.

Other Applications

Since the laccases of the present invention have high oxidizing capacity of various substrates, they are well suited for many industrial applications. Such applications are for example the manufacture of fibre products and applications of forest industry, applications in cosmetic industry and in industry preparing personal care and other applications. In these applications, the temperature and pH are on the area where the laccases of the present invention function. The dosage and treatment time can be chosen depending on the application and material to be treated.

Mediators may be needed as additives to enhance the effect of the laccases of the present invention. In addition, it is essential that enough oxygen is brought to the reaction. If needed, oxygen can be added either by bringing air or oxygen or air enriched with oxygen to the reaction mixture.

The laccases of the present invention are suitable for use in textile industry, for treating man-made or natural fibers or their combinations. The enzyme is suitable for treating cellulosic fibers as well as proteinaceous fibers, such as wool or silk.

The laccases of the present invention are suitable for use in forest industry. Lignin-containing fibres can be brought into contact with the laccase. Due to the laccase treatment, the strength properties of the fibres improve, which can be utilised, for example, in the manufacture of fibre boards, in paper or cardboard products and composites, which are made of mechanically ground lignin-containing fibres. Wood fibers can be treated with laccases of the present invention also to functionize them or glue the fibers.

The laccases of the present invention are also well suited to depolymerization of various compounds. By using the laccases of the present invention lignin in kraft pulp can be depolymerised thereby producing a pulp with lower lignin content. Laccase can thus be used for bleaching of pulp to decrease the use of bleaching chemicals. As a result of the better bleachability of the pulp after laccase treatment, there is a reduction of the subsequent consumption of bleaching chemicals, which when chlorine containing chemicals are used, leads to a reduced formation of environmentally undesired organochlorine compounds.

The laccases of the present invention can be used also for polymering compounds, such as lignin, to produce high molecular weight compounds.

Because of the high oxidizing capacity of the enzyme it can be used for oxidizing of dyes or dye precursors or chromophoric compounds in cosmetic industry or in industry preparing products for personal care. The oxidation of the dyes leads to decolorization of the compounds. This effect can be used for example in hair dyeing or when whitening teeth. To carry out hair dyeing dye precursors or modifiers are usually needed.

The laccase according to the invention can also be used to improve the runnability of paper machines. The laccase can be used to improve the runnability of paper machines by polymerising compounds originating from lignin and extractives and by decreasing the detrimental growth of microbes in the paper machine.

Further possible applications where laccase enzymes of the present invention can be used are methods for improving doughs in baking applications, methods for clarifying beer and wine, use in improval of the production of fuel ethanol from renewable raw materials and use in various bioremediative processes as well as use in hard-surface cleaning or in detergent formulations.

In general, in the mentioned applications the treatment temperature is preferably 30 to 80° C., more preferably 40 to 70° C., although reactions can be carried out also at lower temperatures. The pH may be 3 to 9, preferably 4 to 7. The treatment time may be 15 min to 24 hours, preferably 30 min to 2 hours. The dosage may be 0.1 to 2000, preferably 1 to 1000, more preferably 2 to 200 nkat/g or 1 of the material to be treated. A suitable amount of mediator may be added.

Compositions for the mentioned applications comprise the enzyme or enzyme preparation of the present invention in an effective amount and optionally additives suitable for the application in question. Compositions for textile industry may comprise for example a suitable amount of surface active agents, buffers, stabilizers and preservatives, compositions for forest industry may comprise for example a suitable amount of buffers, stabilizers and preservatives. In all compositions should be avoided substances harmful for environment and for human (or animal) use. In particular compositions for cosmetic industry and industry for personal care products should not contain harmful effects on skin or as ingested.

The present invention provides composition for the treatment of denim comprising a laccase enzyme or an enzyme preparation according to the invention. The present invention provides also a composition for removal of stain, a composition for bleaching of pulp, a composition for treating of fibre for textile industry, a composition for treating of fibre for forest industry, a composition for treating of wool, a composition for treating of hair, a composition for treating of dye house effluent, and a composition for decolorizing of dyes comprising a laccase enzyme or an enzyme preparation according to the invention.

The following examples are intended for illustration of the present invention and should not be interpreted as limiting the present invention in any way.

EXAMPLE 1

Production and Purification of the *Thielavia arenaria* and *Chaetomium thermophilum* Laccase Production of the *Thielavia arenaria* and *Chaetomium thermophilum* laccase Various strains from the culture collection of Roal Oy were screened for their ability to produce laccases with indicators Remazol Brilliant Blue R-478, tannic acid, and guaiacol as described in Kiiskinen et al. (2004). *Thielavia arenaria* ALKO4197 showed positive reactions on guaiacol and Remazol Brilliant Blue R-478, and *Chaetomium thermophilum* ALKO4265 showed strong positive reaction, when 5 mM ABTS solution in 25 mM succinate buffer (pH 4.5) or in 25 mM McIlvaine buffer (pH 6.0) was dropped onto fresh mycelium on agar plates.

Both fungi were maintained on PD agar (Difco) at +4° C. The inoculation and production medium contained: 25 g/l glucose (AnalaR), 27.5 g/l Bacto yeast extract (Difco), 0.5 mg/ml Indulin AT (Sigma), 0.04 l/l mineral solution (1.0 g/l $CaCl_2.2H_2O$ (Riedel-de Haën), 1.0 g/l $FeSO_4.7H_2O$ (Riedel-de Haën), 0.1 g/l $ZnSO_4.7H_2O$ (Merck), 0.16 g/l $CuSO_4.5H_2O$ (Merck), 1.0 g/l $Na_2EDTA$ (Riedel-de Haën)). Glucose was sterilized separately and combined aseptically to the medium.

The *Thielavia arenaria* ALKO 4197 strain was cultivated in 50 or 200 ml volume on a rotary shaker (200 rpm) at temperature of 37° C. The medium was inoculated with 5 or 20 ml of well-grown mycelia. The laccase activity was followed up to eight days and the highest laccase activity (about 20 nkat/ml) was reached after six days of cultivation (FIG. 1A). Six parallel cultivations were made. Cells were removed from the fermentation broth by centrifugation (10 000 g for 10 min, at +4° C.) and the culture filtrate was further purified.

Figure 1B:
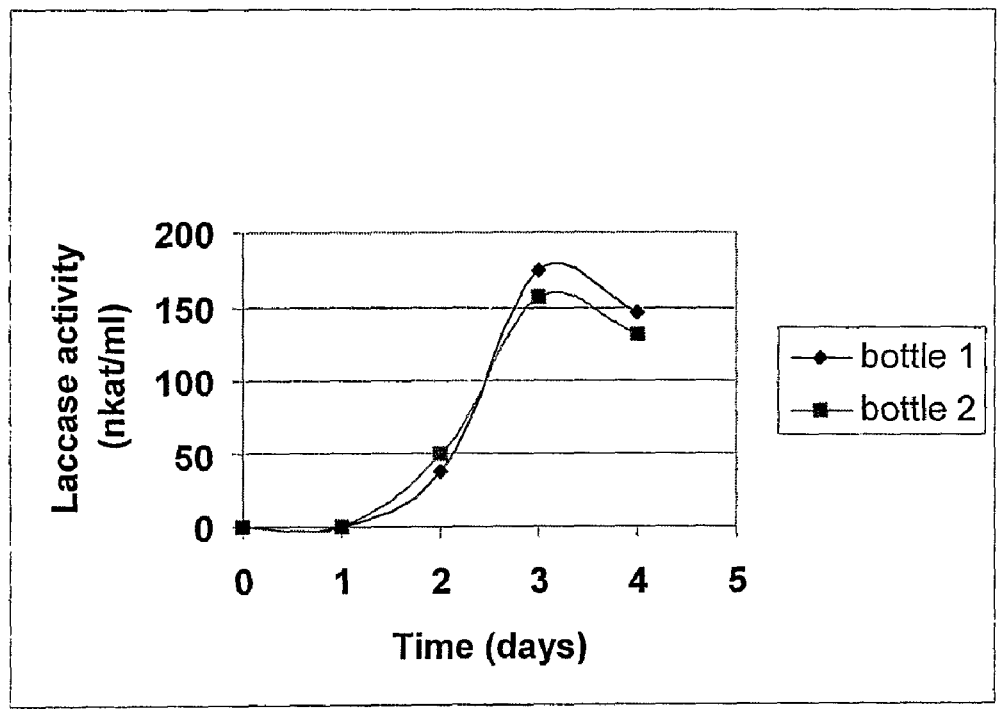
FIG. 1B. Production of the *Chaetomium* laccase in 50 ml shake flask cultivation.

The *C. thermophilum* ALKO 4265 strain was cultivated in 50 or 200 ml volume on a rotary shaker (200 rpm) at temperature of 42° C. The medium was inoculated with 5 or 20 ml of well-grown mycelia. The laccase activity was followed up to four days and the highest laccase activity (about 170 nkat/ml) was reached after three days of cultivation (FIG. 1B). Six parallel cultivations were made. Cells were removed from the fermentation broth by centrifugation (10 000 g for 10 min., at +4° C.) and the culture filtrate was further purified.

Purification of the *Thielavia* and *Chaetomium* Laccases

Figure 2A:
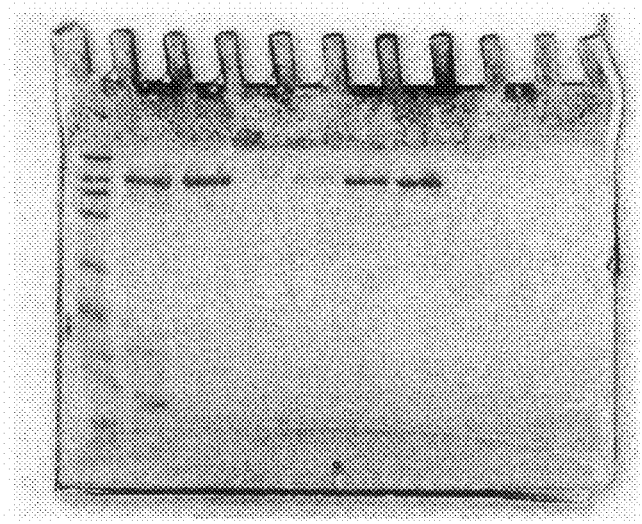
FIG. 2A. SDS-PAGE (15%) showing the purification of *Thielavia* laccase. 1 MW marker (175, 83, 62, 47, 32.5, 25, 16.5, and 6.5 kDa), 2 culture supernatant, 3 after DEAE Sepharose, 4-7 fractions after gel filtration, about 3-6 μg protein loaded on each lane. Proteins are stained with Coomassie Brilliant Blue.

Concentrated culture filtrate of the crude *Thielavia* laccase was first loaded on Q Sepharose FF column (Pharmacia, V=26 ml), which was pre equilibrated with 10 mM Tris HCL, pH 8.5. Proteins were eluted with an increasing salt gradient (0-500 mM $Na_2SO_4$ in the equilibrating buffer, within 5 column volumes). Laccase active fractions eluted at 70-150 mM salt concentration and they were pooled and loaded on Sephacryl S100 gel filtration resin (Pharmacia, V=160 ml), which was equilibrated with 20 mM Tris-buffer, pH 7.0, containing 200 mM NaCl. Purification was followed by SDS-PAGE stained with Coomassie brilliant Blue (FIG. 2A). Laccase positive fractions were pooled and concentrated. Salts were removed and buffer changed to 20 mM Tris buffer, pH 7.0. In order to obtain high purity samples an additional Resource Q anion exchange step was included. The sample was loaded onto a Resource Q column (Pharmacia, V=1 ml), which was equilibrated with 10 mM Tris HCl pH 8.5. Proteins were eluted with a linear 1-300 mM $Na_2SO_4$ salt gradient within 12 column volumes.

Figure 2B:
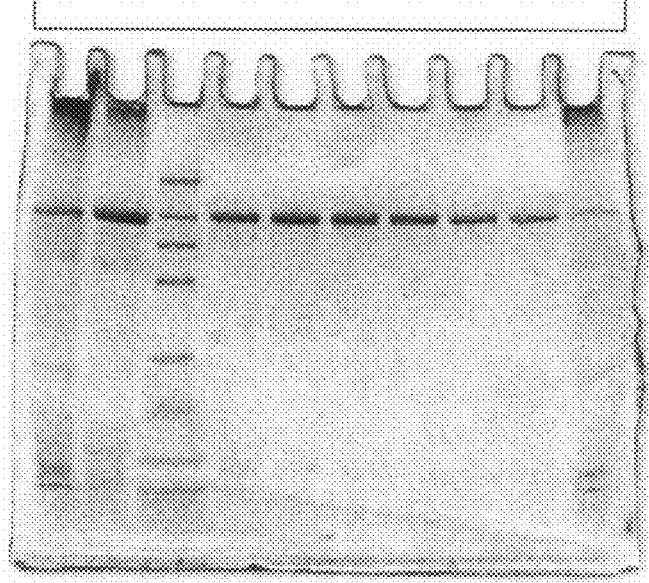
FIG. 2B. SDS-PAGE (12%) from the purification of *Chaetomium* laccase. 1 culture supernatant (69 μg), 2 after ion exchange (14.5 μg), 3 MW standard (175, 83, 62, 47.5, 32.5, 25, 16.5, 6.5 kDa), 4-9 fractions from HIC (3.5, 3.3, 3.1, 2.4, 2.0, and 1.5 μg), 10 culture supernatant (30 μg).

The culture supernatant of *C. thermophilum* was concentrated and the buffer changed to the binding buffer by ultrafiltration (MWCO 10 000). Proteins were bound to DEAE Sepharose FF (Pharmacia, column volume 25 ml) at 20 mM Tris-buffer pH 8.0. Proteins were eluted with a sodium sulphate gradient (0-500 mM). The laccase positive fractions eluted at 150-200 mM salt concentration, and they were pooled and further purified with hydrophobic interaction chromatography (Phenyl Sepharose FF, Pharmacia, column volume 22 ml). Proteins were bound at 500 mM sodium sulphate concentration, at 20 mM Tris buffer pH 7.0, and eluted with a decreasing salt gradient (500-0 mM). The laccase positive fractions eluted with 20 mM Tris buffer. Purity of the fractions was analyzed by SDS-PAGE and subsequent Coomassive staining (FIG. 2B.).

Enzyme Activity Assay

The laccase activity from the culture supernatant was measured using ABTS as substrate. The activity assay was carried out in accordance with the method developed by Niku-Paavola et al. (1988). The sample was diluted with 0.025 M succinate buffer, pH 4.5. 0.350 ml of ABTS solution (11 g/l) was added to 1.15 ml of the dilution, and the reaction was followed for 2 minutes by the Perkin Elmer Lambda 20 spectrophotometer at a wavelength of 436 nm. The activity is expressed as nano katals.

Determination of Protein Contents

The protein contents were determined by the DC Protein Assay kit of Bio-Rad, based on a method developed by Lowry et al. (1951). The assays were carried outaccording to the supplier's instructions, and the intensity of the colour formed in the reaction was measured on a wavelength of 750 nm using the. Perkin Elmer Lambda 20 spectrophotometer. A standard curve was defined using bovine serum albumin in concentrations of 0.25-1.25 g/l (BSA, Bio-Rad).

EXAMPLE 2

Characterization of the Purified *C. thermophilum* Laccase

Molecular Weight and pI

Molecular weight of the *T. arenaria* and *C. thermophilum* laccases were determined on SDS-PAGE according to Laemmli (1970) The gels used in the SDS-PAGE analysis were ready-made 12% Tris HCl gels (BioRad). Protein bands were visualized by staining with Coomassie Brilliant Blue (R 350; Pharmacia) and compared with molecular weight markers (Prestained Protein Marker Broad Range #7708S; New England BioLabs, Beverly, Mass.). The molecular weight of the both laccases was approximately 80 kDa. The isoelectric point of the laccases was determined with isoelectric focusing within the pH range of 3-9 (Pharmalyte IEF, Pharmacia) on a LKB 2117 Multiphor II Electrophoresis System (LKB Pharmacia, Bromma, Sweden) according to the manufacturer's instructions. Bands containing laccase activity were visualized by staining the gel with 2 mM ABTS in 25 mM succinate buffer (pH 4.5) and proteins by Coomassie Blue staining. The purified *Thielavia* laccase showed multiple bands in isoelectric focusing at pIs 5.5, 5.9, 6.4, 6.8, and 6.9. The purified *C. thermophilum* laccase showed 3-4 bands in isoelectric focusing at pIs 4.1-4.3.

pH Optimum

Figure 3A:
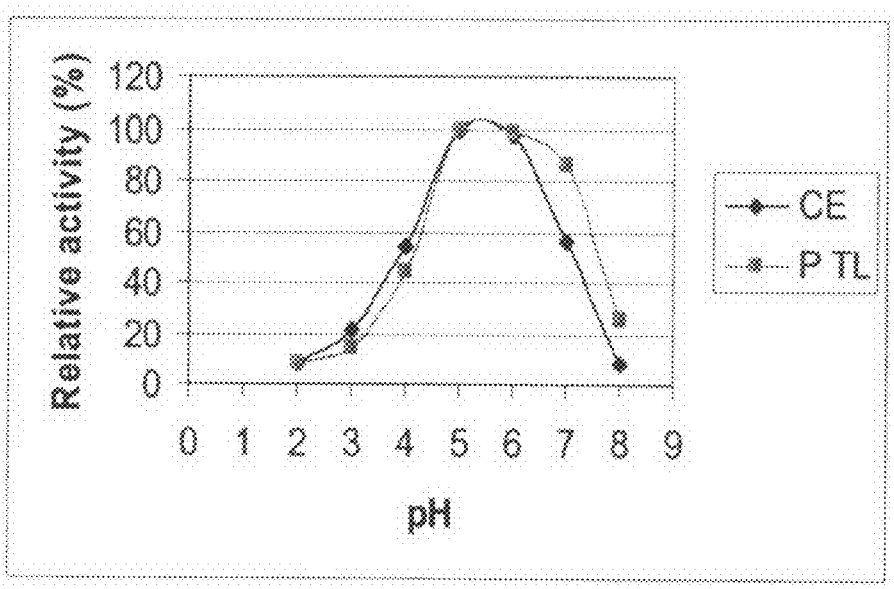
FIG. 3A. pH optima of the purified *Thielavia* laccase (P TL) and the crude enzyme (CE) determined on guaiacol.
Figure 3B:
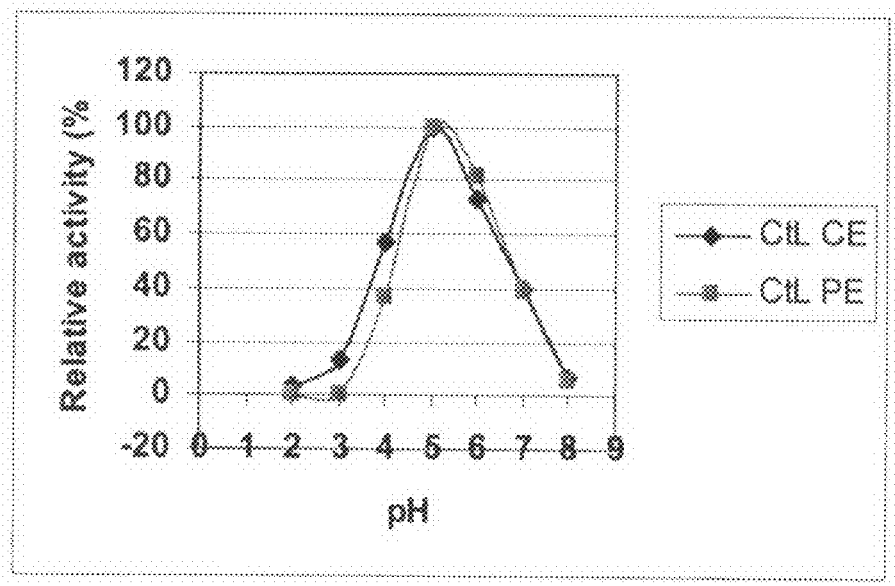
FIG. 3B. pH optima of the purified *Chaetomium* laccase (P TL) and the crude enzyme (CE) determined on guaiacol.

The pH-optimum of the *T. arenaria* and *C. thermophilum* laccases were determined in the universal McIlvaine buffer within a pH range of 2.2-8.0 using guaiacol as substrate. The pH optima determined for the purified and crude *Thielavia* laccase are shown in FIG. 3A. As shown in FIG. 3A the pH optimum for *Thielavia* laccase is at 5.5, the enzyme shows substantially high activity still at pH 7, above which the activity starts to drop. The pH optimum of the purified and crude *C. thermophilum* laccase is at 5.0 (FIG. 3B).

Thermal Stability

Figure 4A:
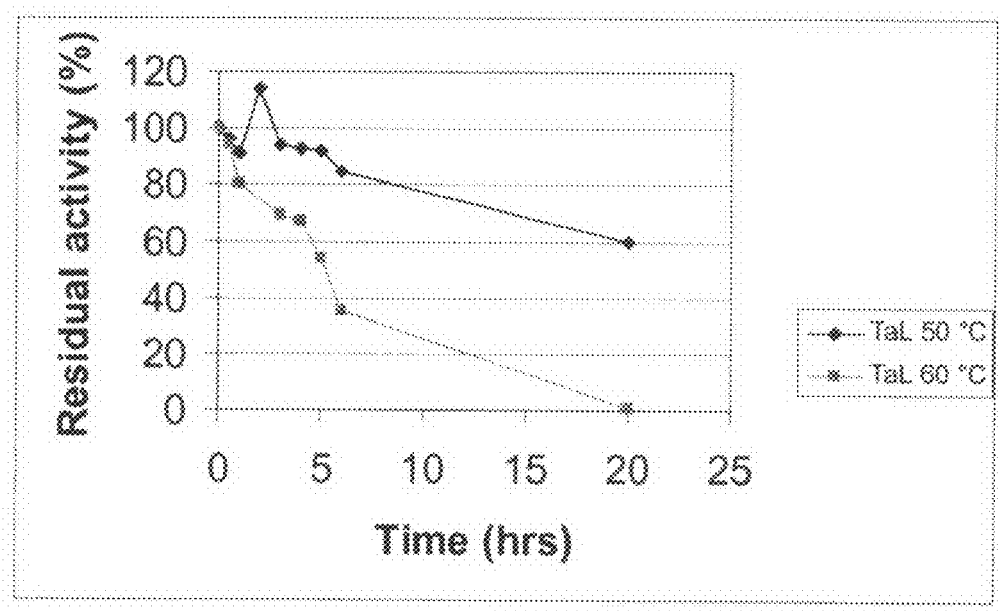
FIG. 4A. Thermal stability of *Thielavia* laccase at 50 and 60° C.
Figure 4B:
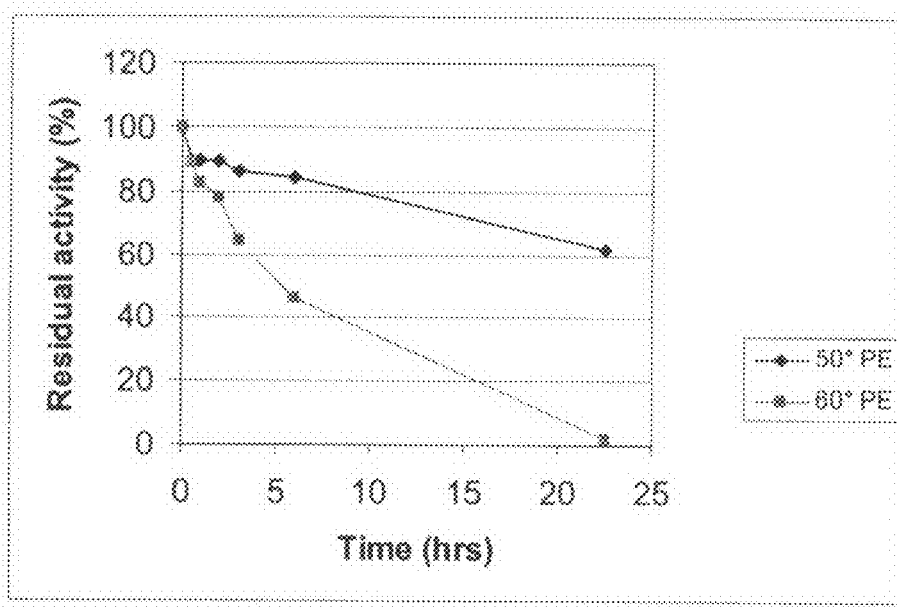
FIG. 4B. Thermal stability of *Chaetomium* laccase at 50 and 60° C.

Thermal stability of the laccases were determined by incubating the enzyme solution (0.3 $gl^{-1}$) in 60 mM citrate buffer (pH 6). The residual enzyme activities were measured at on ABTS. As shown from the results the half lives of the *Thielavia* laccase was 26 and 5.5 hrs at 50, and 60° C., respectively (FIG. 4A), and for *C. thermophilum* 30 and 6 hrs 50, and 60° C., respectively (FIG. 4B).

Specific Activity

Specific activities of the purified *T. arenaria* and *C. thermophilum* laccases were determined towards different laccase substrates. The activities were determined towards ABTS (Niku-Paavola et al., 1988), di-methoxy-phenol (DMP) (Schlosser et al., 1997), syringaldazine (Paszczynski et al., 1985), and guaiacol (Leonowicz & Grzywnowicz, 1981). For ABTS the activity measurements were carried out in 25 mM succinate buffer pH 4.5 at 25° C. and for other substrates in 25 mM MES buffer, pH 5.5. Results are shown in Table 1.

TABLE 1

Specific activities of the purified wild type *Thielavia* (TaLcc) and *Chaetomium* (CtL) laccases.

| Substrate | Spec. act TaLcc nkat/mg | Spec. act. CtL nkat/mg |
|---|---|---|
| ABTS | 1020 | 705 |
| DMP | 260 | 290 |
| syringaldazin | 490 | 400 |
| guaiacol | 63 | 85 |

Inhibition of the Laccase

The effect of various inhibitors on laccase activity was determined by measuring the oxygen consumption during the enzyme reaction with ABTS in sealed and fully filled Erlenmeyer flasks with an Orion Research 081010 oxygen electrode (Software: SensorLink™ PCM800; Orion, Espoo, Finland). The oxygen consumption rates were measured from solutions containing suitable amount of the laccase, 2 mM ABTS, and various inhibitors in different concentrations, in 50 mM citrate buffer (pH 5) in a 30 ml reaction volume

TABLE 2

Inhibition of the wild type *Thielavia* (TaLcc) and *Chaetomium* (CtL) laccases.

| Compound | Concentration | Inhibition (%) TaLcc | Inhibition (%) CtL |
|---|---|---|---|
| EDTA | 10 mM | 0 | 0 |
| NaN3 | 0.5 mM | 99 | 100 |
| KCN | 0.1 mM | 65 | 70 |
| KCN | 1 mM | ND | 100 |
| NaCl | 0.1 mM | 35 | 0 |
| NaCl | 1 mM | 42 | 10 |
| NaF | 0.5 mM | ND | 40 |
| NaF | 10 mM | ND | 70 |

N-Terminal and Internal Amino Acid Sequencing

The N-terminus of the protein as well as the internal peptides were sequenced according to Edman degradation chemistry (Edman and Begg, 1967) using PE Biosystems Procise Sequencer. For peptide preparation, the lyophilized protein was reduced with dithiotreitol, carboxymethylated with iodoacetamide and cleaved with sequencing grade trypsin (Promega) at enzyme/substrate mass ratios 1:100 for 12 hours at 37 C in 0.1 M ammoniumbicarbonate, pH 8.3 (Stone et al., 1988). Generated peptides were separated by reversed-phase high performance liquid chromatography (RP-HPLC, Vydac C-18 column) with a linear acetonitrile gradient (0-60% acetonitrile in 0.1% trifluoroacetic acid). The internal peptide sequences for *Thielavia* laccase are shown in Table 3 (SEQ ID NO: 1-3). The N-terminus of the protein could not be obtained, because it was presumably blocked. Amino acid sequences obtained from the *Chaetomium*-laccase are shown in Table 4 (SEQ ID NO: 4-7). The sequences of the peptides 22.4 and 22.7 from *Chaetomium* were obtained after the corresponding laccase gene had been cloned.

TABLE 3

Internal peptide sequences determined from *Thielavia*-laccase (ALKO4197). The N-terminus of the protein was presumably blocked.

| Peptide | Sequence | Comments |
|---|---|---|
| Peptide 1 | YQGAPNTLPTNQGLPVPNH (SEQ ID NO: 1) | An equal Ile signal can also be seen in the 12th cycle. |
| Peptide 2 | ENWIGPDGVLK (SEQ ID NO: 2) | |
| Peptide 3 | (S)LFLAVGQR (SEQ ID NO: 3) | (S), result unsure. |

TABLE 4

N-terminal and internal peptide sequences of *C. thermophilum* laccase (ALKO4265).

| Peptide | Sequence | Comments |
|---|---|---|
| N-terminus | E(AD)GPGPCHTPANYACWAPGFD (SEQ ID NO: 4) | In addition to Glu, equal Ala and Asp signals can be seen in the first cycle |
| Peptide 18.9 | LTENDNWTGPDGVVK (SEQ ID NO: 5) | |
| Peptide 22.4 | DHNCLDLLDLVPVVPR (SEQ ID NO: 6) | |
| Peptide 22.7 | T(S)LGGTPT(L)FVXK (SEQ ID NO: 7) | The amino acid in the first cycle can be Thr or Ser and on the seventh cycle Thr or Leu. X, result unsure. |

EXAMPLE 3

Cloning of the *Thielavia arenaria* ALKO 4197 and *Chaetomium thermophilum* ALKO4265 Laccase Genes Standard molecular biology methods were used in the isolation and enzyme treatments of DNA (plasmids, DNA fragments), in *E. coli* transformations, etc. The basic methods used are described in the standard molecular biology handbooks, e.g. Sambrook et al. (1989) and Sambrook and Russell (2001).

The genomic libraries of *Thielavia arenaria* ALKO 4197 and *Chaetomium thermophilum* ALKO 4265 were made to Lambda DASH®II vector (Stratagene, USA) according to the instructions from the supplier. The chromosomal DNAs, isolated by the method of Raeder and Broda (1985), were partially digested with Sau3A. The digested DNAs were size-fractionated and the fragments of the chosen size (9-23 kb) were dephosphorylated and ligated to the BamHI digested lambda vector arms. The ligation mixtures were packaged using either Gigapack III XL (*Thielavia*) or Gigapack III Gold (*Chaetomium*) packaging extracts according to the manufacturer's instructions (Stratagene, USA). The titers of the *Thielavia* and *Chaetomium* genomic libraries were $1.2 \times 10^6$ and $3.6 \times 10^6$ pfu/ml and those of the amplified libraries were $1.1 \times 10^{10}$ and $6.5 \times 10^{10}$ pfu/ml, respectively.

The probes for screening the gene banks were amplified by PCR using the *Thielavia* ALKO 4197 and *Chaetomium* ALKO 4265 genomic DNAs as templates in the reactions.

First, several primers (degenerate oligos) were planned and tested in PCR reactions (Table 5, SEQ ID NO: 8-31). The sequences of the homologous primers based on the amino acid sequences of the peptides from the purified TaLcc1 and CtLcc1 and the heterologous primers were planned according to the conserved laccase sequences (FIG. 5). The conserved sequences were identified by aligning the previously published amino acid sequences of *Neurospora, Podospora, Cryphonectria, Myceliophthora, Scytalidium* and *Coprinus* laccases (EMBL accession numbers P10574, P78722, Q03966, AAE68088, AAE68087, AAE63570, AAE63572, and AAE63571). In addition, a heterologous probe was amplified from the *N. crassa* laccase gene (genomic DNA from *N. crassa* strain ATCC9277 was used as a template), using primers POX12 and POX13 designed according to the published nucleotide sequence (Table 5). The combinations of the primers for the PCR reactions were selected according to the location of the peptide or the peptide homologue in the published laccase sequences. The PCR reaction mixtures contained 50 mM Tris-HCl, pH 9.0, 15 mM $(NH_4)_2SO_4$, 0.1% Triton X-100, 5% DMSO, 1.5-3 mM $MgCl_2$, 0.2 mM dNTPs, 5 µM each primer and 1-2 units of Dynazyme EXT DNA polymerase (Finnzymes, Finland) and 1-5 µg of the genomic DNA. The conditions for the PCR reactions were the following: 5 min initial denaturation at 95° C., followed by 25-30 cycles of 1 min at 95° C., 1 min annealing at 50° C. (*Thielavia* DNA as a template) or at 50 or 42° C. (*Chaetomium* DNA as a template), 2 min extension at 72° C. and a final extension at 72° C. for 7-10 min.

TABLE 5

The oligonucleotides tested as PCR primers to amplify probes for screening of the laccase genes. Oligo, oligonucleotide; Oligo location, the amino acids of the peptide used in planning of the oligonucleotide sequence.

| Oligo | Length (nts) | Degeneracy[a] | Sequence[b] | Peptide[c] | Oligo loc. |
|---|---|---|---|---|---|
| POX1 | 17 | 16 | AAYTAYGCXTGYTGGGC (s) (SEQ ID NO: 8) | Ct Lcc1 N-term | 11-16 |
| POX2 | 17 | 16 | GCCCARCAXGCRTARTT (as) (SEQ ID NO: 9) | Ct Lcc1 N-term | 11-16 |
| POX22 | 32 | 16 | TGCCAYACSCCCGCYAACTACGCYTGCTGGGC (s)[e] (SEQ ID NO: 10) | Ct Lcc1 N-term | 6-16 |
| POX3 | 17 | 16 | GTCCARTTRTCRTTYTC (as) (SEQ ID NO: 11) | Ct Lcc1 18.9 | 3-8 |
| POX16 | 17 | 16 | GARAAYGAYAAYTGGAC (s) (SEQ ID NO: 12) | Ct Lcc1 18.9 | 3-8 |
| POX23 | 32 | 8 | GAGAACGAYAACTGGACSGGCCCCGAYGGCGT (s)[e] (SEQ ID NO: 13) | Ct Lcc1 18.9 | 3-13 |
| POX26 | 26 | 8 | GAGAACTGGATCGGYCCCGAYGGYGT (s) (SEQ ID NO: 14) | Ta Lcc1 2 | 1-9 |
| POX27 | 17 | 48 | GARAAYTGGATHGGXCC (a) (SEQ ID NO: 15) | Ta Lcc1 2 | 1-6 |
| POX28 | 20 | 16 | CTCTTCCTCGCYGTSGGYCA (s) (SEQ ID NO: 16) | Ta Lcc1 3 | 2-8 |

TABLE 5-continued

The oligonucleotides tested as PCR primers to amplify probes for screening of the laccase genes. Oligo, oligonucleotide; Oligo location, the amino acids of the peptide used in planning of the oligonucleotide sequence.

| Oligo | Length (nts) | Degeneracy[a] | Sequence[b] | Peptide[c] | Oligo loc. |
|---|---|---|---|---|---|
| POX29 | 20 | 16 | TGRCCSACRGCGAGGAAGAG (as) (SEQ ID NO: 17) | Ta Lcc1 3 | 2-8 |
| POX30 | 20 | 8 | TACCAGGGYGCYCCSAACAC (s) (SEQ ID NO: 18) | Ta Lcc1 1 | 1-7 |
| POX31 | 20 | 8 | GTGTTSGGRGCRCCCTGGTA (as)[e] (SEQ ID NO: 19) | Ta Lcc1 1 | 1-7 |
| POX4 | 17 | 64 | TGGTAYCAYWSXCAYTT (s) (SEQ ID NO: 20) | Homol. I | 1-6 |
| POX5 | 17 | 64 | AARTGXSWRTGRTACCA (as) (SEQ ID NO: 21) | Homol. I | 1-6 |
| POX6 | 20 | 64 | ATGCAYYTXCAYGGXCAYGA (s) (SEQ ID NO: 22) | Homol. II | 1-7 |
| POX7 | 20 | 64 | TCRTGXCCRTGXARRTGCAT (as) (SEQ ID NO: 23) | Homol. II | 1-7 |
| POX8 | 17 | 64 | CAYYTXCAYGGXCAYGA (s) (SEQ ID NO: 24) | Homol. II | 2-7 |
| POX9 | 17 | 64 | TCRTGXCCRTGXARRTG (as) (SEQ ID NO: 25) | Homol. II | 2-7 |
| POX10 | 23 | 48 | TGCCAXGCDATRTGRCARTGCAT (as) (SEQ ID NO: 26) | Homol. III | 1-8 |
| POX11 | 20 | 48 | TGCCAXGCDATRTGRCARTG (as) (SEQ ID NO: 27) | Homol. III | 2-8 |
| POX12 | 17 | Ncr codons | TGGTACCACTCGCATTT (s)[d] (SEQ ID NO: 28) | Homol. I | 1-6 |
| POX13 | 17 | Ncr codons | TCGTGGCCGTGCAGGTG (as)[d] (SEQ ID NO: 29) | Homol. II | 2-7 |
| POX14 | 23 | Ncr codons | TGCCAGGCAATGTGGCAGTGCAT (as)[d] (SEQ ID NO: 30) | Homol. III | 1-8 |
| POX15 | 20 | Ncr codons | TGCCAGGCAATGTGGCAGTG (as)[d] (SEQ ID NO: 31) | Homol. III | 2-8 |

[a]To reduce degeneracy, some codons were chosen according to the fungal preference.
[b]D = A or G or T, H = A or C or T, R = A or G, S = C or G, W = A or T, X = I (inositol) or C, Y = T or C, "s" in the parenthesis = sense strand, "as" in the parenthesis = antisense strand.
[c]The peptide sequences are included in FIG. A.
[d]Neurospora crassa codons were used (from sequence: EMBL M18334)
[e]The codon usage chosen according to the xylanase genes xyn11A, xyn11B and xyn11C isolated from C. thermophilum ALKO4265 (EMBL AJ508931-508933).

DNA products having the expected sizes (calculated from the published fungal laccase sequences) were obtained from several reactions. In some of the PCR reactions, several bands were detected that had very similar sizes; e.g. three bands of about 0.2 kb were obtained with the primers POX8 and POX11 from the reactions with *Chaetomium* DNA. This suggested that several laccase genes can be found. The DNA fragments having the expected sizes were isolated from the most specific PCR reactions and they were cloned to pCR® Blunt-TOPO® vector (Invitrogen, USA). The inserts were characterized by sequencing and by performing Southern blot hybridizations to the genomic DNAs digested with several restriction enzymes.

The PCR products obtained from both the *Thielavia* and *Chaetomium* reactions were found to contain sequences from three different genes, according to the hybridization patterns and sequencing. Three PCR fragments, each representing a different putative laccase gene (Table 6, SEQ ID NO: 32-37), were chosen from both *Thielavia* and *Chaetomium* reactions to be used as probes for screening the gene banks. The deduced amino acid sequences from all these probes had homology to several published laccase sequences (BLAST program, version 2.2.9 at NCBI, National Center for Biotechnology Information; Altschul et al., 1990). In addition to the homologous probes, the heterologous *N. crassa* laccase fragment was used for screening both the gene banks.

TABLE 6

The primers used in the PCR reactions and probes chosen for screening of the laccase genes. The genomic template DNA and the name of the plasmid containing the probe fragment are shown.

| Gene | Forward primer | Reverse primer | Template DNA used in PCR reaction | Fragment obtained (kb) | Insert in plasmid |
|---|---|---|---|---|---|
| Talcc1 | POX27 | POX31 | *T. arenaria* ALKO4197 | 1.0 kb | pALK1550 |
| Talcc2 | POX4 | POX11 | *T. arenaria* ALKO4197 | 1.3 kb | pALK1601 |
| Talcc3 | POX27 | POX9 | *T. arenaria* ALKO4197 | 1.3 kb | pALK1624 |
| Talcc4 | POX12 | POX15 | *N. crassa* ATCC9277 | 1.1 kb | — |
| Ctlcc1 | POX8 | POX11 | *C. thermophilum* ALKO4265 | 0.2 kb | pALK1299 |
| Ctlcc2 | POX4 | POX9 | *C. thermophilum* ALKO4265 | 0.9 kb | pALK1295 |
| Ctlcc3 | POX8 | POX11 | *C. thermophilum* ALKO4265 | 0.25 kb | pALK1296 |

The *N. crassa* laccase fragment and the inserts from the plasmids listed in Table 6 were labeled by using digoxigenin according to the supplier's instructions (Roche, Germany). The amplified genomic libraries ($8 \times 10^4$-$1 \times 10^6$ plaques) were screened with the homologous probe fragments and with the *N. crassa* laccase fragment. The hybridization temperature for the filters was 68° C. and the filters were washed 2×5 min at RT using 2×SSC-0.1% SDS followed by 2×15 min at 68° C. using 0.1×SSC-0.1% SDS when the homologous probes were used. The filters probed with the *N. crassa* laccase fragment were washed 2×5 min at RT using 2×SSC-0.1% SDS followed by 2×15 min at 68° C. using 2×SSC-0.1% SDS. Several positive plaques were obtained from each of the hybridizations. Some of the positive plaques were strongly hybridizing to the probe in question but, in addition, there was an amount of plaques hybridizing more weakly to the probes. This again suggested that there would be other laccase genes in the genomes, having cross-reaction to the probes used. From two to eight strongly hybridizing plaques were purified from each screening. The phage DNAs were isolated and characterized by Southern blot hybridizations. The chosen restriction fragments hybridizing to the probe were subcloned to pBluescript II KS+ or SK+ vectors and the relevant regions of the clones were sequenced.

A total of four laccase genes were cloned from *Thielavia arenaria* ALKO 4197 and three from *Chaetomium thermophilum* ALKO 4265. The Table 7 summarizes the information on the probes used for screening the genes, the phage clones from which the genes were isolated, the chosen restriction fragments containing the full-length genes with their promoter and terminator regions, the plasmid names, and the DSM deposit numbers for the *E. coli* strains carrying these plasmids.

The sequences of the laccase genes are shown in FIG. 6. The relevant information on the genes and the deduced protein sequences are summarized in Table 8 and Table 9, respectively.

The peptide sequences of the purified TaLcc1 and CtLcc1 (Tables 3 and 4) were found from the deduced amino acid sequences of the clones containing the Talcc1 and Ctlcc1 genes (some inaccuracies were found from the peptide sequences after the deduced amino acid sequences were available). Thus, it could be concluded that the genes encoding the purified laccase proteins TaLcc1 and CtLcc1 were cloned. The synthesis of PCR fragments from the Talec1 gene was successful when the PCR primers were designed according to the TaLcc1 peptide sequences (POX28+POX31 and POX27+POX31). However, due to the inaccuracies in the peptide sequencing, the cloning of Ctlcc1 succeeded only when the primers deriving from the homologous fungal laccase sequences were used. The *Thielavia* laccase gene Talcc4 was obtained by using the *N. crassa* probe in the screening of the genomic library. No additional laccase genes were found from the plaques picked and purified from the *Chaetomium* library probed with the *N. crassa* laccase fragment.

TABLE 8

Summary on the laccase genes isolated from *Thielavia arenaria* ALKO4197 and *Chaetomium thermophilum* ALKO4265.

| Laccase gene | Length with introns (bp)[a] | Coding region (bp)[b] | No of introns | Lenths of introns (bp) |
|---|---|---|---|---|
| Talcc1 | 2279 | 1851 | 6 | 51, 62, 91, 83, 79, 59 |
| Talcc2 | 1957[d] | 1767 | 2 | 80, 107 |
| Talcc3 | 2015 | 1833 | 3 | 65, 54, 60 |

TABLE 7

The probes used for cloning of laccase gene, the phage clone and the subclones chosen, the plasmid number and the number of the deposit of the corresponding *E. coli* strain.

| Gene | Probe used in screening | Phage clone | The fragment subcloned to pBluescript II | Plasmid no | *E. coli* deposit no |
|---|---|---|---|---|---|
| Talcc1 | pALK1550 | F1 | 3.8 kb SpeI | pALK1342 | DSM 15484 |
| Talcc2 | pALK1601 | F9 | 4.2 kb XbaI - SpeI | pALK1347 | DSM 15486 |
| Talcc3 | pALK1624 | F1 | 4.3 kb SmaI | pALK1345 | DSM 15485 |
| Talcc4 | *N. crassa* PCR probe | F14 | 5.0 kb BglII | pALK1664 | DSM 15487 |
| Ctlcc1 | pALK1299 | F6/4 | 3.7 kb XhoI | pALK1304 | DSM 15075 |
| Ctlcc2 | pALK1295 | F2/5 | 4.2 kb XbaI | pALK1305 | DSM 15076 |
| Ctlcc3 | pALK1296 | F3/7 | 3.5 kb SacII - SalI | pALK1685 | DSM 16040 |

TABLE 8-continued

Summary on the laccase genes isolated from *Thielavia arenaria* ALKO4197 and *Chaetomium thermophilum* ALKO4265.

| Laccase gene | Length with introns (bp)[a] | Coding region (bp)[b] | No of introns | Lenths of introns (bp) |
|---|---|---|---|---|
| Talcc4 | 1793 | 1719 | 1 | 71 |
| Ctlcc1 | 2127 | 1821 | 5 | 50, 53, 50, 55, 95 |
| Ctlcc2 | 1986 | 1797 | 3 | 49, 61, 79 |
| Ctlcc3 | 2064[c] | 1869 | 3 | 58, 65, 69 |

[a]The STOP codon is included.
[b]The STOP codon is not included.
[c]The other translation start site in Ctlcc3, deleting the first intron, would result in a gene length of 1958 bp and a coding region of 1821 bp (FIG. 6).
[d]The other translation start site in Talcc2 would result in a gene length of 1927 bp and a coding region of 1737 bp (FIG. 6).

TABLE 9

Summary of the deduced laccase sequences from *Thielavia arenaria* ALKO4197 and *Chaetomium thermophilum* ALKO4265. ss, signal sequence.

| Laccase protein | No of aas | Length of ss NN/HMM[a] | C-term. tail[b] | Predicted MW (Da, ss not incl)[c] | Predicted pI (ss not incl) | Putative N-glycosylation sites[d] |
|---|---|---|---|---|---|---|
| Talcc1 | 617 | 21/21 | DSGL + 13 aas | 64 456 | 6.31 | 9 |
| Talcc2[e] | 589 | 29/24 | DSGI | 61 811/62 274 | 4.65/4.65 | 12 |
| Talcc3 | 611 | 25/23 | DSGL + 18 aas | 62 703/62 893 | 6.27/6.27 | 8 |
| Talcc4 | 573 | 18/18 | DSGV | 61 072 | 4.31 | 9 |
| Ctlcc1 | 607 | 20/20 | DSGL + 13 aas | 63 905 | 6.09 | 8 |
| Ctlcc2 | 598 | 22/22 | DSGL | 64 162 | 6.15 | 9 |
| Ctlcc3[f] | 623 | No ss found | DSGT | 69 536 | 5.28 | 8 |

[a]The prediction on the signal sequence was made using the program SignalP V2.0 (Nielsen at al., 1997; Nielsen and Krogh, 1998); the NN value was obtained using neural networks and HMM value using hidden Markov models.
[b]The "concensus" amino acid sequence (DSGX) at the C-terminal end and the number of amino acids after the concensus sequence.
[c]The predicted signal sequence and the C-terminal tail were not included. The prediction was made using the Compute pI/MW tool at ExPASy server (Gasteiger et al., 2003). The two values marked for TaLcc2 and TaLcc3 are calculated after deleting the two possible signal sequences.
[d]The number of sequences N-X-S/T.
[e]There are two possible translation start sites for the Talcc2 gene. The predicted signal peptides and other values were obtained using the longer sequence. The predicted signal sequence would be 17 amino acids for the polypeptide encoded by the shorter gene (the deduced sequence 579 amino acids).
[f]There are two possible translation start sites for the Ctlcc3 gene. The deduced amino acid sequence for the shorter polypeptide is 607 amino acids, MW 62 029 Da and pI 4,65. No predicted signal sequence was detected from either of the deduced amino acid sequences.

The deduced amino acid sequences of TaLcc1 and CtLcc1 were found to be the most homologous to each other, as were also the TaLcc3 and CtLcc2 (also at the gene level, e.g. in the organization of introns of the respective genes). The identity value obtained for TaLcc1 and CtLcc1 using Needleman-Wunsch global alignment (EMBLOSUM62, Gap penalty 10.0, Extend penalty 0.5; European Molecular Biology Open Software Suite program package, version 2.9.0) was 69.5% and that for TaLcc3 and CtLcc2 was 67.3% (Table 10). The identity values of the other laccase proteins were lower, when aligned with each other and with TaLcc1, CtLcc1, TaLcc3 and CtLcc2 (Table 10).

TABLE 10

The identity values (%) obtained from alignment of the deduced amino acid sequences of the *Thielavia* ALKO4197 and *Chaetomium* ALKO4265 laccases (Needleman-Wunsch global alignment, EMBLOSUM62, Gap penalty 10.0, Extend penalty 0.5).

| Laccase | Ta Lcc1 | Ct Lcc1 | Ta Lcc3 | Ct Lcc2 | Ta Lcc4 | Ta Lcc2[a] | Ct Lcc3[a] |
|---|---|---|---|---|---|---|---|
| Ta Lcc1 | 100.0 | 69.5 | 47.8 | 47.1 | 34.7 | 34.4 | 28.8 |
| Ct Lcc1 | | 100.0 | 47.8 | 47.0 | 36.1 | 33.8 | 31.2 |
| Ta Lcc3 | | | 100.0 | 67.3 | 35.6 | 37.5 | 28.4 |
| Ct Lcc2 | | | | 100.0 | 36.5 | 35.0 | 29.6 |
| Ta Lcc4 | | | | | 100.0 | 42.4 | 31.2 |
| Ta Lcc2 | | | | | | 100.0 | 32.9 |
| Ct Lcc3 | | | | | | | 100.0 |

[a]= The deduced TaLcc2 and CtLcc3 amino acid sequences starting from the first Met of the putative sequences (FIG. 6) were used in the alignments.

The highest homologies of the deduced TaLcc1 and CtLcc1 sequences (BLAST program, version 2.2.9 at NCBI, National Center for Biotechnology Information; Altschul et al., 1990) were to the laccases from *Melanocarpus albomyces, Podospora anserina* and *Neurospora crassa* (EMBL accession numbers CAE00180, LAC2_PODAN, LAC1_NEUCR/XP_323881/KSNCLO). The highest identities of TaLcc1 and CtLcc1 to the laccases in the patent database were to laccases from *Myceliophthora thermophila* (EP 0765394 B1) and *Scytalidium thermophilum* (U.S. Pat. No. 5,750,388). The other deduced laccase sequences did not have as high identities to the previously published sequences. The highest identities of TaLcc3 and CtLcc2 were to *Magnaporthe grisea* hypothetical protein (EAA57158.1) and to *Collecotrichum lagenarium* laccase (BAB32575). The highest homologies of the other laccases to the previously published sequences were as follows: TaLcc2 to *N. crassa* hypothetical protein (XP_330977), TaLcc4 to *Gibberella zeae* hypothetical protein (EAA68613), CtLcc3 to *N. crassa* and *Magnaporthe grisea* hypothetical proteins (XP_324706 and EAA47633). Thus, also other fungal species have similar sequences but these sequences have not yet been identified as laccases. The sequences found from the databases, having at least 50% identity to the deduced amino acid sequences of the laccases from *Thielavia* ALKO 4197 and *Chaetomium* ALKO 4265, are shown in Table 11.

TABLE 11

The sequences with at least 50% identity (%) to the deduced amino acid sequences of *Thielavia* ALKO4197 and *Chaetomium* ALKO4265 laccases. The alignment was made using Needleman-Wunsch global alignment (EMBLOSUM62, Gap penalty 10.0, Extend penalty 0.5).

| The amino acid sequence | Identity (%) |
|---|---|
| TaLcc1 | 100.0 |
| *Melanocarpus albomyces* CAE001810 | 73.1 |
| *Myceliophthora thermophila* | 68.3 |
| *Podospora anserina* LAC2_PODAN | 66.7 |
| *Scytalidium thermophilum* | 62.6 |
| *Neurospora crassa* LAC1_NEUCR | 60.7 |
| *Neurospora crassa* XP_323881 | 60.7 |
| *Neurospora crassa* KSNCLO | 60.6 |
| *Neurospora crassa* LAC2_NEUCR | 60.4 |
| *Cryphonectria parasitica* LAC1_CRYPA | 57.5 |
| *Gaeumannomyces graminis* var tritici Lac3 CAD10749 | 51.0 |
| TaLcc2 | 100.0 |
| *Neurospora crassa* XP_330977 | 59.3 |
| *Botryotinia fuckeliana* laccase 2 AAK77953 | 56.4 |
| *Gaeumannomyces graminis* var tritici Lac1 CAD10747 | 53.0 |
| *Gaeumannomyces graminis* var graminis CAD24841 | 52.6 |
| *Botryotinia fuckeliana* laccase 1 AAK77952 | 50.2 |
| TaLcc3 | 100.0 |
| *Magnaporthe grisea* EAA57158 | 57.4 |
| *Colletotrichum lagenarium* BAB32575 | 53.4 |
| TaLcc4 | 100.0 |
| *Gibberella zeae* EAA68613 | 77.4 |
| *Gibberella zeae* XP_390780 | 77.4 |
| *Magnaporthe grisea* EAA52662 | 60.1 |
| *Gaeumannomyces graminis* var tritici Lac2 CAD10748 | 54.8 |
| *Magnaporthe grisea* EAA48009 | 53.6 |
| *Gibberella zeae* XP_389822 | 50.2 |
| CtLcc1 | 100.0 |
| *Melanocarpus albomyces* CAE001810 | 73.2 |
| *Podospora anserina* LAC2_PODAN | 68.4 |
| *Myceliophthora thermophila* | 67.6 |
| *Scytalidium thermophilum* | 66.5 |
| *Neurospora crassa* XP_323881 | 62.7 |
| *Neurospora crassa* KSNCLO | 62.6 |
| *Neurospora crassa* LAC2_NEUCR | 62.4 |
| *Neurospora crassa* LAC1_NEUCR | 62.1 |
| *Cryphonectria parasitica* LAC1_CRYPA | 58.1 |
| CtLcc2 | 100.0 |

TABLE 11-continued

The sequences with at least 50% identity (%) to the deduced amino acid sequences of *Thielavia* ALKO4197 and *Chaetomium* ALKO4265 laccases. The alignment was made using Needleman-Wunsch global alignment (EMBLOSUM62, Gap penalty 10.0, Extend penalty 0.5).

| The amino acid sequence | Identity (%) |
|---|---|
| *Magnaporthe grisea* EAA57158 | 54.5 |
| *Colletotrichum lagenarium* BAB32575 | 53.4 |
| CtLcc3 | 100.0 |
| *Neurospora crassa* XP_324706 | 52.7 |
| *Magnaporthe grisea* EAA47633 | 52.3 |

EXAMPLE 4

Production of recombinant Laccases in *Trichoderma reesei*

Expression plasmids were constructed for production of the recombinant TaLcc1, TaLcc2, TaLcc3, TaLcc4, CtLcc1 and CtLcc2 proteins. The expression cassette was not constructed for production of CtLcc3 due to lack of a predicted signal sequence in the deduced amino acid sequence. The expression plasmids constructed are listed in Table 12. The laccase genes, including their own signal sequences, were exactly fused to the *T. reesei* cbh1 (cel7A) promoter by PCR. The cbh1 promoter, cbh1 terminator, amdS marker and the cbh1 3' flanking region included were as described in Paloheimo et al. (2003). The linear expression cassettes (FIG. 7), were isolated from the vector backbones and were transformed to *T. reesei* A47 protoplasts. The transformations were performed as in Penttila et al. (1987) with the modifications described in Karhunen et al. (1993). The transformants were purified on selection plates through single conidia prior to sporulating them on PD.

TABLE 12

The expression cassettes constructed to produce *Chaetomium thermophilum* ALKO4265 and *Thielavia arenaria* ALKO4197 laccases in *Trichoderma reesei*. The overall structure of the expression cassettes was as described in FIG. 7. The laccase genes were exactly fused to the cbh1 promoter except in pALK1326 and pALK1327 where the Ctlcc1 gene is fused to a carrier polypeptide (Cel6A CBD A + B or A + B + B') and a synthetic Kex2 linker (including the amino acids RDKR). Analogous constructs to these two plasmids, pALK1285 and pALK1286, are described in Paloheimo at al. (2003).

| Laccase gene | Expression plasmid | Size of the expr. cassette[a] | Laccase terminator[b] | Carrier |
|---|---|---|---|---|
| Ct lcc1 | pALK1321 | 10.1 kb | 205 bp (EcoRV) | No carrier |
| Ct lcc1 | pALK1326 | 10.3 kb | 205 bp (EcoRV) | Cel6A CBD (A + B) |
| Ct lcc1 | pALK1327 | 10.4 kb | 205 bp (EcoRV) | Cel6A CBD (A + B + B') |
| Ct lcc2 | pALK1340 | 9.8 kb | 92 bp (BamHI) | No carrier |
| Ct lcc3 | Not done | | | |
| Ta lcc1 | pALK1667 | 10.1 kb | 80 bp (NcoI) | No carrier |
| Ta lcc2 | pALK1655[c] | 9.9 kb | 168 bp (XhoI) | No carrier |
| Ta lcc2 | pALK1656[d] | 9.9 kb | 168 bp (XhoI) | No carrier |
| Ta lcc3 | pALK1671 | 10.0 kb | 232 bp (MscI) | No carrier |
| Ta lcc4 | pALK1684 | 10.0 kb | 481 bp (EcoRV) | No carrier |

[a]The expression cassette for *T. reesei* transformation was isolated from the vector backbone by using EcoRI digestion, except in the case of pALK1671 where NotI was used.

TABLE 12-continued

The expression cassettes constructed to produce *Chaetomium thermophilum* ALKO4265 and *Thielavia arenaria* ALKO4197 laccases in *Trichoderma reesei*. The overall structure of the expression cassettes was as described in FIG. 7. The laccase genes were exactly fused to the cbh1 promoter except in pALK1326 and pALK1327 where the Ctlcc1 gene is fused to a carrier polypeptide (Cel6A CBD A + B or A + B + B') and a synthetic Kex2 linker (including the amino acids RDKR). Analogous constructs to these two plasmids, pALK1285 and pALK1286, are described in Paloheimo at al. (2003).

| Laccase gene | Expression plasmid | Size of the expr. cassette[a] | Laccase terminator[b] | Carrier |
|---|---|---|---|---|

[b]The number of the nucleotides from the genomic laccase terminator region after the STOP codon. The restriction site used in excising the genomic gene fragment from the 3'-end is included in the parenthesis.
[c]The Ta lcc2 gene from the first putative translation start site was used (the length of the gene 1957 bp, including the introns and the STOP codon; FIG. 6 and Table 8).
[d]The Ta lcc2 gene from the second putative translation start site was used (the length of the gene 1927 bp, including the introns and the STOP codon; FIG. 6 and Table 8).

The laccase production of the transformants was analysed from the culture supernatants of the shake flask cultivations (50 ml). The transformants were grown for 7 days in a complex lactose-based cellulase-inducing medium (Joutsjoki et al. 1993) buffered with 5% $KH_2PO_4$ and supplemented with 0.1 mM $CuSO_4$ at pH 6.0. The laccase activity was assayed using ABTS as a substrate as described in Example 1. Laccase activity was obtained from all the constructs. The possible targeting of the expression cassette to the cbh1 (cel7A) locus was screened as a CBHI-negative phenotype by dot blot (Minifold I-SRC 96 dot blotter, Schleicher & Schuell, Dassel, Germany) or by Western blot. The detection of the CBHI protein was performed using the monoclonal antibodies CI-258 or CI-261 (Aho et al., 1991) and the ProtoBlot Western blot AP system (Promega). The genotypes of the chosen transformants were confirmed by using Southern blots in which several genomic digests were included and the respective expression cassette was used as a probe.

The chosen CBHI-negative transformants were cultivated in fermentors to obtain material for purification of the recombinant proteins (Example 5) and for the application tests (Examples 7-10).

EXAMPLE 5

Purification of the Recombinant *Thielavia* and *Chaetomium* Laccases

The heterologously produced *Thielavia arenaria* and *Chaetomium thermophilum* laccases were purified from the culture filtrates with common chromatographic means. The buffer of the culture filtrate was changed to the appropriate equilibrating buffer prior to the chromatographic step with gel filtration using Sephadex G25 resin (Pharmacia). The purification procedures for each laccase are summarized in Table 13.

TABLE 13

Purification of the heterologously produced *Thielavia arenaria* and *Chaetomium thermophilum* laccases.

| Laccase | Chromatographic method/Resin | Equilibration buffer | Elution protocol |
|---|---|---|---|
| CtLcc1 | Anionexchange/DEAE Sepharose FF | 20 mM Tris HCl, pH 8.0 | with a linear gradient of 0-250 mM $Na_2SO_4$ in EB |
| | HIC/Phenyl Sepharose FF | 20 mM Tris HCl pH 7.0, containing 500 mM, $Na_2SO_4$ | with a linear gradient of 200-0 mM $Na_2SO_4$ in EB |
| | Anionexchange/Resource Q | 10 mM imidazole, pH 7.3 | with a linear gradient of 0-150 mM $Na_2SO_4$ in EB |
| TaLcc1 | Anionexchange/DEAE Sepharose FF | 5 mM Tris HCl, pH 8.5 | with a linear gradient of 0-350 mM $Na_2SO_4$ in EB |
| | Anionexchange/Resource Q | 5 mM Tris HCl, pH 8.5 | with a linear gradient of 0-200 mM $Na_2SO_4$ in EB |
| | Gel Filtration/Sephacryl S-100 HR | 100 mM Tris HCl, pH 7.3, 150 mM NaCl | — |
| TaLcc2 | Anionexchange/DEAE Sepharose FF | 10 mM Tris HCl, pH 8.5 | with a linear gradient of 0-300 mM $Na_2SO_4$ in EB |
| | HIC/Phenyl Sepharose FF | 20 mM citrate, pH 7.0, containing 500 mM, $Na_2SO_4$ | with a linear gradient of 500-0 mM $Na_2SO_4$ in EB |
| | Anionexchange/Resource Q | 10 mM imidazole, pH 7.3 | with a linear gradient of 0-150 mM $Na_2SO_4$ in EB |
| | Gel Filtration/Sephacryl S-100 HR | 100 mM Tris HCl pH 7.0, 150 mM NaCl | — |
| TaLcc3 | Cationexcahnge/CM Sepharose FF | 20 mM acetate, pH 5.0 | with a linear gradient of 0-100 mM $Na_2SO_4$ in EB |
| | HIC/Phenyl Sepharose FF | 20 mM citrate, pH 6.0, containing 700 mM, $Na_2SO_4$ | with a linear gradient of 700-0 mM $Na_2SO_4$ in EB |
| | Cationexcahnge/Resource S | 10 mM acetate pH 5.0 | with a linear gradient of 0-200 mM $Na_2SO_4$ in EB |

TABLE 13-continued

Purification of the heterologously produced *Thielavia arenaria* and *Chaetomium thermophilum* laccases.

| Laccase | Chromatographic method/Resin | Equilibration buffer | Elution protocol |
|---|---|---|---|
| TaLcc4 | Anionexchange/DEAE Sepharose FF | 20 mM acetate pH 5.5 | with a linear gradient of 120-400 mM $Na_2SO_4$ in EB |
|  | HIC/Phenyl Sepharose FF | 20 mM citrate, pH 6.0, containing 1500 mM, | with a linear gradient of 1500-900 mM |

HIC hydrophobic interaction chromatography,
EB equilibrium buffer.

EXAMPLE 6

Characterization of the *Thielavia* and *Chaetomium* Laccases

The purified recombinant *Thielavia* and *Chaetomium* laccases were characterized in terms of pH optimum, thermal stability, and pI as described in Example 2. The molecular weight was determined by MALDI-TOF mass spectrometry on a Ultraflex™ time-of-flight instrument (BrukerDaltonics, Germany) as previously described (Palonen et al., 2003). The redox-potentials of the T1 coppers of for CtLcc, and TaLcc2 laccases were determined by photometric copper titration in 0.1 M $KH_2PO_4$ (pH 6.0) as described by Xu et al. (1996) using the redox titrant couple $K_3Fe(CN)_6/K_4Fe(CN)_6$. The redox potential of TaLcc1 was determined with a combined Pt—AgCl/KCl microelectrode at pH 5.0 according to Sigoillot et al (2004). The characterization results are collected to Table 14.

The inhibition effect of different compounds on the activity of the laccases was determined as described in Example 2. except with Talcc4, with which the inhibition was analyzed using spectroscopic activity assay. Instead of following oxygen consumption in the ABTS reaction, the enzyme activity was determined spectrofotometrically. Because the activity of TaLcc3 was very low with all tested substrates the inhibition experiments with this enzyme were not carried out. Results are shown in Table 15.

TABLE 15

Inhibition of the recombinant *Thielavia* and *Chaetomium* laccases by various compounds. Inhibition tested by spectrofotometric ABTS assay with TaLcc4, the inhibition of the other laccases determined by oxygen consumption measurements.

| Compound | Concentr. (mM) | Inhibition (%) | | | |
|---|---|---|---|---|---|
| | | CtLcc1 | TaLcc1 | TaLcc2 | TaLcc4 |
| EDTA | 10 | 0 | 5 | 0 | 2 |
| NaN3 | 0.5 | 100 | 95 | 95 | 95 |
| KCN | 0.1 | 70 | 60 | 30 | 44 |
|  | 1 | 100 | 90 | 70 | 90 |
| NaCl | 0.1 | 0 | 0 | 20 | 5 |
|  | 1 | 10 | 0 | 30 | 20 |

TABLE 14

Summary of the characteristics of the recombinant *Thielavia* and *Chaetomium* laccases.

| Laccase | pH optimum on guaiacol or DMP | T½ (60° C.) (hrs) | PI | Number of pI isoforms | MW (MALFI-TOF) | $E^0$ mV |
|---|---|---|---|---|---|---|
| CtLcc1 | 5.0 guaiacol | 7 | 4.0-4.3 | 3-4 | 71 670 | 480 |
| TaLcc1 | 6.0 guaiacol | 5 | 5.5-6.9 | 6-7 | 71 890 | 560 |
| TaLcc2 | 5.5 guaiacol | 0.5 | 3.5 | 1 | 75 618 | 450 |
| TaLcc3 | 5.0 guaiacol | 3.5 | 7.0-8.0 | 2 | 70 050 | nd |
| TaLcc4 | 6.0 DMP | <5 min | 3.0 | 1 | nd | nd | nd = not determined.

Specific activities of the purified *Thielavia* and *Chaetomium* laccases were determined towards ABTS, dimetoxy phenol (DMP), syringaldazine, and guaiacol as described in Example 2. The ABTS activity measurements were carried out in 25 mM succinate buffer pH 4.5 at 25° C., and the other activities in 25 mM MES buffer, pH 5.5. The results are shown in Table 16.

TABLE 16

Specific activities of the *Thielavia* and *Chaetomium* laccases compared to the specific activities of a well-known fungal laccase from *Melanocarpus albomyces*. MaL *Melanocarpus albomyces* laccase.

| Substrate | MaL nkat/mg | CtLcc1 nkat/mg | TaLcc1 nkat/mg | TaLcc2 nkat/mg | TaLcc3 nkat/mg | TaLcc4 nkat/mg |
|---|---|---|---|---|---|---|
| ABTS | 840 | 705 | 910 | 360 | 8.3 | 1000 |
| DMP | 290 | 290 | 285 | 75 | 2.1 | 110 |
| Syringald | 380 | 400 | 340 | 120 | 3.6 | 52 |
| Guaiacol | 90 | 85 | 61 | 40 | 0 | 5 |

Kinetic Parameters of the *Thielavia* and *Chaetomium* Laccases

The kinetic parameters, Michaelis-Menthen constant $K_m$, turn-over number $k_{cat}$ and the specificity constant ($k_{cat}/K_m$) were determined on ABTS and 2,6-dimethoxy phenol (DMP), and syringaldazin. The measurements on ABTS were done in 25 mM succinate buffer, pH 4.5. On syringaldazin and DMP 40 mM MES buffer, pH 6 was used. All activity assays were carried out at 25° C. Kinetic parameters were estimated by a nonlinear regression curve fit. The results are shown in Table 4. The values were compared to those of *Melanocarpus albomyces* MaL, laccase.

TABLE 17

Kinetic parameters of the *Thielavia* and *Chaetomium* laccases determined on ABTS, syringaldazin, and DMP, and compared to the values of MaL.

|  | CtLcc1 | TaLcc1 | TaLcc2 | TaLcc3 | TaLcc4 | MaL |
|---|---|---|---|---|---|---|
| ABTS | | | | | | |
| $K_m$ (μM) | 330 | 75 | 30 | 1040 | 2470 | 270 |
| $k_{cat}$ (min$^{-1}$) | 4480 | 4130 | 640 | 37 | 8610 | 4690 |
| $k_{cat}/K_m$ (M$^{-1}$min$^{-1}$) | $1.36 * 10^8$ | $5.51 * 10^7$ | $3.52 * 10^7$ | $3.48 * 10^4$ | $3.48 * 10^6$ | $1.8 * 10^7$ |
| DMP | | | | | | |
| $K_m$ (μM) | 4.6 | 17 | 30 | 14 | 1900 | 5 |
| $k_{cat}$ (min$^{-1}$) | 2500 | 4030 | 520 | 5 | 1590 | 4160 |
| $k_{cat}/K_m$ (M$^{-1}$min$^{-1}$) | $5.42 * 10^8$ | $2.37 * 10^8$ | $1.72 * 10^7$ | $3.57 * 10^5$ | $8.37 * 10^6$ | $8.1 * 10^8$ |
| Syringaldazin | | | | | | |
| $K_m$ (μM) | 2.4 | 4.3 | 6.3 | 4.3 | 115 | 1.3 |
| $k_{cat}$ (min$^{-1}$) | 2490 | 1940 | 450 | 12 | 930 | 4710 |
| $k_{cat}/K_m$ (M$^{-1}$min$^{-1}$) | $1.04 * 10^9$ | $4.51 * 10^8$ | $7.12 * 10^7$ | $2.79 * 10^6$ | $7.96 * 10^6$ | $3.6 * 10^9$ |

The biochemical data presented here clearly indicates that the recombinant CtLcc1 is the same protein as the wild type *Chaetomium* laccase purified from the culture supernatant and the recombinant TaLcc1 is the same protein as the wild type *Thielavia* laccase purified from the culture supernatant.

EXAMPLE 7

Performance of Laccase Preparations in Denim Bleaching at Different pH Values

The recombinant laccase preparations produced using *Trichoderma* as a host were used in all the application tests, in Examples 7-10. The recombinant laccases CtLcc1, TaLcc2 and TaLcc4, derived from strains RF5469, RF5573 and RF5687, respectively, were tested for their ability to bleach denim. The commercial laccase preparation DeniLite II Base from Novozymes was used as comparison.

Lee Cooper jeans (MASI Company Oy, Finland) that were desized and treated with neutral ECOSTONE® cellulase were used as test material. Laccase treatments were performed in LP-2 Launder Ometer as follows. About 10 g of denim swatches (15×14 cm) were loaded into 1.2 liter containers containing 200 ml Mc Ilvaine's citrate phosphate buffer pH 5, 6 or 7 and the containers were temperated. Enzyme with or without the mediator (methyl syringate, DeniLite II Assist, Novozymes) was added as laccase activity units. Enzyme was dosed 200 nkat/g and the mediator 10 mg/g on the weight of fabric. Enzyme activity was measured with ABTS substrate (Example 1) but using citrate phosphate buffer in all examples 7-10. The Launder Ometer was run at 50° C. for 30 min and after that the temperature in Launder was raised to 80° C. for 10 min. The swatches were carefully rinsed with warm water, dried half-dry in a tumbler and after that air dried.

The bleaching effect was evaluated by measuring the colour as reflectance values with the Minolta Chromameter CM 1000 (Minolta Co.) using L*a*b* color space coordinates (illuminant D65). The colour from both sides of the swatches was measured before and after the laccase treatment. Each measurement was the average of several measurements.

Table 18 and FIG. 8 show that both CtLcc1 and TaLcc2 laccases were more efficient in decolorization of indigo dye of denim compared to DeniLite II Base at pH values 6 and 7. At pH 6 the look of the denim fabric was distinctly much lighter with these two laccases than with DeniLite also by visual evaluation. Without the mediator the laccases did not have notable effect on denim (Table 19).

TABLE 18

Colour measurements of the face side of denim treated with laccase preparations and the mediator in Launder at pH 5-7.

| Prep. | Enzyme nkat/g | Mediator mg/g | Conditions | Before laccase treatment L* | b* | After laccase treatment L* | b* | Increase of L* |
|---|---|---|---|---|---|---|---|---|
| CtLcc1 | 200 | 10 | 30 min, 50° C., pH 5 | 29.16 | −18.45 | 35.07 | −18.38 | 5.91 |
| TaLcc2 | 200 | 10 | 30 min, 50° C., pH 5 | 28.29 | −18.47 | 33.68 | −17.91 | 5.39 |
| TaLcc4 | 200 | 10 | 30 min, 50° C., pH 5 | 28.16 | −18.70 | 29.17 | −18.47 | 1.01 |
| DeniLite | 200 | 10 | 30 min, 50° C., pH 5 | 28.41 | −18.70 | 35.70 | −17.59 | 7.29 |
| CtLcc1 | 200 | 10 | 30 min, 50° C., pH 6 | 28.89 | −18.66 | 40.08 | −17.18 | 11.19 |
| TaLcc2 | 200 | 10 | 30 min, 50° C., pH 6 | 28.44 | −18.52 | 39.01 | −17.46 | 10.57 |
| TaLcc4 | 200 | 10 | 30 min, 50° C., pH 6 | 28.20 | −18.47 | 29.55 | −18.11 | 1.35 |
| Denilite | 200 | 10 | 30 min, 50° C., pH 6 | 26.98 | −18.67 | 34.16 | −17.82 | 7.18 |
| CtLcc1 | 200 | 10 | 30 min, 50° C., pH 7 | 28.38 | −18.94 | 36.69 | −17.88 | 8.31 |
| TaLcc2 | 200 | 10 | 30 min, 50° C., pH 7 | 28.59 | −18.91 | 35.85 | −18.27 | 7.26 |
| TaLcc4 | 200 | 10 | 30 min, 50° C., pH 7 | 27.84 | −18.63 | 28.31 | −18.33 | 0.47 |
| Denilite | 200 | 10 | 30 min, 50° C., pH 7 | 28.67 | −18.99 | 34.51 | −17.75 | 5.84 |

L* indicates lightness,
−b* is the blue direction,
+b* is the yellow direction.

TABLE 19

Colour measurements of the face side of denim treated with laccase preparations without the mediator or mediator alone in Launder at pH 5-7.

| Prep. | Enzyme nkat/g | Mediator mg/g | Conditions | Before laccase treatment L* | b* | After laccase treatment L* | B* | Increase of L* |
|---|---|---|---|---|---|---|---|---|
| CtLcc1 | 200 | 0 | 30 min, 50° C., pH 5 | 28.42 | −18.44 | 28.88 | −18.65 | 0.46 |
| TaLcc2 | 200 | 0 | 30 min, 50° C., pH 5 | 30.13 | −18.62 | 30.11 | −18.63 | −0.02 |
| TaLcc4 | 200 | 0 | 30 min, 50° C., pH 5 | 29.44 | −18.69 | 29.40 | −18.70 | −0.04 |
| DeniLite | 200 | 0 | 30 min, 50° C., pH 5 | 29.18 | −18.55 | 29.30 | −18.34 | 0.12 |
| Mediator | 0 | 10 | 30 min, 50° C., pH 5 | 29.85 | −18.58 | 29.90 | −18.15 | 0.05 |
| CtLcc1 | 200 | 0 | 30 min, 50° C., pH 6 | 28.96 | −18.60 | 28.83 | −18.53 | −0.13 |
| TaLcc2 | 200 | 0 | 30 min, 50° C., pH 6 | 28.87 | −18.71 | 29.17 | −18.51 | 0.30 |
| TaLcc4 | 200 | 0 | 30 min, 50° C., pH 6 | 27.44 | −18.55 | 27.68 | −18.76 | 0.24 |
| DeniLite | 200 | 0 | 30 min, 50° C., pH 6 | 28.55 | −18.48 | 28.77 | −18.52 | 0.22 |
| Mediator | 0 | 10 | 30 min, 50° C., pH 6 | 28.68 | −18.40 | 28.9 | −18.37 | 0.22 |
| CtLcc1 | 200 | 0 | 30 min, 50° C., pH 7 | 28.59 | −18.89 | 29.32 | −18.52 | 0.73 |
| TaLcc2 | 200 | 0 | 30 min, 50° C., pH 7 | 27.47 | −18.82 | 28.24 | −18.30 | 0.77 |
| TaLcc4 | 200 | 0 | 30 min, 50° C., pH 7 | 28.79 | −18.71 | 29.29 | −18.89 | 0.50 |
| Denilite | 200 | 0 | 30 min, 50° C., pH 7 | 27.82 | −18.93 | 29.78 | −18.31 | 1.96 |
| Mediator | 0 | 10 | 30 min, 50° C., pH 7 | 29.00 | −18.94 | 30.06 | −18.46 | 1.06 |

L* indicates lightness,
−b* is the blue direction,
+b* is the yellow direction.

EXAMPLE 8

Performance of Laccase Preparations in Denim Bleaching at Different Temperatures Laccases CtLcc1, TaLcc1 (Example 7) and TaLcc2 (strain RF5573) were tested for their ability to bleach denim at different temperatures compared to commercial laccase preparation DeniLite II Base from Novozymes.

The test system and denim were as in Example 7, except that the conditions during the laccase and mediator treatment in Launder were 30 min, pH 6 and temperature 30-70° C. (DeniLite II Base also at 80° C.) and the enzyme was inactivated by alkaline treatment instead of raising the temperature in Launder as follows. After removing swatches from the containers they were soaked in warm water containing NaOH (pH 11.5) for 10 min and rinsed carefully with warm water. The swatches were dried half-dry in a tumbler and after that air dried. The bleaching effect was evaluated by measuring the colour as reflectance values as in Example 7.

Figure 9:
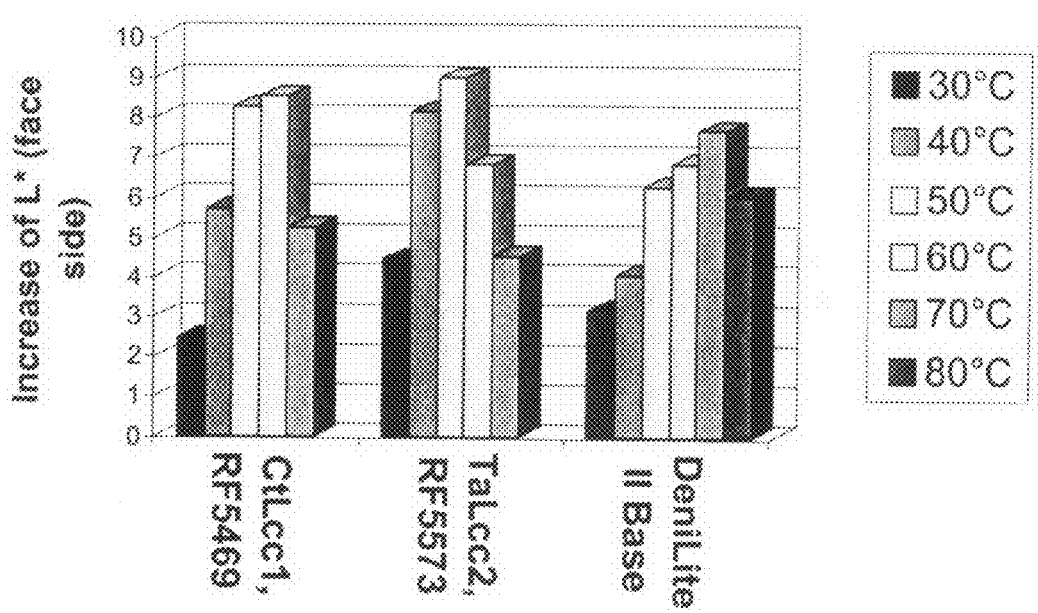
FIG. 9. The performance of laccase preparations in denim bleaching at different temperatures at conditions described in Example 8.
Figure 10A:
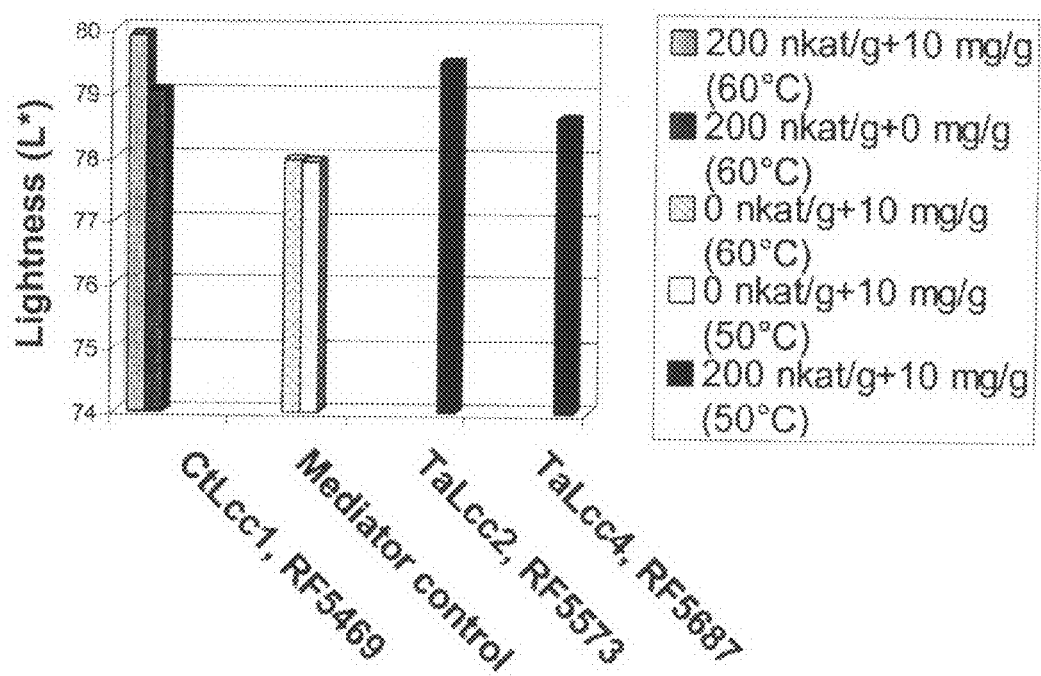
FIGS. 10A and B. Effect of CtLcc1 laccase on grass soiling at 60° C. and TaLcc2 and TaLcc4 laccases at 50° C. at conditions described in Example 9. Mediator control without the enzyme for both temperatures. A. Lightness values, B. a*-values (−a is the green direction, +a is the red direction)
Figure 10B:
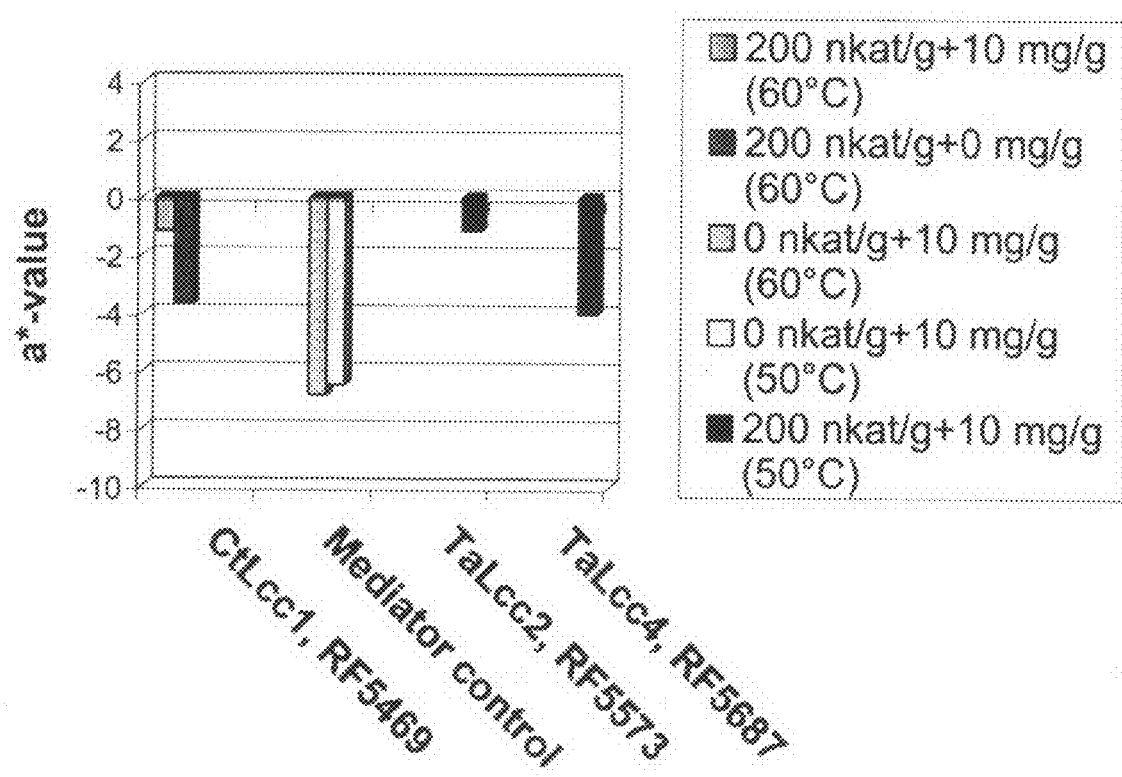

Table 20 and FIG. 9 show that CtLcc1 and especially TaLcc2 laccases were more efficient in decolorization of denim (highest increase of lightness) compared to the commercial laccase Denilite II Base at 40-50° C. and pH 6. TaLcc2 laccase is the most suitable enzyme for applications performed at low temperatures. CtLcc1 and TaLcc2 had also better bleaching effect at their optimal temperatures than DeniLite II base at its optimum

TABLE 20

Colour measurements of the face side of denim treated with laccase preparations and the mediator in Launder at different temperatures.

| Prep. | Enzyme nkat/g | Mediator mg/g | Conditions | Before laccase Treatment L* | b* | After laccase treatment L* | b* | Increase of L* |
|---|---|---|---|---|---|---|---|---|
| CtLcc1 | 200 | 10 | 30 min, 30° C., pH 6 | 29.34 | −18.99 | 31.78 | −19.15 | 2.44 |
| TaLcc2 | 200 | 10 | 30 min. 30° C., pH 6 | 29.54 | −18.77 | 33.99 | −19.33 | 4.45 |
| Denilite | 200 | 10 | 30 min, 30° C., pH 6 | 29.56 | −18.60 | 32.73 | −18.77 | 3.17 |
| CtLcc1 | 200 | 10 | 30 min, 40° C., pH 6 | 28.71 | −18.61 | 34.43 | −18.77 | 5.72 |
| TaLcc2 | 200 | 10 | 30 min, 40° C., pH 6 | 28.93 | −18.48 | 37.08 | −18.53 | 8.15 |
| TaLcc4 | 200 | 10 | 30 min, 40° C., pH 6 | 29.11 | −18.92 | 29.23 | −18.44 | 0.12 |
| DeniLite | 200 | 10 | 30 min, 40° C., pH 6 | 28.87 | −18.90 | 32.94 | −19.14 | 4.07 |
| CtLcc1 | 200 | 10 | 30 min, 50° C., pH 6 | 28.52 | −18.97 | 36.78 | −18.96 | 8.26 |
| TaLcc2 | 200 | 10 | 30 min, 50° C., pH 6 | 28.47 | −19.05 | 37.47 | −18.48 | 9.00 |
| Denilite | 200 | 10 | 30 min, 50° C., pH 6 | 28.41 | −19.10 | 34.67 | −19.07 | 6.26 |
| CtLcc1 | 200 | 10 | 30 min, 60° C., pH 6 | 28.88 | −19.01 | 37.40 | −18.29 | 8.52 |
| TaLcc2 | 200 | 10 | 30 min, 60° C., pH 6 | 29.25 | −18.76 | 36.07 | −18.26 | 6.82 |
| Denilite | 200 | 10 | 30 min, 60° C., pH 6 | 29.06 | −18.99 | 35.92 | −18.33 | 6.86 |
| CtLcc1 | 200 | 10 | 30 min, 70° C., pH 6 | 28.93 | −18.95 | 34.16 | −17.91 | 5.23 |
| TaLcc2 | 200 | 10 | 30 min, 70° C., pH 6 | 28.3 | −19.27 | 32.84 | −17.94 | 4.54 |
| Denilite | 200 | 10 | 30 min, 70° C., pH 6 | 29.05 | −19.15 | 36.72 | −17.35 | 7.67 |
| Denilite | 200 | 10 | 30 min, 80° C., pH 6 | 29.28 | −18.97 | 35.33 | −17.02 | 6.05 |

L* indicates lightness,
−b* is the blue direction,
+b* is the yellow direction.

EXAMPLE 9

Stain Removal with Laccases

Laccases CtLcc1, TaLcc2, TaLcc4 and Denilite II Base (Example 7) were tested for their ability to remove stains. The following artificially soiled test cloths were used: grass soiling (Art.164, EMPA Testmaterialen, Germany), tea soiling (Art. 167, EMPA Testmaterialen, Germany). The fabric was cut in 5.8×5.8 cm swatches. Laccase treatments were performed in LP-2 Launder Ometer as follows. About 5 g of soiled fabrics were loaded into 1.2 liter containers containing 150 ml Mc Ilvaine's citrate phosphate buffer pH 6 and the containers were temperated. Enzyme with or without the mediator (methyl syringate, DeniLite II Assist, Novozymes) was added as laccase activity units (Example 7). Enzyme was dosed 200 nkat/g and the mediator 10 mg/g on the weight of fabric, except at 40° C. dosages of 20 nkat/g and 2 mg/g were also used. The Launder Ometer was run at 40, 50 or 60° C. and pH 6 for 60 min. After that the swatches were carefully rinsed under running water and in shake flasks containing warm water and dried in the air.

The stain removal effect was evaluated by measuring the colour as reflectance values using L*a*b* color space coordinates (Example 7). The colour of the swatches was measured before and after the laccase treatment.

Figure 11A:
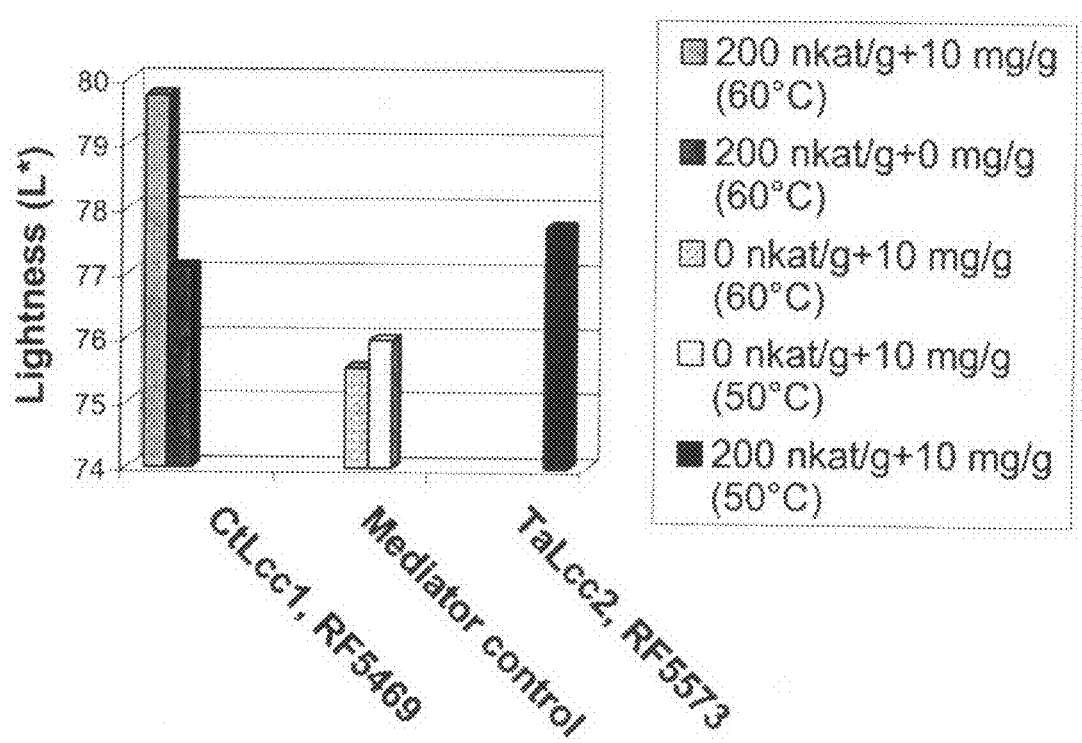
FIGS. 11A and B. Effect of CtLcc1 laccase on tea soiling at 60° C. and TaLcc2 and TaLcc4 laccases at 50° C. at conditions described in Example 9. Mediator control with out the enzyme for both temperatures. A. Lightness values, B. a*-values (−a is the green direction, +a is the red direction)
Figure 11B:
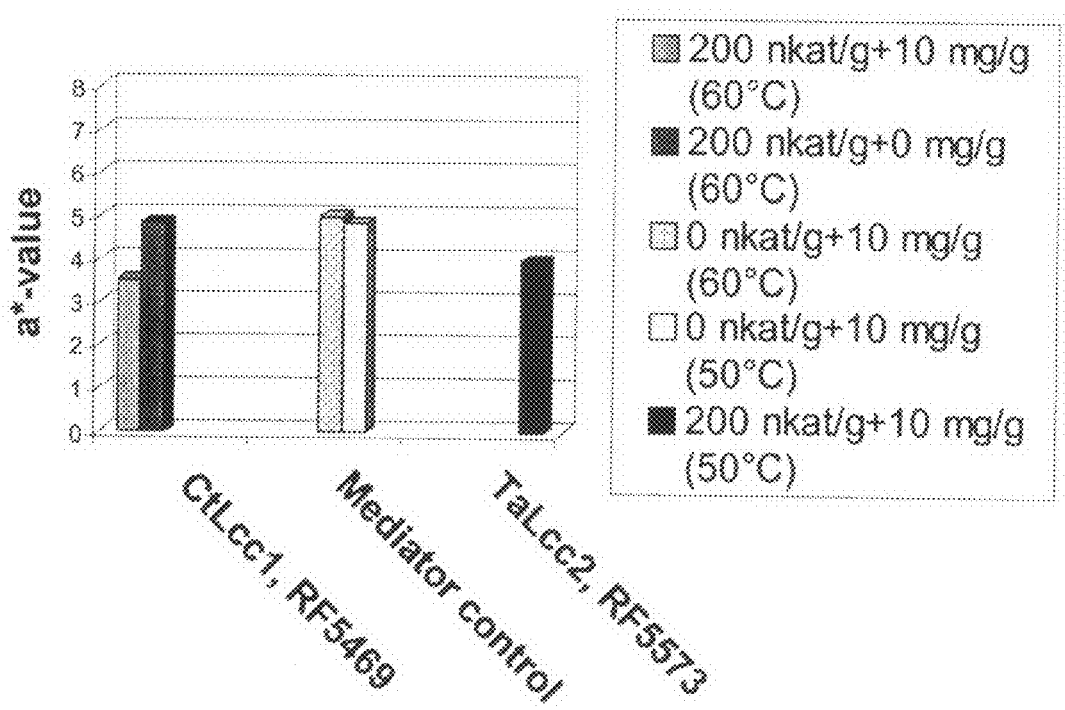
Figure 12A:
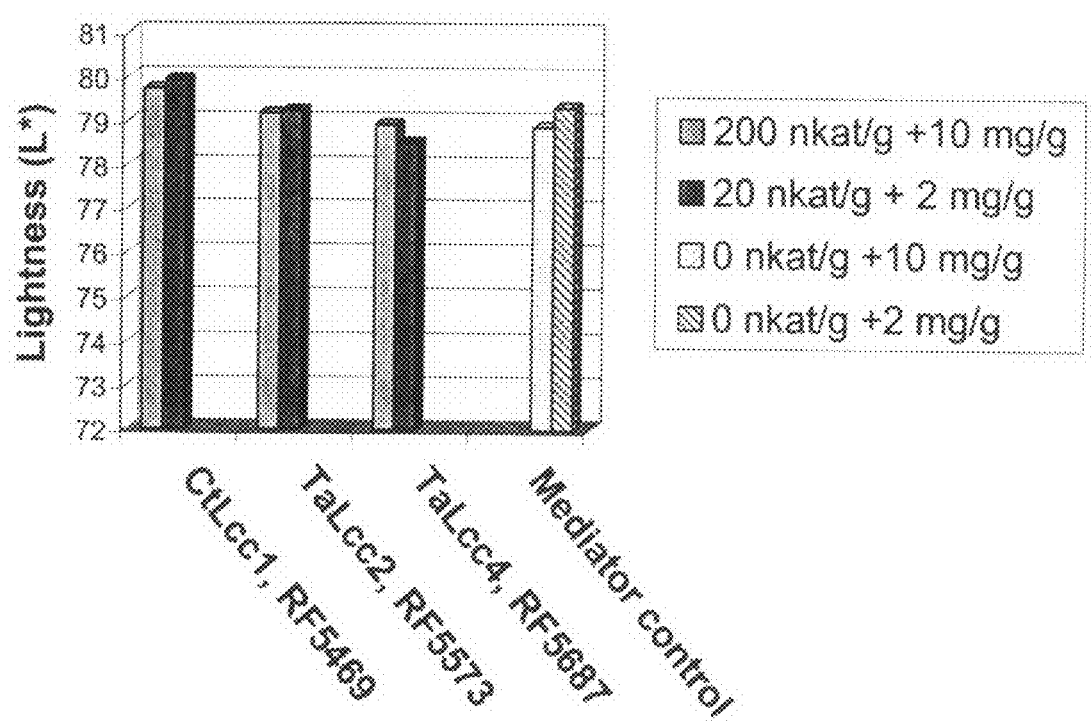
FIGS. 12A and B. Effect of laccase preparations on grass soiling at 40° C. with different dosages at conditions described in Example 10. A. Lightness values, B. a*-values (−a is the green direction, +a is the red direction)
Figure 12B:
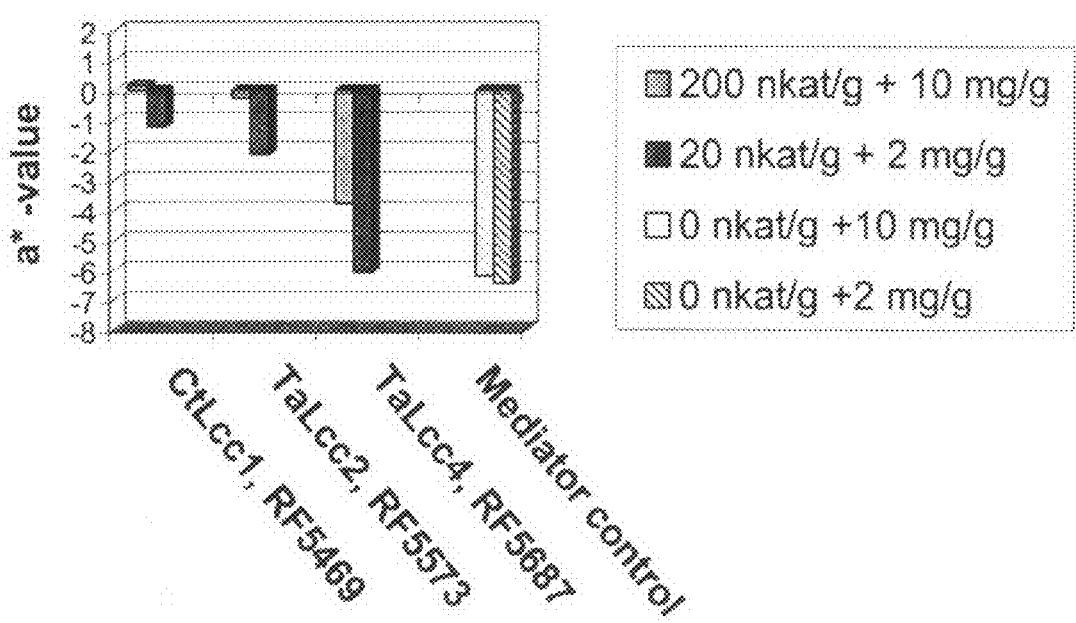

The results of stain removal tests are shown in Tables 21-22 and FIGS. 10-13. CtLcc1 laccase was effective in removal of grass soiling with the mediator at 60° C. and TaLcc2 laccase at 50° C., that can be seen in increased lightness and especially in reduced greenness values in FIG. 10, and also clearly by visual estimation. Similar trend can be seen at 40° C. (FIG. 12). CtLcc1 laccase had some effect without the mediator too, especially at 60° C. TaLcc4 laccase had a slight effect on grass (greenness reduced ca. 2 units) at 50° C. Without the mediator the efficiency in stain removal with laccases was low, especially at 40° C.

Figure 13A:
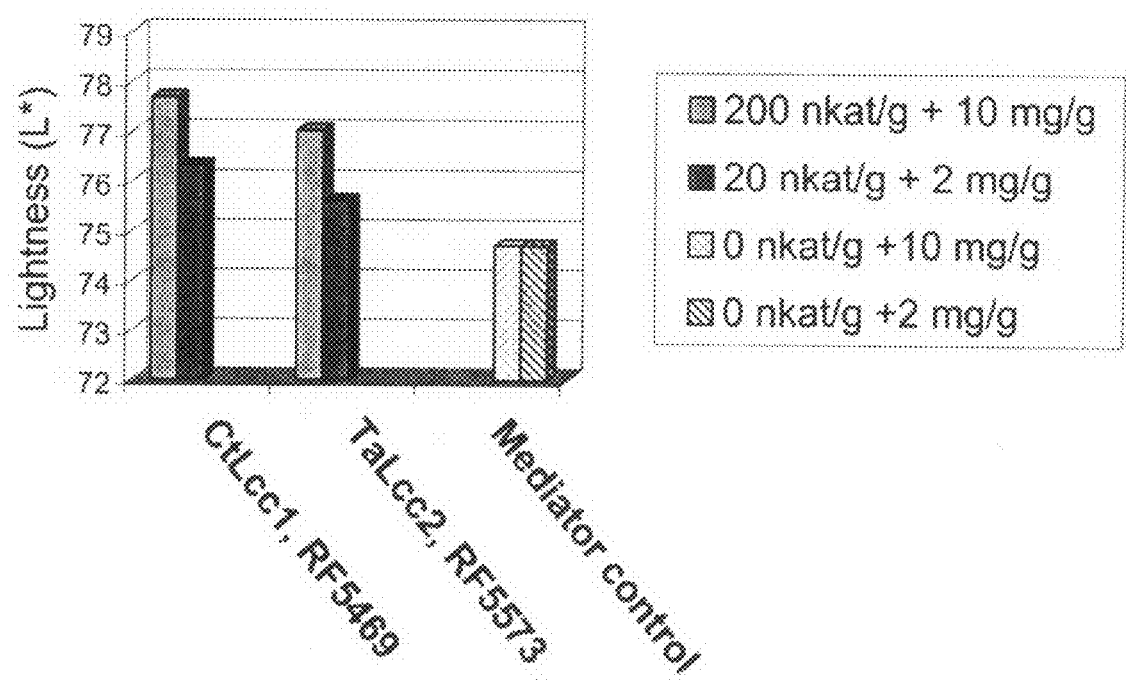
FIGS. 13A and B. Effect of laccase preparations on tea soiling at 40° C. with different dosages at conditions described in Example 10. A. Lightness values, B. a*-values (−a is the green direction, +a is the red direction)
Figure 13B:
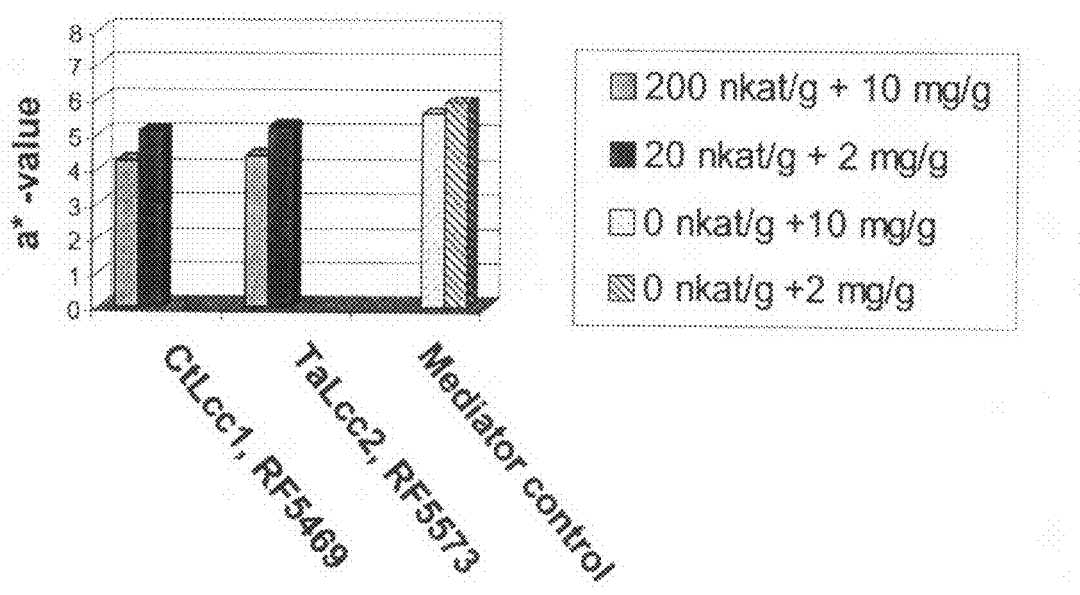

CtLcc1 laccase was effective in removal of tea soiling with the mediator at 60° C. and TaLcc2 laccase at 50° C., that can be seen in reduced redness and especially in increased lightness values in FIG. 11, and also clearly by visual estimation. Same trend can be seen at 40° C. (FIG. 13). Without the mediator the laccases did not have a notable effect on tea stain, especially at 40° C.

TABLE 21

Colour measurements of stain removal test with laccases at 50 and 60° C.

| Sample | Enz. dosage nkat/g | Mediator mg/g | Conditions | Grass L* | a* | b* | Tea L* | a* | b* |
|---|---|---|---|---|---|---|---|---|---|
| Artificially soiled cloth (untreated) | — | — | — | 78.32 | −10.18 | 25.31 | 69.27 | 8.56 | 25.80 |
| CtLcc1, RF5469 | 200 | 10 | 60 min, 60° C., pH 6 | 79.92 | −1.15 | 18.55 | 79.76 | 3.52 | 22.16 |
| CtLcc1, RF5469 | 200 | 0 | 60 min, 60° C., pH 6 | 79.04 | −3.69 | 18.12 | 77.10 | 4.84 | 21.10 |
| Mediator only | 0 | 10 | 60 min, 60° C., pH 6 | 77.98 | −6.80 | 19.26 | 75.54 | 5.00 | 20.5 |
| Buffer only | 0 | 0 | 60 min, 60° C., pH 6 | 77.93 | −6.70 | 19.31 | 75.55 | 4.94 | 20.58 |
| TaLcc2, RF5573 | 200 | 10 | 60 min, 50° C., pH 6 | 79.50 | −1.15 | 17.94 | 77.73 | 3.99 | 22.89 |

TABLE 21-continued

Colour measurements of stain removal test with laccases at 50 and 60° C.

| Sample | Enz. dosage nkat/g | Mediator mg/g | Conditions | Grass L* | a* | b* | Tea L* | a* | b* |
|---|---|---|---|---|---|---|---|---|---|
| TaLcc4, RF5687 | 200 | 10 | 60 min, 50° C., pH 6 | 78.62 | −4.00 | 17.16 | 75.13 | 5.19 | 22.44 |
| Mediator only | 0 | 10 | 60 min, 50° C., pH 6 | 77.95 | −6.45 | 18.56 | 75.97 | 4.84 | 20.47 |

L* indicates lightness,
−b* is the blue direction,
+b* is the yellow direction,
+a* is the red direction,
−a* is the green direction).
Untreated artifially soiled test cloth and mediator and buffer controls were used for comparision.

TABLE 22

Colour measurements of stain removal test with laccases at 40° C.

| Sample | Enz. dosage nkat/g | Mediator mg/g | Conditions | Grass L* | a* | b* | Tea L* | a* | b* |
|---|---|---|---|---|---|---|---|---|---|
| Artificially soiled cloth (untreated) | — | — | — | 78.18 | −8.88 | 25.29 | 69.36 | 8.65 | 25.8 |
| CtLcc1, RF5469 | 200 | 10 | 60 min, 40° C., pH 6 | 79.74 | 0.17 | 16.48 | 77.70 | 4.26 | 24.50 |
| TaLcc2, RF5573 | 200 | 10 | 60 min, 40° C., pH 6 | 79.19 | −0.26 | 16.99 | 77.04 | 4.41 | 24.36 |
| TaLcc2, RF5571 | 200 | 10 | 60 min, 40° C., pH 6 | 79.24 | −0.31 | 16.72 | 77.28 | 4.36 | 24.32 |
| TaLcc4, RF5687 | 200 | 10 | 60 min, 40° C., pH 6 | 78.94 | −3.77 | 16.77 | 74.56 | 5.58 | 23.55 |
| Mediator only | 0 | 10 | 60 min, 40° C., pH 6 | 78.88 | −6.19 | 18.28 | 74.72 | 5.63 | 22.16 |
| CtLcc1, RF5469 | 200 | 0 | 60 min, 40° C., pH 6 | 80.17 | −4.14 | 17.45 | 76.22 | 5.37 | 22.68 |
| TaLcc2, RF5573 | 200 | 0 | 60 min, 40° C., pH 6 | 80.01 | −4.90 | 17.63 | 76.09 | 5.37 | 22.59 |
| TaLcc4, RF5687 | 200 | 0 | 60 min, 40° C., pH 6 | 79.84 | −4.98 | 17.62 | 76.74 | 5.05 | 21.67 |
| Mediator only | 0 | 10 | 60 min, 40° C., pH 6 | 80.1 | −5.67 | 17.68 | 76.25 | 5.11 | 22.15 |
| Buffer only | 0 | 0 | 60 min, 40° C., pH 6 | 79.66 | −5.79 | 18.45 | 76.00 | 5.22 | 22.74 |
| CtLcc1, RF5469 | 20 | 2 | 60 min, 40° C., pH 6 | 79.94 | −1.20 | 16.17 | 76.34 | 5.10 | 23.89 |
| TaLcc1, RF5598 | 20 | 2 | 60 min, 40° C., pH 6 | 80.16 | −0.73 | 16.20 | 77.17 | 4.65 | 24.40 |
| TaLcc2, RF5573 | 20 | 2 | 60 min, 40° C., pH 6 | 79.25 | −2.14 | 16.41 | 75.61 | 5.24 | 23.66 |
| TaLcc4, RF5687 | 20 | 2 | 60 min, 40° C., pH 6 | 78.53 | −6.07 | 19.33 | 75.09 | 5.73 | 22.08 |
| Mediator only | 0 | 2 | 60 min, 40° C., pH 6 | 79.32 | −6.43 | 18.64 | 74.71 | 5.94 | 22.99 |

L* indicates lightness,
−b* is the blue direction,
+b* is the yellow direction,
+a* is the red direction,
−a* is the green direction).
Untreated artifially soiled test cloth and mediator and buffer controls were used for comparision.

EXAMPLE 10

Decolorization of Dyes Using Laccase Preparations

The recombinant laccases CtLcc1, TaLcc2 and TaLcc4, derived from *Trichoderma* strains (Example 7) were tested for their ability to decolorize different dyes in the presence of the methyl syringate mediator (Example 7) or without it. The experiments were carried out in 100 ml shake flasks containing 50 ml of dye dissolved in citrate phosphate buffer pH 6. Dye concentration 5 mg/50 ml was used. Enzyme was dosed 100 nkat per 50 ml and the mediator 5 mg per 50 ml. Control samples contained only dye solution. The shake flasks were incubated at 50° C. for 30, 60 and 120 minutes. Samples of 3.5 ml were taken in test tubes for visual evaluation.

The results are shown in Table 23 and 24. CtLcc1 and TaLcc2 laccases were able to decolourize Indigocarmine and Remazol Brilliant Blue (Reactive Blue 19) to great extend or completely and Cibacron Brilliant Red 3B-P partly in the presence of the mediator. Degradation of Indigocarmine was fast, and the blue colour had turned to light yellow in already 30 min or earlier. The reaction seemed to be completed after 60 min with all dyes, since no visually detectable changes in the colours of the samples were observed any more.

TABLE 23

Decolorization of dyes with CtLcc1 laccase.

| Dye 5 mg/50 ml | Enz. dosage nkat/50 ml | Mediator mg/50 ml | Time 30 min | Time 60 min |
|---|---|---|---|---|
| Cibacron Brilliant Red 3B-P (Ciba-Geigy) | 100 | 0 | − | − |
| Cibacron Brilliant Red 3B-P (Ciba-Geigy) | 100 | 5 | + | + |
| Remazol Brilliant Blue (Sigma) | 100 | 0 | − | − |
| Remazol Brilliant Blue (Sigma) | 100 | 5 | ++ | +++ |
| Indigocarmine (Merck) | 100 | 0 | − | − |
| Indigocarmine (Merck) | 100 | 5 | +++ | +++ |

Treatment time 30 and 60 min.
− no visually detectable change,
+ visually detectable fading of the colour,
++ considerable fading of the colour,
+++ complete/almost complete decolorization.

TABLE 24

Decolorization of dyes with TaLcc2 laccase.

| Dye 5 mg/50 ml | Enz. dosage nkat/50 ml | Mediator mg/50 ml | Time 30 min | Time 60 min |
|---|---|---|---|---|
| Cibacron Brilliant Red 3B-P (Ciba-Geigy) | 100 | 0 | − | − |
| Cibacron Brilliant Red 3B-P (Ciba-Geigy) | 100 | 5 | + | + |
| Remazol Brilliant blue (Sigma) | 100 | 0 | − | − |
| Remazol Brilliant blue (Sigma) | 100 | 5 | ++ | +++ |
| Indigocarmine (Merck) | 100 | 0 | − | − |
| Indigocarmine (Merck) | 100 | 5 | +++ | +++ |

Treatment time 30 and 60 min.
− no visually detectable change,
+ visually detectable fading of the colour,
++ considerable fading of the colour,
+++ complete/almost complete decolorization.

REFERENCES

Aho S, V Olkkonen, T Jalava, M Paloheimo, R Bühler, M-L Niku-Paavola, E H Bamford and M Korhola. 1991. Monoclonal antibodies against core and cellulose-binding domains of *Trichoderma reesei* cellobiohydrolases I and II and endoglucanase I. Eur. J. Biochem. 200:643-649.

Altschul S F, W Gish, W Miller, E W Myers and D J Lipman. 1990. Basic local alignment search tool. J. Mol. Biol. 215:403-410.

Chefetz, B, Z Kermer, Y Chen and Y Hadar. 1998a. Isolation and partial characterization of laccase from a thermophilic composted municipal solid waste, Soil Biol. Biochem. 30: 1091-1098.

Chefetz, B, Y Chen and Y Hadar. 1998b. Purification and characterization of laccase from *Chaetomium thermophilium* and its role in humification. Appl. Environ. Microbiol. 64:3175-3179.

Edman P and G Begg. 1967. Eur. J. Biochem. 1:80

Gasteiger, E, A Gattiker, C Hoogland, I Ivanyi, R D Appel and A Bairoch. 2003. ExPASy: the proteiomics server for in-depth protein knowledge and analysis. Nucleic Acids Res. 31:3784-3788.

Joutsjoki, V V, T K Torkkeli and K M H Nevalainen. 1993. Transformation of *Trichoderma reesei* with the *Hormocoinis resinae* glucoamylase P (gamP) gene: production of a heterologous glucoamylase by *Trichoderma reesei*. Curr. Genet. 24:223-228.

Karhunen T, A Mäntylä, K M H Nevalainen and P L Suominen. 1993. High frequency one-step gene replacement in *Trichoderma reesei*. I. Endoglucanase I overproduction. Mol. Gen. Genet. 241:515-522.

Kiiskinen, L-L, M Rättö and K Kruus. (2004) Screening for novel laccase-producing microbes *Journal of Applied Microbiology* 97:640-646

Laemmli U K (1970) Cleavage of structural proteins during the assembly of the head of bacteriophage T4. Nature 227:680-685

Leonowicz, A and K Grzywnowicz. 1981. Quantitative estimation of laccase forms in some white-rot-fungi using syringaldazine as a substrate. Enzyme Microb. Technol. 3, 55-58.

Lowry O H, N J Roseborough, A L Farr and R J Randall. 1951. Protein measurement with the Folin phenol reagent. J. Biol Chem 193: 265-275

Malardier L, M J Daboussi, J Julien, F Roussel, C Scazzocchio and Y Brygoo. 1989. Gene 15:147-156.

Niku-Paavola M-L, E Karhunen, P Salola and V Raunio. 1988. Ligninolytic enzymes of the white-rot fungus Phlebia radiata. Biochem J 254: 877-884

Paloheimo M, A Mantylä, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Palonen H, M Saloheimo, L Viikari L and K Kruus. 2003. Purification, characterization and sequence analysis of a laccase from the ascomycete *Mauginiella* sp. Enzyme Microb. Technol. 31: 403-410.

Paszczynski A, V-B Huynh and R Crawford. 1985. Enzymatic activities of an extracellular Mn-dependent peroxidase from *Phanerocahete chrysosporium*. FEMS Microbiol Lett 29:37-41

Penttilä M, H Nevalainen, M Rättö, E Salminen and J Knowles. 1987. A versatile transformation system for the cellulolytic filamentous fungus *Trichoderma reesei*. Gene 61:155-164.

Raeder U and P Broda. 1985. Rapid preparation of DNA from filamentous fungi. Lett. Appl. Microbiol. 1:17-20.

Rice P, I Longden and A Bleasby. 2000. EMBOSS: The European Molecular Biology Open Software Suite. Trends in Genetics 16:276-277.

Saito T, P Hong, K Kato, M Okazaki, H Inagaki, S Maeda and Y Yokogawa. 2003. Purification and characterization of an extracellular laccase of a fungus (family Chaetomiaceae) isolated from soil. Enzyme and Microbial Technol. 33:520-526.

Sambrook J, E F Fritsch and T Maniatis. 1989. Molecular cloning, a laboratory manual. Cold Spring Harbor Laboratory, New York, US.

Sambrook J and D W Russell. 2001. Molecular cloning, a laboratory manual. Cold Spring Harbor Laboratory, New York, US.

Schlosser D, R Grey, W Fritsche. 1997. Patterns of ligninolytic enzymes in *Trimetes versicolor*. Distribution of extra- and intracellular enzyme activities during cultivation on glucose, wheat straw and beech wood. Appl Microbiol Biotechnol 47:412-418

Sigoillot C, E Record, V Belle, J L Robert, A Levasseur, P J Punt, CAM van der Hondel, A Fourner, J C Sigoillot and M Aster. 2004. Natural and recombinant laccases for pulp and paper bleaching, Appl. Microbiol. Biotechnol. 64:346-352.

Stone K L, M B Lobresti, N D Williams, J M Crawford, R Deangelis and K R Williams. In Techniques in Protein Chemistry, p. 377-391. T. E. Hugli (ed.). Academisc Press, New York 1988.

Xu, F, W Shin, S Brown, J A Wahleithner, U M Sundaram and E I Solomon. 1996. A study of a series of recombinant fungal laccases and bilirubin oxidase that exhibit significant differences in redox potential, substrate specificity, and stability. Biochim. Biophys. Acta 1292:303-311.

What is claimed is:

1. A recombinant polypeptide having laccase activity, characterized in that it consists of the amino acid sequence of SEQ ID NO:41 (TaLcc2) or a sequence having at least 95% identity to the sequence SEQ ID NO:41 and being most effective in bleaching denim at temperatures 40-60° C.

2. The recombinant polypeptide according to claim 1, wherein the enzyme is obtained from a filamentous fungus.

3. The recombinant polypeptide according to claim 1, wherein the enzyme is obtained from the genus *Thielavia*.

4. The recombinant polypeptide according to claim 1, wherein the enzyme is effective in stain removal.

5. The recombinant polypeptide according to claim 1, wherein the enzyme is capable of decolorizing dyes.

6. The recombinant polypeptide according to claim 1, wherein the enzyme lacks the signal sequence.

7. The recombinant polypeptide according to claim 1, wherein the laccase is produced in a filamentous fungus host.

8. The recombinant polypeptide according to claim 7, wherein the enzyme is produced in a host of the genus *Trichoderma* or *Aspergillus*.

9. A recombinant polypeptide having laccase activity and being obtainable by culturing a host cell transformed with a nucleic acid sequence encoding the enzyme of claim 1.

10. An enzyme preparation obtainable by culturing a host cell transformed with a nucleic acid sequence encoding the enzyme of claim 1, said enzyme preparation being further recovered from the host cells or from supernatant separated from culture medium of the host cells.

11. An enzyme preparation, which comprises the recombinant polypeptide according to claim 1.

12. The enzyme preparation according to claim 11, wherein the enzyme preparation is the spent culture medium of the production host.

13. A method for treating denim, which comprises contacting denim in an aqueous medium with a laccase enzyme according to claim 1 or with an enzyme preparation according to claim 11 under suitable conditions for the function of the enzyme.

14. A method for stain removal, which comprises contacting material to be treated with a laccase enzyme according to claim 1 or with an enzyme preparation according to claim 11 under suitable conditions for the function of the enzyme.

15. A method of bleaching pulp, which comprises the step of contacting said pulp with a laccase enzyme according to claim 1 or with an enzyme preparation according to claim 11 under suitable conditions for the function of the enzyme.

16. A method for treating natural or man-made fibre, which comprises contacting fibre with a laccase enzyme according to claim 1 or with an enzyme preparation according to claim 11 under suitable conditions for the function of the enzyme.

17. A method for treating lignocellulosic fibre, which comprises contacting fibre with a laccase enzyme according to claim 1 or with an enzyme preparation according to claim 11 under suitable conditions for the function of the enzyme.

18. A method for treating wool, which comprises contacting wool with a laccase enzyme according to claim 1 or with an enzyme preparation according to claim 11 under suitable conditions for the function of the enzyme.

19. A method for treating hair, which comprises contacting hair with a laccase enzyme according to claim 1 or with an enzyme preparation according to claim 11 under suitable conditions for the function the enzyme.

20. A method for treating dye house effluents, which comprises contacting dye house effluents with a laccase enzyme according to claim 1 or with an enzyme preparation according to claim 11 under suitable conditions for the function of the enzyme.

21. A method for decolorizing of dyes, which comprises contacting dyes or dye containing material with a laccase enzyme according to claim 1 or with an enzyme preparation according to claim 11 under suitable conditions for the function of the enzyme.

* * * * *